ical Patent [19] [11] Patent Number: 6,150,386
Trah et al. [45] Date of Patent: Nov. 21, 2000

[54] PESTICIDAL TRIS-OXIMINO HETEROCYCLIC COMPOUNDS

[75] Inventors: Stephan Trah, Freiburg, Germany; René Zurflüh, Basel, Switzerland

[73] Assignee: Novartis Crop Protection, Inc., Greensboro, N.C.

[21] Appl. No.: 08/981,574

[22] PCT Filed: Jun. 10, 1996

[86] PCT No.: PCT/EP96/02518

§ 371 Date: Dec. 22, 1997

§ 102(e) Date: Dec. 22, 1997

[87] PCT Pub. No.: WO97/00866

PCT Pub. Date: Jan. 9, 1997

[30] Foreign Application Priority Data

Jun. 22, 1995 [CH] Switzerland ............... 1835/95
Apr. 25, 1996 [CH] Switzerland ............... 1051/96

[51] Int. Cl.[7] .................................................. C07D 271/06
[52] U.S. Cl. .................... 514/364; 514/229.2; 544/65; 548/131; 548/143; 562/868; 564/157; 564/164
[58] Field of Search ..................... 548/131, 143; 544/65; 514/229.2, 364; 564/157, 164; 582/868

[56] References Cited

FOREIGN PATENT DOCUMENTS

| 74972/94 | 2/1995 | Australia . |
|---|---|---|
| 14546/95 | 6/1996 | Australia . |
| 0 472 300 | 2/1992 | European Pat. Off. . |
| WOA94 22844 | 10/1994 | WIPO . |
| WOA95 18789 | 6/1995 | WIPO . |

*Primary Examiner*—Robert Gerstl
*Attorney, Agent, or Firm*—Michael P. Morris; John D. Peabody, III; William A. Teoli, Jr.

[57] ABSTRACT

Compounds of formula (I) and their possible isomers and isomer mixtures, in which (Z) is a group (a), (b), (c) or (d) and in which the other substituents are as defined herein. They can be used for pest control, in particular as microbicides, insecticides and acaricides in agriculture, in horticulture and in the hygiene sector

32 Claims, No Drawings

PESTICIDAL TRIS-OXIMINO HETEROCYCLIC COMPOUNDS

The invention relates to novel pesticidally active compounds of the formula I

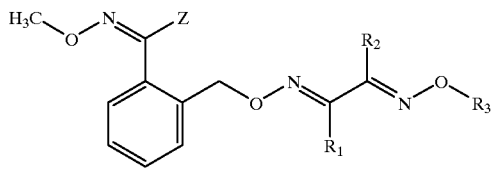

and their possible isomers and isomer mixtures, in which a) Z is a group 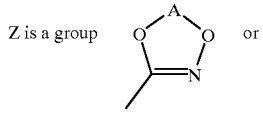 or b) 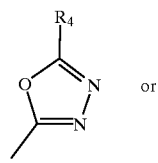 or c) 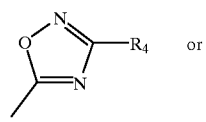 or d) 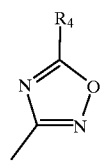

and in which the other substituents are defined as follows:

A alkanediyl which is unsubstituted or substituted by methyl and has 1 to 3 carbon atoms, preferably dimethylene (ethane-1,2-diyl);

$R_4$ hydrogen, $C_1$–$C_3$alkyl, cyclopropyl or $CF_3$;

$R_1$ hydrogen, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or cyano;

$R_2$ hydrogen, $C_1$–$C_6$alkyl, $C_3$–$C_6$cycloalkyl, cyano, substituted or unsubstituted $C_1$–$C_6$alkoxycarbonyl, substituted or unsubstituted di-($C_1$–$C_6$alkyl)aminocarbonyl, substituted or unsubstituted heteroaryl, substituted or unsubstituted heterocyclyl, naphthyl;

a group 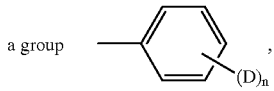,

-continued a group 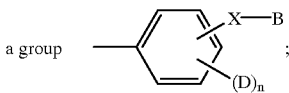;

D identical or different halogen, $C_1$–$C_4$alkyl, $C_1$–$C_6$alkoxy, $C_1$–$C_2$haloalkyl, $C_1$–$C_2$haloalkoxy, $C_3$–$C_6$alkenyloxy, $C_3$–$C_6$alkynyloxy, $C_1$–$C_4$alkylenedioxy, $C_3$–$C_6$-cycloalkyl, $C_1$–$C_4$-alkoximino-$C_1$–$C_2$alkyl, $C_1$–$C_8$-alkiminoxy, cyanomethoxy, cyano-$C_1$–$C_2$alkoxy, cyano, nitro, thioamido, thiocyanatomethyl, $C_1$–$C_4$alkoxy-$C_1$–$C_2$alkoxy, halo-$C_1$–$C_6$alkylsulfonyl, di-$C_1$–$C_4$alkylarnino-$C_1$–$C_4$alkoxy, $C_2$–$C_4$alkynyl, substituted or unsubstituted phenyl, substituted or unsubstituted heteroaryl, tri($C_1$–$C_4$alkyl)silyl or di($C_1$–$C_4$alkyl)phenylsilyl;

n 0,1,2,3 or 4;

X —O—, —O—($C_1$–$C_4$alkyl)—, —($C_1$–$C_4$alkyl)—O—, —S(O)$_m$—, —($C_1$–$C_4$alkyl)—S(O)$_m$— or —S(O)$_m$—($C_1$–$C_4$-Alkyl)—;

m 0, 1 or 2;

B $C_1$–$C_6$alkyl, halo-$C_1$–$C_6$alkyl, $C_3$–$C_6$cycloalkyl, $C_2$–$C_6$alkenyl which is unsubstituted or substituted by 1 to 3 halogen atoms, or $C_3$–$C_6$alkynyl, or furthermore aryl, heteroaryl or heterocyclyl, all three of which independently of one another are unsubstituted or substituted one to five times by $C_1$–$C_6$alkyl, halo-$C_1$–$C_6$alkyl, halogen, $C_1$–$C_6$alkoxy or halo-$C_1$–$C_6$alkoxy, tri($C_1$–$C_4$alkyl)silyl, di($C_1$–$C_4$alkyl)phenylsilyl or a group

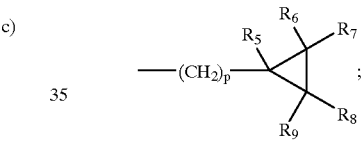;

$R_5$, $R_6$, $R_7$, $R_8$ and $R_9$ independently of one another hydrogen, $C_1$–$C_4$alkyl or halogen and p 0,1,2 or 3;

$R_3$ hydrogen, $C_1$–$C_6$alkyl, $C_1$–$C_6$haloalkyl having 1 to 5 halogen atoms, $C_1$–$C_4$alkoxy-$C_1$–$C_2$alkyl, $C_2$–$C_6$alkenyl which is unsubstituted or substituted by 1 to 3 halogen atoms, $C_2$–$C_6$alkynyl, $C_3$–$C_6$cycloalkyl which is unsubstituted or substituted by 1 to 4 halogen atoms, $C_3$–$C_6$cycloalkyl-$C_1$–$C_4$alkyl which is unsubstituted or substituted by 1 to 4 halogen atoms, cyano-$C_1$–$C_4$alkyl, $C_1$–$C_4$alkoxycarbonyl-$C_1$–$C_2$alkyl, phenyl-$C_1$–$C_3$alkyl which is unsubstituted or substituted by halogen, $C_1$–$C_3$alkyl, $C_1$–$C_4$alkoxy, $C_1$–$C_4$haloalkyl, cyano, nitro or $C_1$–$C_4$alkylenedioxy, where the phenyl group can be substituted one to three times in an identical or different manner; phenyl which is unsubstituted or substituted once or twice, independently of one another, by $C_1$–$C_4$alkyl, $C_1$–$C_4$alkoxy, halogen, $C_1$–$C_2$haloalkyl having 1 to 3 halogen atoms, nitro or cyano; or pyridyl which is unsubstituted or substituted once or twice, independently of one another by $C_1$–$C_4$alkyl, $C_1$–$C_4$alkoxy, halogen, $C_1$–$C_2$haloalkyl having 1 to 3 halogen atoms, nitro or cyano.

The compounds according to the invention have fungicidal, acaricidal and insecticidal properties and are suitable as active compounds for use in agriculture, in horticulture and in the hygiene sector.

The invention furthermore relates to a process for the preparation of the compounds according to the invention, and to fungicidal, acaricidal and insecticidal compositions which comprise such compounds as active compounds, and to the use of such compounds and compositions for the control of phytopathogenic fungi, Acarina and insects and for prevention of such infestation.

If asymmetric carbon atoms are present in the compounds of the formula I, the compounds occur in an optically active form. In any case, merely because of the presence of the aliphatic, the oximino and the hydrazono double bonds, the compounds occur in [E] and/or [Z] forms. Atropisomerism furthermore can occur. Formula I is intended to include all these possible isomeric forms and mixtures thereof, for example racemic mixtures and any [E/Z] mixtures.

The general terms used above and below are as defined below, unless defined otherwise:

Halogen is fluorine, chlorine, bromine or iodine, in particular fluorine, chlorine or bromine, especially fluorine or chlorine.

Alkyl is either straight-chain, for example methyl, ethyl, n-propyl, n-butyl, n-hexyl, n-octyl, n-decyl, n-dodecyl, n-hexadecyl or n-octadecyl, or branched, for example isopropyl, isobutyl, sec-butyl, tert-butyl, isopentyl, neopentyl or isohexyl.

Alkenyl is straight-chain or branched alkenyl, for example vinyl, 1-methylvinyl, allyl, 1-butenyl, isopropenyl, in particular allyl.

Alkynyl is, for example, ethynyl, 1-propynyl or 1-butynyl, in particular propargyl.

Cycloalkyl is to be understood as meaning cyclopropyl, cyclobutyl, cyclopentyl or cyclohexyl.

Halogen-substituted groups, such as haloalkyl and haloalkoxy, can be partly or completely halogenated and carry identical or different halogen atoms.

Straight-chain $C_1$–$C_4$alkylenedioxy is —O—$CH_2$—O—, —O—$CH_2CH_2$—O—, —O—$CH_2CH_2CH_2$—O— or —O—$CH_2CH_2CH_2CH_2$—O—.

The substituted or unsubstituted alkoxycarbonyl and dialkylaminocarbonyl groups are substituted 1 to 3 times by identical or different atoms or groups chosen from halogen atoms, cyano, methoxy, methylthio, cyclopropyl, alkenyl and alkynyl.

The substituted or unsubstituted heteroaryl and heterocyclyl groups are substituted 1 to 3 times in an identical or different manner by $C_1$–$C_4$alkyl, halogen, cyano, nitro, $C_1$–$C_4$alkoxy, $C_1$–$C_4$alkylthio, halo-$C_1$–$C_2$alkyl, halo-$C_1$–$C_2$alkoxy, $C_1$–$C_4$alkoxycarbonyl.

Aryl is phenyl or naphthyl, preferably phenyl.

The term heteroaryl includes furan, thiophene, pyrrole and aromatic 5-membered rings having two to three and six-membered rings having one to three identical or different heteroatoms N, O or S, it being possible for all of these to be benzo-fused. Individual examples are pyridine, pyrimidine, pyrazine, thiazole, oxazole, isoxazole, isothiazole, triazine, quinoline, isoquinoline, pyridazine, pyrazole, imidazole, quinazoline, quinoxaline, benzimidazole, benzofuran, indole, isoindole, benzothiazole, benzothiophene and thiadiazole.

The term heterocyclyl means 5- to 7-membered rings which contain 1–3 identical or different heteroatoms N, O or S. Examples are $\Delta^2$-oxazoline; $\Delta^2$-thiazoline; 5,6-dihydro-4H-1,3-thiazine; and 5,6-dihydro-4H-1,3-oxazine, and furthermore pyrrolidine, piperidine, morpholine, 4-alkylpiperidine and azepine.

Important compounds of the formula I are those in which

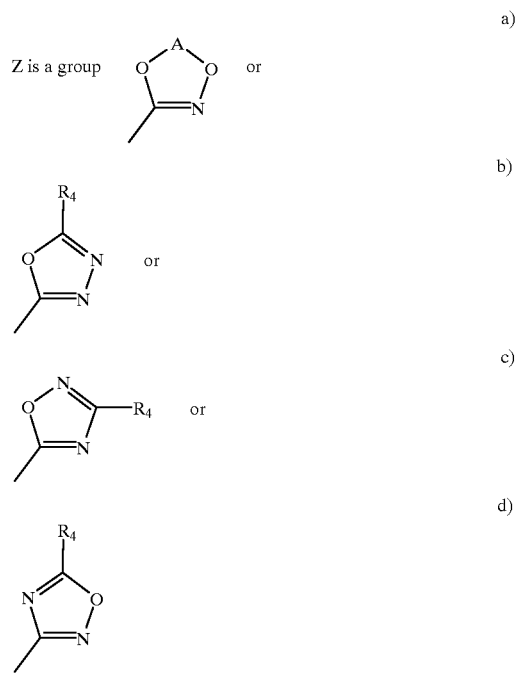

and in which the other substituents are defined as follows:
A alkanediyl which is unsubstituted or substituted by methyl and has 1 to 3 carbon atoms;
$R_4$ hydrogen, $C_1$–$C_3$alkyl, cyclopropyl or $CF_3$;
$R_1$ hydrogen, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or cyano;
$R_2$ hydrogen, $C_1$–$C_6$alkyl, $C_3$–$C_6$cycloalkyl, cyano, substituted or unsubstituted $C_1$–$C_6$alkoxycarbonyl, substituted or unsubstituted di-($C_1$–$C_6$alkyl)aminocarbonyl, substituted or unsubstituted heteroaryl, substituted or unsubstituted heterocyclyl or naphthyl;

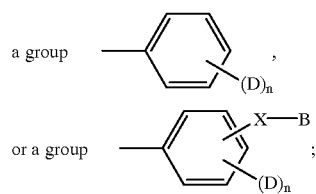

D identical or different halogen, $C_1$–$C_4$alkyl, $C_1$–$C_4$alkoxy, $C_1$–$C_2$haloalkyl, $C_1$–$C_2$haloalkoxy, $C_3$–$C_6$alkenyloxy, $C_3$–$C_6$alkynyloxy, $C_1$–$C_4$alkylenedioxy, cyano or nitro, $C_2$–$C_4$alkynyl, substituted or unsubstituted phenyl or substituted or unsubstituted heteroaryl;
n 0, 1, 2, 3 or 4;
X —O—, —O—($C_1$–$C_4$alkyl)—, —($C_1$–$C_4$alkyl)—O—, —S(O)$_m$—, —($C_1$–$C_4$alkyl)—S(O)$_m$— or —S(O)$_m$—($C_1$–$C_4$alkyl)—;
m 0, 1 or 2;
B $C_1$–$C_6$alkyl, halo-$C_1$–$C_6$alkyl, $C_3$–$C_6$cycloalkyl, $C_2$–$C_6$alkenyl which is unsubstituted or substituted by 1 to 3 halogen atoms, or $C_3$–$C_6$alkynyl, or furthermore aryl, heteroaryl or heterocyclyl, all three of which independently of one another are unsubstituted or substituted once to five times by $C_1$–$C_6$alkyl, halo-$C_1$–$C_6$alkyl, halogen, $C_1$–$C_6$alkoxy or halo-$C_1$–$C_6$alkoxy, tri($C_1$–$C_4$alkyl)silyl, di($C_1$–$C_4$alkyl)phenylsilyl or a group

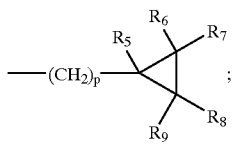

$R_5$, $R_6$, $R_7$, $R_8$ and $R_9$ independently of one another hydrogen, $C_1$–$C_4$alkyl or halogen and p 0,1,2 or 3;

$R_3$ hydrogen, $C_1$–$C_6$alkyl, $C_1$–$C_6$haloalkyl having 1 to 5 halogen atoms, $C_1$–$C_4$-alkoxy-$C_1$–$C_2$alkyl, $C_2$–$C_6$alkenyl which is unsubstituted or substituted by 1 to 3 halogen atoms, $C_2$–$C_6$alkynyl, $C_3$–$C_6$cycloalkyl which is unsubstituted or substituted by 1 to 4 halogen atoms, $C_3$–$C_6$cycloalkyl-$C_1$–$C_4$alkyl which is unsubstituted or substituted by 1 to 4 halogen atoms, cyano-$C_1$–$C_4$alkyl, $C_1$–$C_4$alkoxycarbonyl-$C_1$–$C_2$alkyl, phenyl-$C_1$–$C_3$alkyl which is unsubstituted or substituted by halogen, $C_1$–$C_3$alkyl, $C_1$–$C_4$alkoxy, $C_1$–$C_4$haloalkyl, cyano, nitro or $C_1$–$C_4$alkylenedioxy, where the phenyl group can be substituted one to three times in an identical or different manner; phenyl which is unsubstituted or substituted once or twice, independently of one another, by $C_1$–$C_4$alkyl, $C_1$–$C_4$alkoxy, halogen, $C_1$–$C_2$haloalkyl having 1 to 3 halogen atoms, nitro or cyano; or pyridyl which is unsubstituted or substituted once or twice, independently of one another, by $C_1$–$C_4$alkyl, $C_1$–$C_4$alkoxy, halogen, $C_1$–$C_2$haloalkyl having 1 to 3 halogen atoms, nitro or cyano (subgroup 1 A).

Preferred compounds of the formula I are those in which
Z is a group a) (subgroup A).

In the scope of this group A, preferred compounds of the formula I are those in which
A is ethane-1,2-diyl and
$R_1$ is $C_1$–$C_4$alkyl or cyclopropyl;
$R_2$ is $C_1$–$C_4$alkyl, $C_1$–$C_4$alkoxycarbonyl, heteroaryl or a group

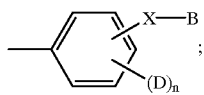

$R_3$ is $C_1$–$C_4$alkyl, $C_2$–$C_4$alkenyl which is unsubstituted or substituted by 1 to 3 halogen atoms, $C_1$–$C_4$haloalkyl or $C_3$–$C_4$alkynyl (subgroup A1a).

A particular group from these is formed by those compounds in which
A is ethane-1,2-diyl and
$R_1$ is $C_1$–$C_4$alkyl or cyclopropyl;
$R_2$ is $C_1$–$C_4$alkyl, $C_1$–$C_4$alkoxycarbonyl, heteroaryl or a group

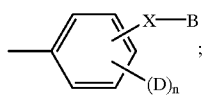

$R_3$ is $C_1$–$C_4$alkyl or $C_2$–$C_4$alkenyl which is unsubstituted or substituted by 1 to 3 halogen atoms (subgroup Aa).

Compounds of the formula I from subgroup Aa which are specifically preferred are those in which
$R_2$ is heteroaryl (subgroup Ab), in particular those in which $R_2$ is 2-pyridine (subgroup Ac).

An important group of compounds of the formula I from subgroup Aa are those in which $R_2$ is a group

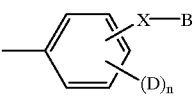

(subgroup Aaa).

Within the group Aaa, preferred compounds of the formula I are those in which
D is identical or different and is fluorine, chlorine or bromine and
n is 0, 1 or 2, and
X is —O—, —O—($C_1$–$C_4$alkyl)— or —($C_1$–$C_4$alkyl)—O— (subgroup Aab).

Another important group of compounds of the formula I is formed by those in which
Z is a group b) and
$R_1$ is hydrogen, $C_1$–$C_4$alkyl or cyclopropyl (subgroup B).

Preferred compounds of the formula I from subgroup B are those in which
$R_4$ is hydrogen or methyl; and
$R_2$ is hydrogen, $C_1$–$C_4$alkyl, cyclopropyl, heteroaryl, a group

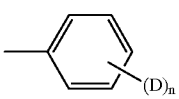

or a group

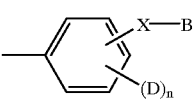

(subgroup Ba).

Particularly preferred compounds of the formula I from subgroup Ba are those in which
$R_4$ is hydrogen or methyl; and
$R_2$ is hydrogen, $C_1$–$C_4$alkyl, cyclopropyl, heteroaryl, a group

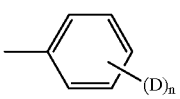

or a group

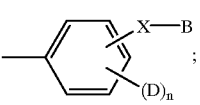

and
$R_3$ is $C_1$–$C_4$alkyl, $C_2$–$C_4$aLkenyl which is unsubstituted or substituted by 1 to 3 halogen atoms, $C_1$–$C_4$haloalkyl or $C_3$–$C_4$alkynyl (subgroup Ba1).

Important compounds of the formula I from subgroup Ba are those in which
$R_4$ is hydrogen (subgroup Bb).

A preferred subgroup of compounds from subgroup Bb are those in which
$R_2$ is heteroaryl (subgroup Bc).

Another important subgroup of compounds of the formula I from subgroup Ba are those in which
$R_2$ is a group

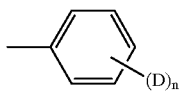

or a group

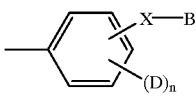

and

D is identical or different and is fluorine, chlorine or bromine, $C_1$–$C_4$alkyl or $C_1$–$C_3$alkoxy,
n is 0, 1 or 2; and
X is —O—, —O—($C_1$–$C_4$alkyl)— or —($C_1$–$C_4$alkyl)—O— (subgroup Baa).

An important group are compounds of the formula I in which
Z is a group c) and
$R_1$ is $C_1$–$C_4$alkyl or cyclopropyl (subgroup C).

Within the compounds of the formula I from subgroup C, those which are of importance are those in which
$R_4$ is hydrogen;
$R_2$ is hydrogen, $C_1$–$C_4$alkyl, cyclopropyl, heteroaryl, a group

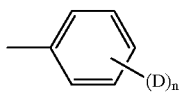

or a group

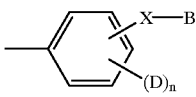

(subgroup Ca).

Particularly preferred compounds from subgroup Ca are those in which
$R_2$ is heteroaryl (subgroup Cb).

Another preferred group of compounds of the formula I from subgroup Ca are those in which
$R_2$ is a group

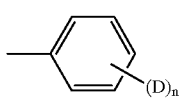

or a group

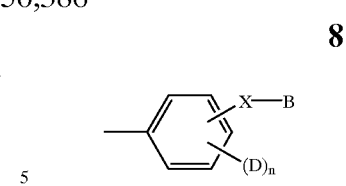

and

D is identical or different and is fluorine, chlorine or bromine, $C_1$–$C_4$alkyl or $C_1$–$C_3$alkoxy and
n is 0, 1 or 2; while
X is —O—, —O—($C_1$–$C_4$alkyl)— or —($C_1$–$C_4$alkyl)—O— (subgroup Caa).

Preferred compounds of the formula I are all those in which the $CH_3ON=C$— double bond in the upper part of the formula shown has the E form.

In the description for the preparation of the compounds of the formula I, in the following formulae of sections A) to D), unless stated otherwise, the radicals A, X and $R_4$ are as defined for formula I, while
Q is the group

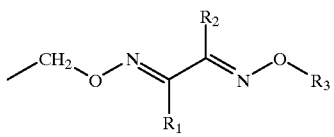

in which
$R_1$, $R_2$ and $R_3$ likewise are as defined for formula I.

A) The compounds of the formula III can be prepared in accordance with equation 1 by a method analogous to known methods, as described, for example, in WO 95/04728:

Equation 1

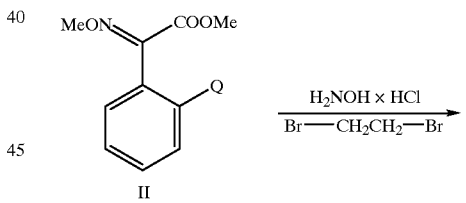

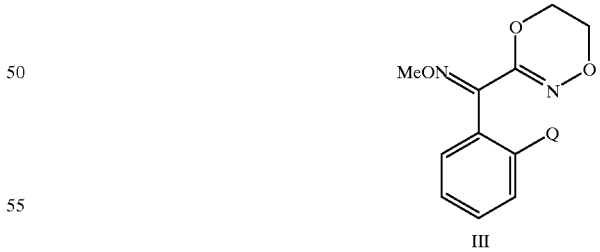

The starting materials 11 can be prepared by generally known methods, for example in accordance with equation 3.

B) The compounds of the formula I in which Z is a group b) or c) can be prepared in accordance with the following equation 2 by generally known methods, as described, for example, in Houben-Weyl, "Methoden der organischen Chemie" [Methods of organic chemistry], Volume E8c, page 409 et seq. and 526 et seq. and in WO 94/22844.

Equation 2
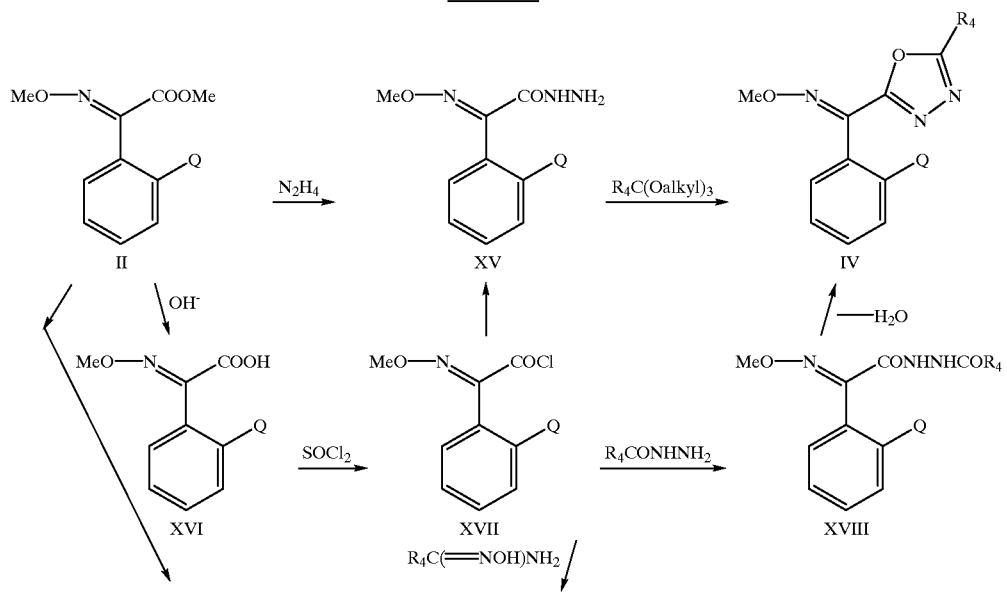
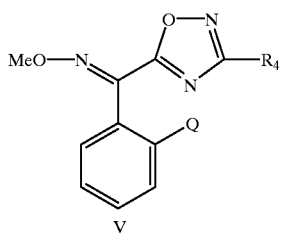
The preparation of the starting materials shown in the following equation 3 is described, for example, in EP-A-506149 (VI) or EP-A-254426 (VII and VIII).
The invention also relates to the intermediates of the formulae XV, XVI, XVII and XVIII.
Equation 3
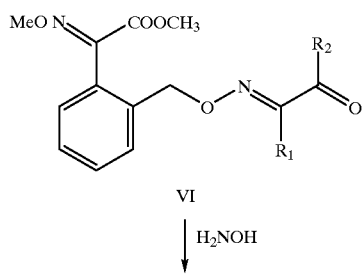

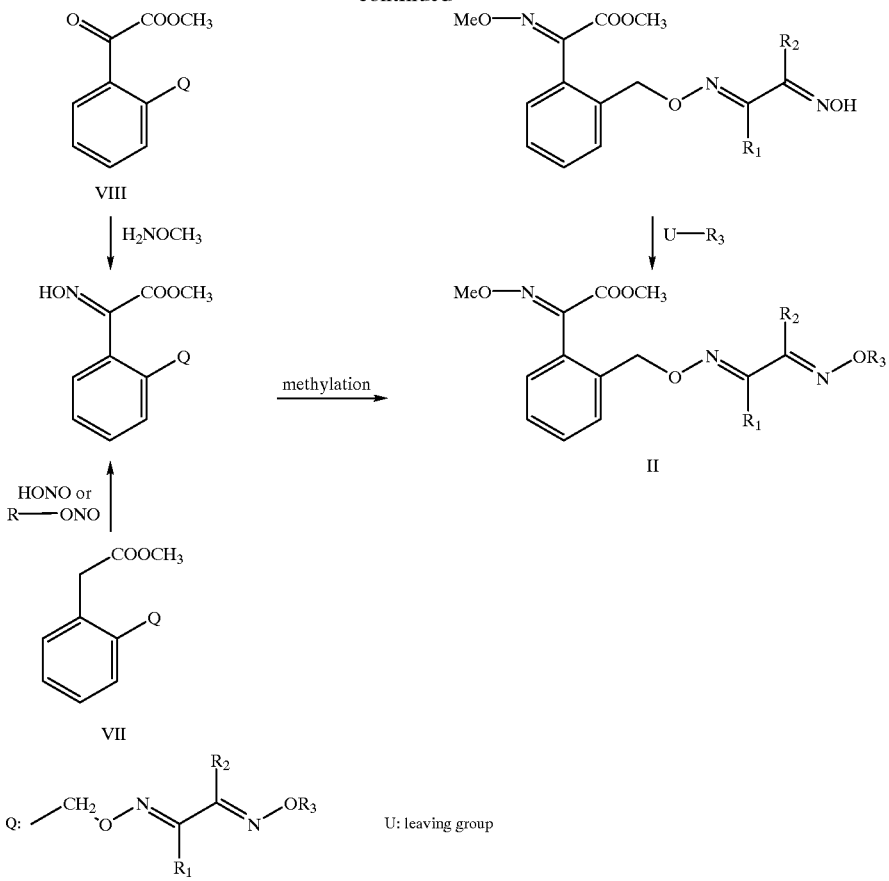

C) The compounds of the formula I in which Z is the group d) can be prepared in accordance with the following equation 4 by generally known methods, as described, for example, in Houben-Weyl, "Methoden der organischen Chemie" [Methods of organic chemistry], Volume E8c, page 409 et seq, and in WO 94/22844.

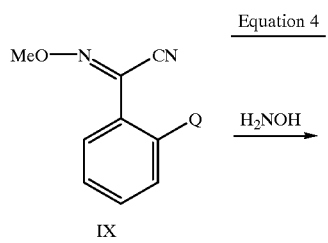

Equation 4

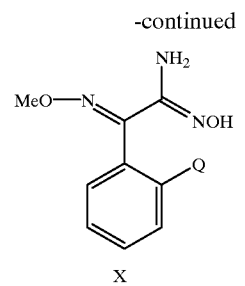

The starting materials IX can be prepared by generally known methods, for example in accordance with equation 5.

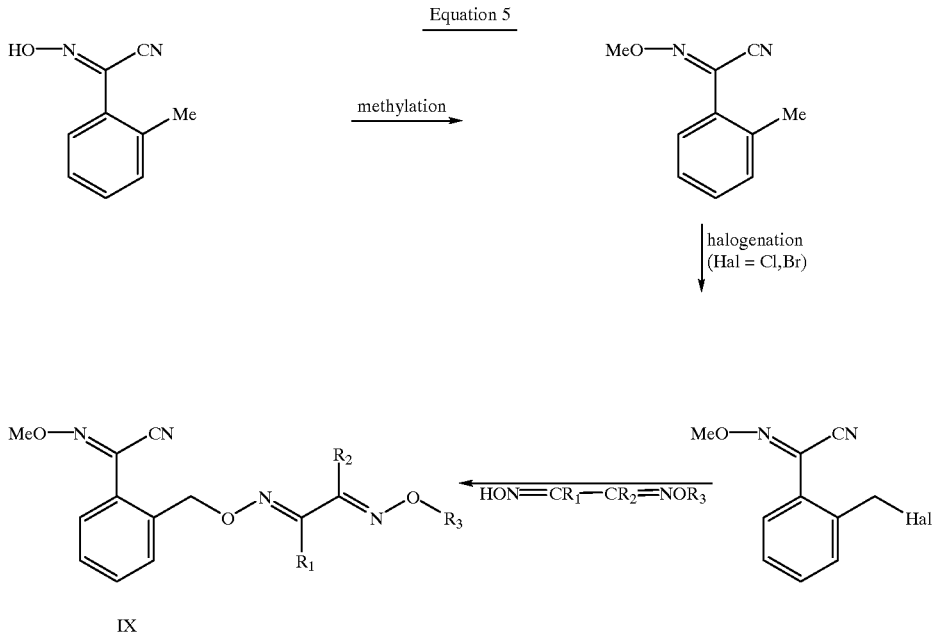

Equation 5

D) In another embodiment, the compounds of the formula I in which Z is the groups a) to d) of formula I can be prepared in accordance with the following equation 6, by generally known methods.

In another embodiment, the compounds of the formula I in which Z is a group c) or d) can be prepared in accordance with the following equation 6 by generally known methods, as described, for example, in Houben-Weyl, Volume E8c, page 409 et seq.

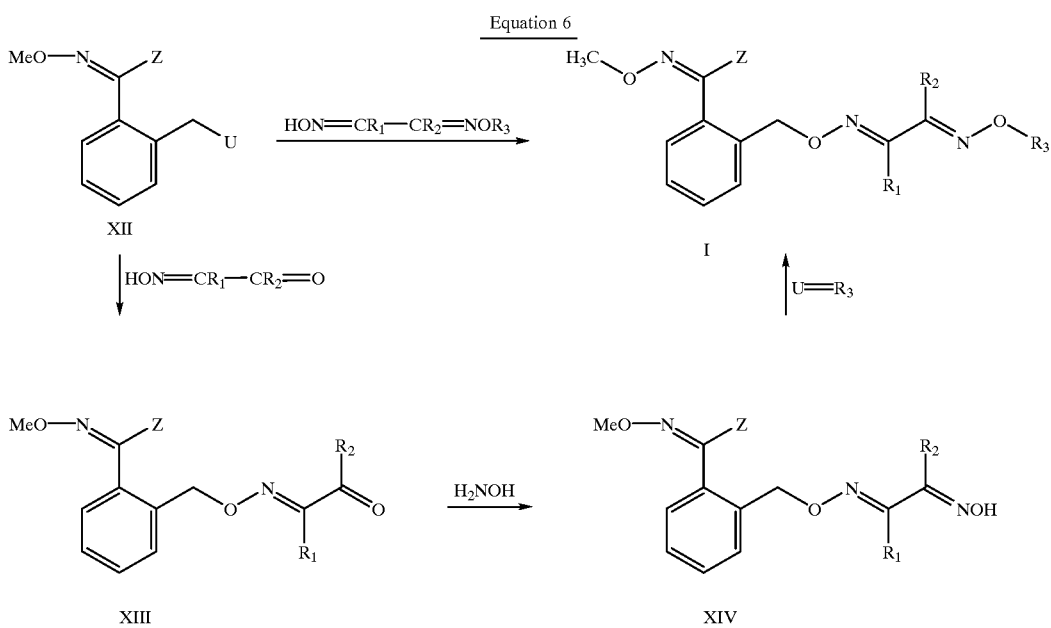

Equation 6

U: Leaving group (for example halogen)

The starting materials XII can be prepared by generally known methods, as described, for example, in WO 94/22844 and WO 95/4728.

The invention furthermore relates to the intermediate of the formula XIII.

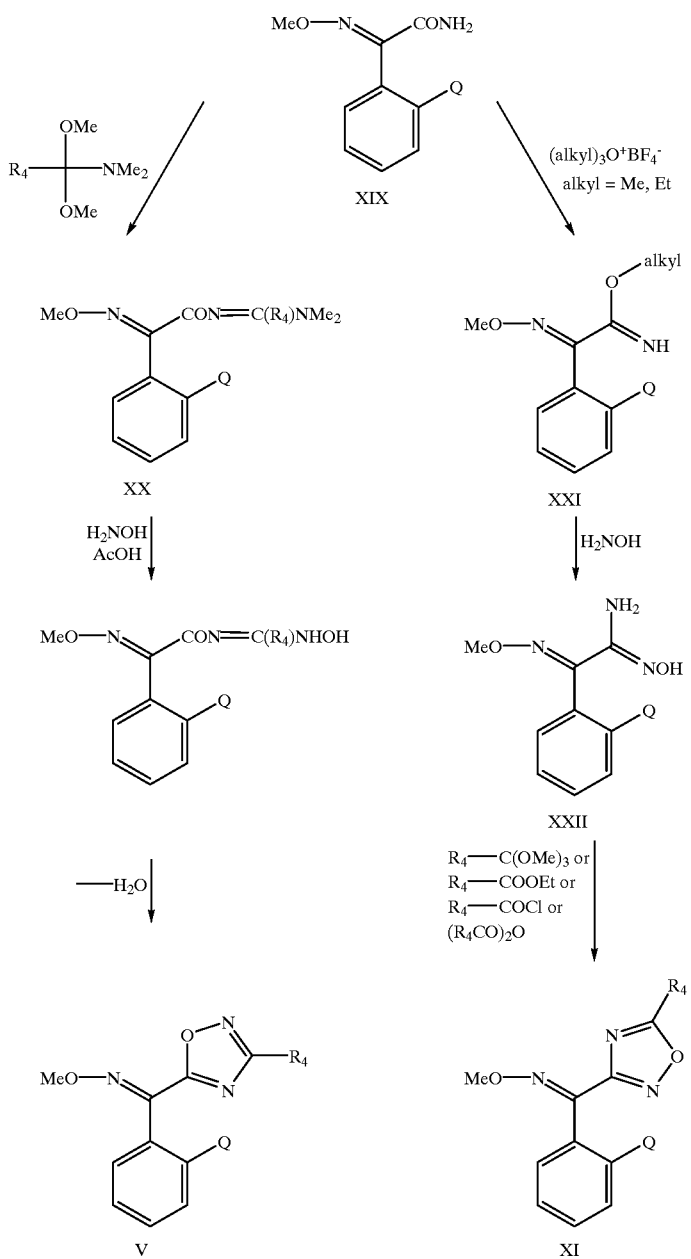

Equation 7

The starting materials XIX can be prepared by generally known methods, for example in accordance with WO-95/18789.

The invention further-more relates to the intermediates XX.

It has now been found that compounds of the formula I have a microbicidal spectrum which is particularly favourable for practical requirements for the control of phytopathogenic microorganisms, in particular fungi. They have very advantageous curative, preventive and, in particular, systemic properties and can be employed for the protection of numerous plants. The pests which occur on plants or parts of plants (fruit, blossom, foliage, stems, tubers, roots) of various crops of useful plants can be checked or destroyed using the active compounds of the formula I, parts of plants which additionally grow later also remaining protected from phytopathogenic microorganisms.

The compounds of the formula I can furthermore be employed as dressing compositions for the treatment of seed (fruits, tubers, grains) and plant seedlings for protection against fungal infections and against phytopathogenic fungi occuring in the soil.

Compounds of the formula I are active, for example, against the phytopathogenic fungi belonging to the following classes: Fungi imperfecti (in particular Botrytis, Pyricularia, Helminthosporium, Fusarium, Septoria, Cercospora, Pseudocercosporella and Alternaria); Basidiomycetes (for example Rhizoctonia, Hemileia, Puccinia); Ascomycetes (for example Venturia and Erysiphe, Podosphaera, Monilinia, Uncinula), and in particular also against Oomycetes (for example Phytophthora, Peronospora, Bremia, Pythium, Plasmopara).

The compounds of the formula I according to the invention furthermore are valuable active compounds against insects and pests of the order Acarina such as occur on useful plants and ornamentals in agriculture and in horticulture and in forestry. The compounds of the formula I are particularly suitable for controlling pests in cotton, vegetable, fruit and rice crops, such as spider mites, aphids, butterfly caterpillars and rice cicadas. Spider mites such as *Panonychus ulmi*, aphids such as *Aphis craccivora*, butterfly caterpillars such as those of *Heliothis virescens* and rice cicadas such as *Nilaparvata lugens* or *Nephotettix cincticeps* can chiefly be controlled.

The good pesticidal action of the compounds I according to the invention corresponds to a destruction rate (mortality) of at least 50–60% of the pests mentioned.

Other fields of use of the active compounds according to the invention are the protection of stored products and materials where the goods stored are protected against rotting and moulding and against animal pests (for example grain weavils, mites, fly maggots and the like). In the hygiene sector, compounds of the formula I effect successful control of animal parasites, such as ticks, mites, warble flies and the like on domestic animals and productive livestock. The compounds I are active against individual or all development stages of normally sensitive and also resistant species of pests. Their action can manifest itself here, for example, in a destruction of the pests occuring immediately or only after some time, for example at molting, or in a reduced oviposition and/or hatching rate.

The action of the compounds I according to the invention and of the compositions comprising them can be broadened substantially and adapted to given circumstances by addition of other insecticides and/or acaricides. Additives are, for example, representatives of the following classes of active compound: organic phosphorus compounds, nitrophenols and derivatives, formamidines, ureas, carbamates, pyrethroids and chlorinated hydrocarbons.

In the context of this invention, examples of target crops for the plant-protecting use disclosed herein are the following species of plants: cereals (wheat, barley, rye, oats, triticale, rice, maize, sorghum and related species); beet (sugar and feeding beet); pome, stone and soft fruit (apples, pears, plums, peaches, almonds, cherries, strawberries, gooseberries, raspberries and blackberries); leguminous plants (beans, lentils, peas and soya); oil crops (oilseed rape, mustard, poppy, olive, sunflower, coconut, castor, cacao and groundnut); cucumber plants (pumpkins, cucumbers and melons); fibre plants (cotton, flax, hemp and jute); citrus fruits (oranges, lemons, grapefruits and mandarins); varieties of vegetables (spinach, lettuce, asparagus, cabbage species, carrots, onions, tomatoes, potatoes and capsicums); lauraceous plants (avocado, cinnamonium and camphor), or plants such as tobacco, nuts, coffee, cane sugar, tea, peppers and other spice plants, vines, hops, aubergines, musaceae and natural rubber plants as well as flowers and ornamentals.

Active compounds of the formula I are usually used in the form of compositions and can be introduced onto the area or plants to be treated at the same time as or after other active compounds. These other active compounds can be both fertilizers and suppliers of trace elements, or other preparations which influence plant growth. It is also possible to use here selective herbicides, as well as other insecticides, fungicides, bactericides, nematicides, molluscicides or mixtures of several of these preparations, together with, where appropriate, other carriers, surfactants or other application-promoting additives conventionally used in the art of formulation, without the activity of the compounds of the formula I being impaired.

Suitable carriers and additives can be solid or liquid and are the substances used for this purpose in the art of formulation, for example naturally occurring or regenerated mineral substances, solvents, dispersing agents, wetting agents, tackifiers, thickeners, binders or fertilizers.

Solvents are: aromatic hydrocarbons, preferably fractions $C_8$ to $C_{12}$, for example xylene mixtures or substituted naphthalenes, phthalic acid esters, such as dibutyl or dioctyl phthalate, aliphatic hydrocarbons, such as cyclohexane or paraffins, alcohols and glycols and ethers and esters thereof, such as ethanol, ethylene glycol, ethylene glycol monomethyl ether or ethyl ether, ketones, such as cyclohexanone, strongly polar solvents, such as N-methyl-2-pyrrolidone, dimethyl sulfoxide or dimethylformamide, and epoxidized or non-epoxidized vegetable oils, such as epoxidized coconut oil or soya oil; or water.

The solid carriers used, for example for dusts and dispersible powders, are as a rule naturally occurring rock powders, such as calcite, talc, kaolin, montmorillonite or attapulgite.

Particularly advantageous application-promoting adjuvants, which can lead to a marked reduction in the rate of application, are furthermore naturally occurring (animal or vegetable) or synthetic phospholipids from the series consisting of cephalins and lecithins, which can be obtained, for example, from soy beans.

Surface-active compounds are, depending on the nature of the active compound of the formula I to be formulated, nonionic, cationic and/or anionic surfactants having good emulsifying, dispersing and wetting properties. Surfactants are also to be understood as meaning surfactant mixtures.

Suitable anionic surfactants can be both so-called water-soluble soaps and water-soluble synthetic surface-active compounds.

Soaps are the alkali metal, alkaline earth metal or substituted or unsubstituted ammonium salts of higher fatty acids ($C_1O$-$C_{22}$), for example the Na or K salts of oleic or stearic acid, or of naturally occurring fatty acid mixtures, which can be obtained, for example, from coconut oil or tallow oil. They are also the fatty acid methyltaurine salts.

Nonionic surfactants are polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Examples of nonionic surfactants are nonylphenol-polyoxyethanols, castor oil polyglycol ethers, polypropylene/polyethylene oxide adducts, tributylphenoxypolyethoxyethanol, polyethylene glycol and octylphenoxypolyethoxyethanol.

They can also be fatty acid esters of polyoxyethylene sorbitan, such as polyoxyethylene sorbitan trioleate.

The cationic surfactants are, in particular, quaternary ammonium salts which contain at least one alkyl radical having 8 to 22 C atoms as substituents on N and lower, non-halogenated or halogenated alkyl, benzyl or lower hydroxyalkyl radicals as further substituents.

The anionic, nonionic or cationic surfactants conventionally used in the art of formulation are known to the expert or can be found in the relevant technical literature.

The agrochemical formulations as a rule comprise 0.1 to 99%, in particular 0.1 to 95%, of active compound of the formula I, 99.9 to 1%, in particular 99.9 to 5%, of a solid or liquid additive and 0 to 25%, in particular 0.1 to 25%, of a surfactant.

While concentrated compositions are more preferable as commercial goods, the end user as a rule uses dilute compositions.

The compositions can also comprise further additives, such as stabilizers, foam suppressants, viscosity regulators, binders, tackifiers and fertilizers, or other active compounds to achieve specific effects.

The formulations, i.e. the compositions, preparations or combinations comprising the active compound of the formula I and, if appropriate, a solid or liquid additive, are prepared in a known manner, for example by intimate mixing and/or grinding of the active compound with an extender, for example with a solvent (mixture), a solid carrier material and, if appropriate, surface-active compounds (surfactants).

A preferred method for application of an active compound of the formula I or of an agrochemical composition which comprises at least one of these active compounds is application to the foliage (leaf application). The application frequency and rate of application depend here on the risk of infestation by the pathogen in question. However, the active compounds of the formula I can also enter the plants via the soil through the root system (systemic action), by soaking the locus of the plants with a liquid formulation or introducing the substances into the soil in solid form, for example in the form of granules (soil application). In the case of paddy rice crops, such granules can be metered into the flooded rice field. However, the compounds of the formula I can also be applied to seed grains (coating), by either soaking the grains in a liquid formulation of the active compound or coating them with a solid formulation. In principle, any type of plant propagation material can be protected with compounds of the formula I, for example the seed, roots, stems, branches or shoots.

The compounds of the formula I are employed here in unchanged form or, preferably, together with the auxiliaries conventionally used in the art of formulation. For this, they are advantageously processed in a known manner, for example to emulsion concentrates, spreadable pastes, directly sprayable or dilutable solutions, dilute emulsions, wettable powders, soluble powders, dusts or granules (by encapsulation in, for example, polymeric substances). The methods of use, such as spraying, atomizing, dusting, scattering, brushing on or watering, are chosen according to the intended aims and the given circumstances, as is also the nature of the composition. Favourable rates of application are in general 1 g to 2 kg of active substance (AS) per ha, preferably 25 g to 800 g of AS/ha, and particularly preferably 50 g to 400 g of AS/ha. When used as a seed dressing, dosages of 0.001 to 1.0 g of active compound per kg of seed are advantageously used.

The following examples serve to illustrate the invention in more detail without limiting it.

1. PREPARATION EXAMPLES

Example H-1: Preparation of

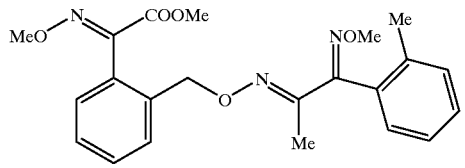

XXVI

↓

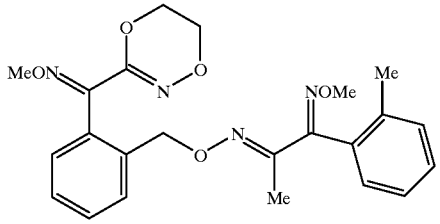

Compound No. 4.1

1.74 g (25 mmol) of hydroxylamine hydrochloride are initially introduced into 20 ml of methanol at room temperature, and a solution of 3.3 g of potassium hydroxide (90%) in 20 ml of methanol is added. 5.27 g (12.8 mmol) of XXVI are then added and the reaction mixture is stirred at 40° C. for one hour. First 1.8 g (12.8 mmol) of potassium carbonate and then 5.1 ml (59 mmol) of 1,2-dibromoethane are subsequently added to the reaction mixture. The mixture is stirred under reflux for 16 hours and then filtered. The filtrate is concentrated in vacuo and the residue is purified by column chromatography over silica gel (ethyl acetate/hexane 1:4). After recrystallization (diethyl etherihexane), compound No. 4.1 is obtained as colourless crystals, melting point 112–114° C.

Example H-2: Preparation of

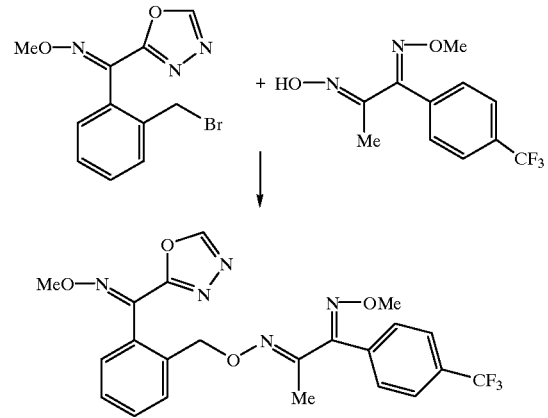

Compound No. 5.6

1.3 g of 1-(4-trifluoromethyl-phenyl)-propane-1,2-dione 1-(O-methyloxime)-2-oxime and 2.27 g of (2-bromomethyl-phenyl)-[1,3,4]-oxadiazol-2-yl-methanone 0-methyloxime, known from WO 94/22844, are dissolved in 15 ml of acetonitrile, 1.38 g of potassium carbonate are added and the mixture is then stirred at 80° C. for 1.5 hours. The green suspension is cooled to room temperature, stirred into 100 ml of water and extracted three times with 80 ml of ethyl acetate. The combined organic extracts are washed twice with half-saturated sodium chloride solution, dried over magnesium sulfate and evaporated on a Rotavap. The oily residue is chromatographed over 100 g of silica gel with hexane/ethyl acetate (9:1) and then crystallized from MTBE/hexane (1:4). The compound 5.6 is obtained as white crystals of melting point 146° C.

Example H-3: Preparation of

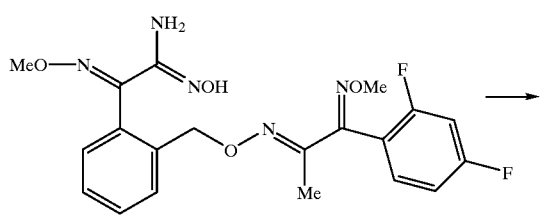

XXIII

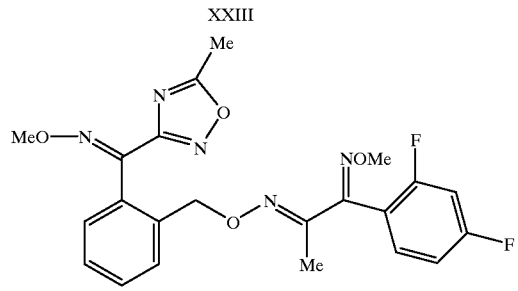

Compound No. 11.73

One drop of concentrated sulfuric acid is added to the suspension of 1.08 g of the amide-oxime XXIII in 4.8 g of trimethyl orthoacetate. The reaction mixture is then kept at the reflux temperature for 1 hour. The cooled mixture is chromatographed directly over 200 g of silica gel with hexane/ethyl acetate 4:1. The compound 11.73 is obtained as a colourless resin.

$^1$H-NMR: 1.99(s,3H), 2.64(s,3H), 3.92(s,3H), 4.03(s,3H), 4.93(s,2H), 6.74–6.84(m,2H), 6.95–7.04(m,1H), 7.22–7.42 (m,4H).

The starting material can be prepared as follows:

2.4 ml of triethylamine and 1.23 g of hydroxylamine hydrochloride are added to a solution of 6.74 g of O-methyl 2-{2-[2-(2,4-difluorophenyl)-2-methoximino-1-methyl-ethylideneaminooxy-methyl]-phenyl}-2-methoximino-acetimidate (prepared from the corresponding acetamide and trimethyloxonium tetrafluoroborate) in 50 ml of methanol at room temperature. After 1.5 hours, 20 ml of saturated sodium bicarbonate solution are added to the suspension. The white solid is filtered off, washed with 30 ml of water and dried (45° C., 100 mbar). The amide-oxime XXIII is obtained as crystals of melting point 160° C.

Example H-4: Preparation of

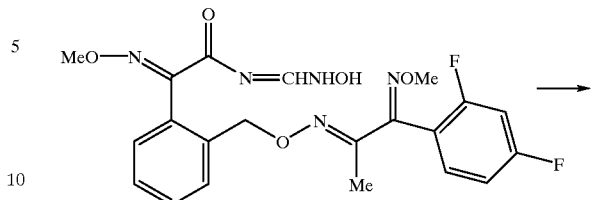

XXIV

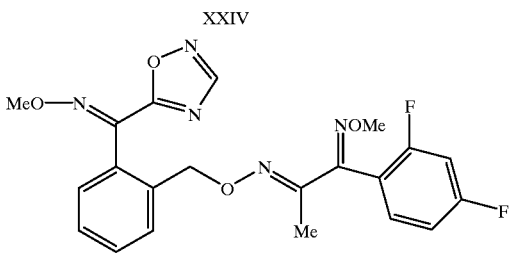

Compound No. 6.73

1.5 g of XXIV are dissolved in 20 ml of acetic acid and the solution is heated at 100° C. for 45 minutes, becoming orange in colour. The cooled reaction mixture is stirred into 100 ml of water and extracted three times with 20 ml of ethyl acetate. The combined organic extracts are evaporated on a Rotavap and the oily residue is chromatographed over 160 g of silica gel with hexane/ethyl acetate 9:1 to 8:2. The compound 6.73 is obtained as a resin.

$^1$H-NMR: 1.92(s,3H), 3.92(s,3H), 4.08(s,3H), 4.91(s,2H), 6.74–6.83(m,2H), 6.93–7.03(m,1H), 7.25–7.34(m,2H), 7.40–7.45(m,2H), 8.44(s,1H).

The starting material can be prepared as follows:

A suspension of 2.51 g of 2-{2-[2-(2,4-difluorophenyl)-2-methoximino-1-methyl-ethylideneaminooxymethyl]-phenyl}-2-methoximino-acetamide in 4.5 ml of N,N-dimethylformamide dimethyl acetal is stirred at 100° C. for 1 hour. The yellow solution formed is concentrated on a Rotavap and the residue is dried under a high vacuum (50° C., 0.03 mbar). The corresponding N-dimethylaminomethylene-acetamide is obtained as a highly viscous oil.

$^1$H-NMR : 2.13(s,3H), 3.03(s,3H), 3.11(s,3H), 3.92(s, 3H), 3.98(s,3H), 4.95(s,2H), 6.75–6.85(m,2H), 7.01–7.13 (m,1H), 7.15–7.17(m,1H), 7.26–7.34(m,3H), 8.49(s,1H).

1.9 g of the compound thus obtained are initially introduced into 5.6 ml of dioxane, and a solution of 0.39 g of hydroxylamine hydrochloride in 5.6 ml of 1N NaOH is added at room temperature. 7.5 ml of acetic acid are then added and the yellowish solution is stirred first at room temperature for 15 minutes and then at 90° C. for 30 minutes. The cooled reaction mixture is stirred into 200 ml of ice-water and the white solid is filtered off, washed with 50 ml of water and dried at 45° C. under 100 mbar. The compound XXIV is obtained as white crystals of melting point 58–61° C.

$^1$H-NMR: 2.08(s,3H), 3.93(s,3H), 4.00(s,3H), 4.90(s, broad,1H), 4.96(s,2H), 6.76–6.83(m,2H), 6.94–7.03(m,1H), 7.15–7.18(m,1H), 7.26–7.29(m,1H), 7.35–7.42(m,2H), 7.71 (d,1H), 9.19(d,1H).

Example H-5: Preparation of

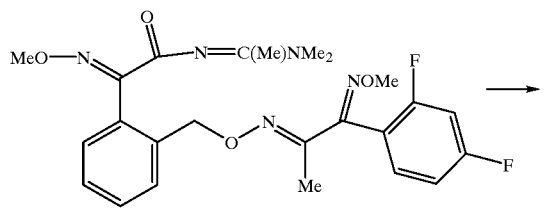

XXV

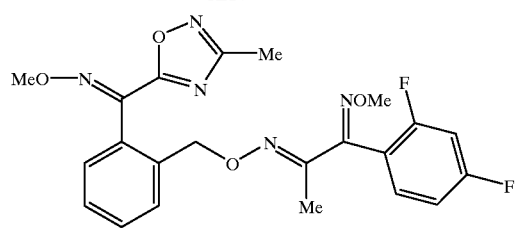

Compound No. 15.73

1.95 g of XXV are initially introduced into 6 ml of dioxane, and a mixture of 0.39 g of hydroxylamine hydrochloride in 5.6 ml of 1N NaOH is added at room temperature. 7.5 ml of acetic acid are added to the suspension formed, and the mixture is then stirred first at room temperature for 30 minutes and then at 90° C. for 15 minutes. The cooled reaction solution is stirred into 100 ml of water and then extracted three times with 50 ml of ethyl acetate. The combined organic extracts are washed twice with 10 ml of water and concentrated on a Rotavap. The oily residue is crystallized from methyl tert-butyl ether/hexane. The compound 15.73 is obtained as crystals of melting point 93–94° C.

The starting material can be prepared as follows:

A suspension of 2.51 g of 2-{2-[2-(2,4-difluorophenyl)-2-methoximino-1-methyl-ethylideneaminooxymethyl]-phenyl}-2-methoximino-acetamide (prepared from the corresponding methyl ester by means of $NH_3$-MeOH) and 5.5 ml of N,N-dimethylacetamide dimethyl acetal is heated to 120° C. and stirred at this temperature for 1 hour. The excess acetal is then distilled off on a Rotavap and the residue is dried under a high vacuum. Compound XXV is obtained as a highly viscous oil.

The compounds in the tables can be prepared in this manner or in the manner of one of the methods described.

Abbreviations: Ac=acetyl; Et=ethyl; i-Pr=isopropyl; Me=methyl; Ph=phenyl; Pr=n-propyl; Bu=n-butyl; m.p.=melting point; DS=diastereomer; Reg=regioisomer; "E" and "Z" relate to the configuration of the double bond. "NMR" is "nuclear magnetic resonance spectrum". MS=mass spectrum. "%" is "percent by weight", if corresponding concentrations are not stated in another unit.

The physical data in the tables are m.p. or 1H-NMR of $R_1/R_2$ or $R_3$ or MS molecular peak (relative intensity) and base peak.

The symbol "-" in the X column means that the compound carries no substituent X-B.

TABLE 1

| Example No. | $R_1$ | $R_2$ | $R_3$ | Physical data |
|---|---|---|---|---|
| 1.1 | Me | Me | Me | m.p. 116–118° C. |
| 1.2 | H | Me | Me | |
| 1.3 | Δ | Me | Me | |
| 1.4 | Me | Δ | Me | |
| 1.5 | Me | H | Me | |
| 1.6 | Me | Me | Phenyl | |
| 1.7 | Me | Δ | Phenyl | |
| 1.8 | Me | Me | Benzyl | |
| 1.9 | Me | Me | Et | |
| 1.10 | H | Me | Et | |
| 1.11 | Δ | Me | Et | |
| 1.12 | Me | Δ | Et | |
| 1.13 | Me | H | Et | |
| 1.14 | H | Me | Methoxymethyl | |
| 1.15 | Me | Me | Methoxymethyl | |
| 1.16 | Me | Δ | Methoxymethyl | |
| 1.17 | Δ | Me | Methoxymethyl | |
| 1.18 | Me | Me | Ethoxymethyl | |
| 1.19 | H | Me | Cyanomethyl | |
| 1.20 | Me | Me | Cyanomethyl | |
| 1.21 | Δ | Me | Cyanomethyl | |
| 1.22 | H | Me | tert-Butyl | |
| 1.23 | Me | Me | tert-Butyl | |
| 1.24 | Me | Me | Propargyl | |
| 1.25 | Δ | Me | Propargyl | |
| 1.26 | Me | Δ | Propargyl | |
| 1.27 | Me | Me | 2,2-Dichloro-cyclopropylmethyl | |
| 1.28 | Δ | Me | 2,2-Dichloro-cyclopropylmethyl | |
| 1.29 | H | Me | H | |
| 1.30 | Me | Me | H | |
| 1.31 | Me | Me | $CF_3CH_2$ | |
| 1.32 | Δ | Me | $CF_3CH_2$ | |
| 1.33 | Me | H | $CF_3CH_2$ | |
| 1.34 | Me | H | $CF_3CH_2CH_2$ | |
| 1.35 | Me | Me | $CF_3CH_2CH_2$ | |
| 1.36 | Me | Me | $CF_3CH_2CH_2CH_2$ | |
| 1.37 | Δ | Me | $CF_3CH_2CH_2CH_2$ | |
| 1.38 | Me | Me | Propyl | |
| 1.39 | Me | Me | Butyl | |
| 1.40 | Me | Me | Hexyl | |
| 1.41 | Me | Me | 3-Fluorobenzyl | |
| 1.42 | Me | Me | 4-Chlorobenzyl | |
| 1.43 | Me | Me | 2-Chlorobenzyl | |
| 1.44 | Me | Me | 2-$CF_3$-Benzyl | |
| 1.45 | Me | Me | 3-$CF_3$-Benzyl | |
| 1.46 | Me | Me | 4-$CF_3$-Benzyl | |
| 1.47 | Me | Me | 3,4-Dichlorobenzyl | |
| 1.48 | Me | Me | 2,4,6-Trimethylbenzyl | |
| 1.49 | Me | Me | 4-Chloro-2-nitrobenzyl | |
| 1.50 | Me | Me | 3-Methoxybenzyl | |
| 1.51 | Me | Me | 2-Phenethyl | |
| 1.52 | Me | Me | 3-Phenylpropyl | |
| 1.53 | Me | Me | 2-(4-Nitrophenyl)ethyl | |
| 1.54 | Me | Me | 2-(2-$CF_3$-Phenyl)ethyl | |
| 1.55 | Me | Me | 2-(4-Methoxyphenyl)ethyl | |
| 1.56 | Me | Me | 2-Chloro-6-fluorobenzyl | |
| 1.57 | Me | Me | 3,4-Methylenedioxybenzyl | |

TABLE 1-continued

| Example No. | R₁ | R₂ | R₃ | Physical data |
|---|---|---|---|---|
| 1.58 | Me | Me | 2-Cyanobenzyl | |
| 1.59 | Me | Me | Methoxycarbonylmethyl | |
| 1.60 | H | Me | Methoxycarbonylmethyl | |
| 1.61 | Me | Me | 2-(4-Chlorophenyl)ethyl | |
| 1.62 | Me | Me | Cyclopropylmethyl | |
| 1.63 | Me | Me | CH₂CH₂F | |
| 1.64 | Me | CN | Et | |
| 1.65 | Me | CN | t-Butyl | |
| 1.66 | Me | CN | Propargyl | |
| 1.67 | Me | CN | Cyclopropylmethyl | |
| 1.68 | Me | CN | CH₂CH₂F | |
| 1.69 | Me | CN | CH₂CH₂CH₂F | |
| 1.70 | Me | CN | 2,2-Dichlorocyclopropylmethyl | |
| 1.71 | H | CN | Me | |
| 1.72 | CN | CN | Me | |
| 1.73 | Et | CN | Me | |
| 1.74 | Δ | CN | Me | |
| 1.75 | Me | COOMe | Et | |
| 1.76 | Me | COOMe | t-Butyl | |
| 1.77 | Me | COOMe | Propargyl | |
| 1.78 | Me | COOMe | Cyclopropylmethyl | |
| 1.79 | Me | COOMe | CH₂CH₂F | |
| 1.80 | Me | COOMe | CH₂CH₂CH₂CF₃ | |
| 1.81 | Me | COOMe | 2,2-Dichlorocyclopropylmethyl | |
| 1.82 | Me | COOMe | Methoxymethyl | |
| 1.83 | H | COOMe | Me | |
| 1.84 | CN | COOMe | Me | |
| 1.85 | Δ | COOMe | Me | |
| 1.86 | Me | COOEt | Me | |
| 1.87 | Me | COOPropyl | Me | |
| 1.88 | Me | COOC(Me)₃ | Me | |
| 1.89 | Me | COOCH(Me)₂ | Me | |
| 1.90 | Me | COOCH₂-cyclopropyl | Me | |
| 1.91 | Me | COOCH₂CH=CH₂ | Me | |
| 1.92 | Me | COOCH₂≡CH | Me | |
| 1.93 | Me | COOCH₂CN | Me | |
| 1.94 | Me | COOCH₂CF₃ | Me | |
| 1.95 | Me | COOCH₂CH₂OMe | Me | |
| 1.96 | Me | COOCH₂CH₂SMe | Me | |
| 1.97 | Me | CON(Me)₂ | Me | |
| 1.98 | Me | CON(Me)Et | Me | |
| 1.99 | Me | CON(Et)₂ | Me | |
| 1.100 | Me | CON(Me)Propyl | Me | |
| 1.101 | Me | CON(CH₂CH₂CN)₂ | Me | |
| 1.102 | Me | 2-Δ²-Thiazolinyl | Me | |
| 1.103 | Me | 2-Thiazolyl | Me | |
| 1.104 | Me | 2-Pyridyl | Me | resin |
| 1.105 | Me | 3-Pyridyl | Me | |
| 1.106 | Me | 4-Pyridyl | Me | |
| 1.107 | Me | 2-Pyrimidinyl | Me | |
| 1.108 | Me | 4-Pyrimidinyl | Me | |
| 1.109 | Me | 2-Pyrazinyl | Me | |
| 1.110 | Me | COOBenzyl | Me | |
| 1.111 | Me | 2-Thienyl | Me | |
| 1.112 | Me | 5-Me-2-Thienyl | Me | |
| 1.113 | Me | 5-Et-2-Thienyl | Me | |
| 1.114 | Me | 2-Furyl | Me | |
| 1.115 | Me | 5-Me-2-Furyl | Me | |
| 1.116 | Me | 5-Et-2-Furyl | Me | |
| 1.117 | Me | 5-Methylthio-2-thienyl | Me | |
| 1.118 | Me | 2-Quinoxalinyl | Me | |
| 1.119 | Me | 2-Benzothiazolyl | Me | |
| 1.120 | Me | 2-Benzo[b]thienyl | Me | |
| 1.121 | Me | 5-Me-3-Isoxazolyl | Me | |
| 1.122 | Me | 4-Me-(1,2,3-Thiadiazol)-5-yl | Me | |
| 1.123 | Me | 1-Me-2-Pyrrolyl | Me | |
| 1.124 | Me | 1-Naphthyl | Me | |
| 1.125 | Me | 2-Naphthyl | Me | |
| 1.126 | Me | 4-Biphenyl | Me | |

TABLE 2

| Example No. | R₁ | R₂ | R₃ | Physical data |
|---|---|---|---|---|
| 2.1 | Me | Me | Me | m.p. 109–110° C. |
| 2.2 | H | Me | Me | |
| 2.3 | Δ | Me | Me | |
| 2.4 | Me | Δ | Me | |
| 2.5 | Me | H | Me | |
| 2.6 | Me | Me | Phenyl | |
| 2.7 | Me | Δ | Phenyl | |
| 2.8 | Me | Me | Benzyl | |
| 2.9 | Me | Me | Et | |
| 2.10 | H | Me | Et | |
| 2.11 | Δ | Me | Et | |
| 2.12 | Me | Δ | Et | |
| 2.13 | Me | H | Et | |
| 2.14 | H | Me | Methoxymethyl | |
| 2.15 | Me | Me | Methoxymethyl | |
| 2.16 | Me | Δ | Methoxymethyl | |
| 2.17 | Δ | Me | Methoxymethyl | |
| 2.18 | Me | Me | Ethoxymethyl | |
| 2.19 | H | Me | Cyanomethyl | |
| 2.20 | Me | Me | Cyanomethyl | |

TABLE 2-continued (structure: CH₃O-N=C(1,3,4-oxadiazol-2-yl)-phenyl-CH₂-O-N=C(R₁)-C(R₂)=N-OR₃)

| Example No. | R₁ | R₂ | R₃ | Physical data |
|---|---|---|---|---|
| 2.21 | Δ | Me | Cyanomethyl | |
| 2.22 | H | Me | tert-Butyl | |
| 2.23 | Me | Me | tert-Butyl | |
| 2.24 | Me | Me | Propargyl | |
| 2.25 | Δ | Me | Propargyl | |
| 2.26 | Me | Δ | Propargyl | |
| 2.27 | Me | Me | 2,2-Dichloro-cyclopropylmethyl | |
| 2.28 | Δ | Me | 2,2-Dichloro-cyclopropylmethyl | |
| 2.29 | H | Me | H | |
| 2.30 | Me | Me | H | |
| 2.31 | Me | Me | CF₃CH₂ | |
| 2.32 | Δ | Me | CF₃CH₂ | |
| 2.33 | Me | H | CF₃CH₂ | |
| 2.34 | Me | H | CF₃CH₂CH₂ | |
| 2.35 | Me | Me | CF₃CH₂CH₂ | |
| 2.36 | Me | Me | CF₃CH₂CH₂CH₂ | |
| 2.37 | Δ | Me | CF₃CH₂CH₂CH₂ | |
| 2.38 | Me | Me | Propyl | |
| 2.39 | Me | Me | Butyl | |
| 2.40 | Me | Me | Hexyl | |
| 2.41 | Me | Me | 3-Fluorobenzyl | |
| 2.42 | Me | Me | 4-Chlorobenzyl | |
| 2.43 | Me | Me | 2-Chlorobenzyl | |
| 2.44 | Me | Me | 2-CF₃-Benzyl | |
| 2.45 | Me | Me | 3-CF₃-Benzyl | |
| 2.46 | Me | Me | 4-CF₃-Benzyl | |
| 2.47 | Me | Me | 3,4-Dichlorobenzyl | |
| 2.48 | Me | Me | 2,4,6-Trimethylbenzyl | |
| 2.49 | Me | Me | 4-Chloro-2-nitrobenzyl | |
| 2.50 | Me | Me | 3-Methoxybenzyl | |
| 2.51 | Me | Me | 2-Phenethyl | |
| 2.52 | Me | Me | 3-Phenylpropyl | |
| 2.53 | Me | Me | 2-(4-Nitrophenyl)ethyl | |
| 2.54 | Me | Me | 2-(2-CF₃-Phenyl)ethyl | |
| 2.55 | Me | Me | 2-(4-Methoxyphenyl)ethyl | |
| 2.56 | Me | Me | 2-Chloro-6-fluorobenzyl | |
| 2.57 | Me | Me | 3,4-Methylenedioxybenzyl | |
| 2.58 | Me | Me | 2-Cyanobenzyl | |
| 2.59 | Me | Me | Methoxycarbonyl-methyl | |
| 2.60 | H | Me | Methoxycarbonyl-methyl | |
| 2.61 | Me | Me | 2-(4-Chlorophenyl)ethyl | |
| 2.62 | Me | Me | Cyclopropylmethyl | |
| 2.63 | Me | Me | CH₂CH₂F | |
| 2.64 | Me | CN | Et | |
| 2.65 | Me | CN | t-Butyl | |
| 2.66 | Me | CN | Propargyl | |
| 2.67 | Me | CN | Cyclopropylmethyl | |
| 2.68 | Me | CN | CH₂CH₂F | |
| 2.69 | Me | CN | CH₂CH₂CH₂F | |
| 2.70 | Me | CN | 2,2-Dichlorocyclopropylmethyl | |
| 2.71 | H | CN | Me | |
| 2.72 | CN | CN | Me | |
| 2.73 | Et | CN | Me | |
| 2.74 | Δ | CN | Me | |
| 2.75 | Me | COOMe | Et | |
| 2.76 | Me | COOMe | t-Butyl | |
| 2.77 | Me | COOMe | Propargyl | |
| 2.78 | Me | COOMe | Cyclopropylmethyl | |
| 2.79 | Me | COOMe | CH₂CH₂F | |
| 2.80 | Me | COOMe | CH₂CH₂CH₂CF₃ | |
| 2.81 | Me | COOMe | 2,2-Dichlorocyclopropylmethyl | |
| 2.82 | Me | COOMe | Methoxymethyl | |
| 2.83 | H | COOMe | Me | |
| 2.84 | CN | COOMe | Me | |
| 2.85 | Δ | COOMe | Me | |
| 2.86 | Me | COOEt | Me | |
| 2.87 | Me | COOPropyl | Me | |
| 2.88 | Me | COOC(Me)₃ | Me | |
| 2.89 | Me | COOCH(Me)₂ | Me | |
| 2.90 | Me | COOCH₂-cyclopropyl | Me | |
| 2.91 | Me | COOCH₂CH=CH₂ | Me | |
| 2.92 | Me | COOCH₂C≡CH | Me | |
| 2.93 | Me | COOCH₂CN | Me | |
| 2.94 | Me | COOCH₂CF₃ | Me | |
| 2.95 | Me | COOCH₂CH₂OMe | Me | |
| 2.96 | Me | COOCH₂CH₂SMe | Me | |
| 2.97 | Me | CON(Me)₂ | Me | |
| 2.98 | Me | CON(Me)Et | Me | |
| 2.99 | Me | CON(Et)₂ | Me | |
| 2.100 | Me | CON(Me)Propyl | Me | |
| 2.101 | Me | CON(CH₂CH₂CN)₂ | Me | |
| 2.102 | Me | 2-Δ²-Thiazolinyl | Me | |
| 2.103 | Me | 2-Thiazolyl | Me | |
| 2.104 | Me | 2-Pyridyl | Me | |
| 2.105 | Me | 3-Pyridyl | Me | |
| 2.106 | Me | 4-Pyridyl | Me | |
| 2.107 | Me | 2-Pyrimidinyl | Me | |
| 2.108 | Me | 4-Pyrimidinyl | Me | |
| 2.109 | Me | 2-Pyrazinyl | Me | |
| 2.110 | Me | COOBenzyl | Me | |
| 2.111 | Me | 2-Thienyl | Me | |
| 2.112 | Me | 5-Me-2-Thienyl | Me | |
| 2.113 | Me | 5-Et-2-Thienyl | Me | |
| 2.114 | Me | 2-Furyl | Me | |
| 2.115 | Me | 5-Me-2-Furyl | Me | |
| 2.116 | Me | 5-Et-2-Furyl | Me | |
| 2.117 | Me | 5-Methylthio-2-thienyl | Me | |
| 2.118 | Me | 2-Quinoxalinyl | Me | |
| 2.119 | Me | 2-Benzothiazolyl | Me | |
| 2.120 | Me | 2-Benzo[b]thienyl | Me | |
| 2.121 | Me | 5-Me-3-Isoxazolyl | Me | |
| 2.122 | Me | 4-Me-(1,2,3-Thiadiazol)-5-yl | Me | |
| 2.123 | Me | 1-Me-2-Pyrrolyl | Me | |
| 2.124 | Me | 1-Naphthyl | Me | |
| 2.125 | Me | 2-Naphthyl | Me | |
| 2.126 | Me | 4-Biphenyl | Me | |

TABLE 3

126 compounds No. 3.1 to 3.126 of the formula

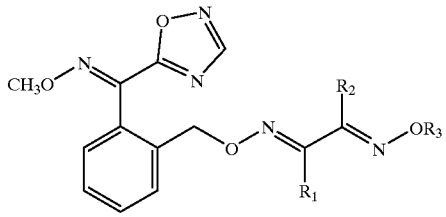

in which
$R_1$, $R_2$ and $R_3$ are as defined for the corresponding compound in Table 1.

TABLE 4

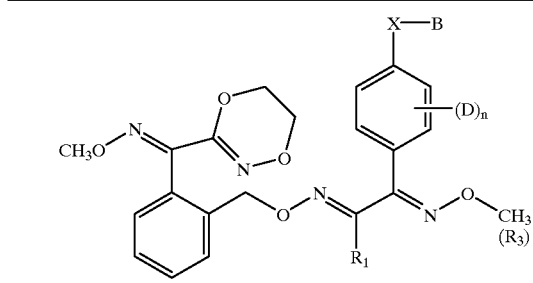

| Example No. | $R_1$ | X* | n | B or D | Physical data (m.p.) |
|---|---|---|---|---|---|
| 4.1 | Me | — | 1 | 2-Me | 112–114° C. |
| 4.2 | Me | — | 1 | 3-Me | resin |
| 4.3 | Me | — | 1 | 4-Me | 153–155° C. |
| 4.4 | Me | — | 1 | 2-CF$_3$ | |
| 4.5 | Me | — | 1 | 3-CF$_3$ | |
| 4.6 | Me | — | 1 | 4-CF$_3$ | 145–147° C. |
| 4.7 | Me | — | 1 | 2-Fluoro | resin |
| 4.8 | Me | — | 1 | 3-Fluoro | |
| 4.9 | Me | — | 1 | 4-Fluoro | |
| 4.10 | Me | — | 1 | 2-Chloro | |
| 4.11 | Me | — | 1 | 3-Chloro | |
| 4.12 | Me | — | 1 | 4-Chloro | |
| 4.13 | Me | — | 1 | 2-Bromo | |
| 4.14 | Me | — | 1 | 3-Bromo | |
| 4.15 | Me | — | 1 | 4-Bromo | |
| 4.16 | Me | — | 1 | 4-Et | resin |
| 4.17 | Me | — | 1 | 4-tert-Butyl | resin |
| 4.18 | Me | — | 2 | 2,3-Dimethyl | |
| 4.19 | Me | — | 2 | 2,4-Dimethyl | resin |
| 4.20 | Me | — | 2 | 2,5-Dimethyl | resin |
| 4.21 | Me | — | 2 | 2-Me,4-F | oil |
| 4.22 | Me | — | 2 | 2-Me,5-F | 120–122° C. |
| 4.23 | Me | — | 2 | 2-F,5-Me | |
| 4.24 | Me | — | 2 | 3-CF$_3$,4-Cl | 155–157° C. |
| 4.25 | Me | — | 2 | 3-CF$_3$-Phenoxy | |
| 4.26 | Me | — | 0 | — | |
| 4.27 | CN | — | 0 | — | |
| 4.28 | Me | — | 2 | 3,4-Methylenedioxy | |
| 4.29 | Me | O | 0 | Me | resin |
| 4.30 | Me | O | 0 | Et | oil |
| 4.31 | Me | O | 0 | n-Propyl | resin |
| 4.32 | Me | O | 0 | i-Propyl | resin |
| 4.33 | Me | O | 0 | Allyl | |
| 4.34 | Me | O | 0 | Propargyl | |
| 4.35 | Me | O | 0 | Phenyl | |
| 4.36 | Me | O | 0 | 3-CF$_3$-Phenyl | |
| 4.37 | Me | O | 0 | 2-Fluorophenyl | |
| 4.38 | Me | O | 0 | 3-Fluorophenyl | |
| 4.39 | Me | O | 0 | 4-Fluorophenyl | 136–138° C. |

TABLE 4-continued

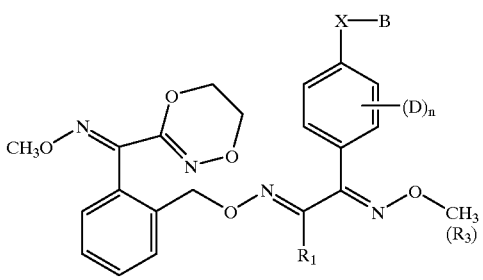

| Example No. | $R_1$ | X* | n | B or D | Physical data (m.p.) |
|---|---|---|---|---|---|
| 4.40 | Me | O | 0 | 4-Chlorophenyl | resin |
| 4.41 | Me | O | 0 | 4-Bromophenyl | |
| 4.42 | Me | O | 0 | CF$_3$ | |
| 4.43 | Me | O | 0 | CHF$_2$ | |
| 4.44 | Me | O | 0 | CF$_2$CHF$_2$ | resin |
| 4.45 | Me | S | 0 | Me | |
| 4.46 | Me | —SO$_2$— | 0 | Me | |
| 4.47 | Me | S | 0 | Et | |
| 4.48 | Me | —SO$_2$— | 0 | Et | |
| 4.49 | Me | S | 0 | n-Propyl | |
| 4.50 | Me | —SO$_2$— | 0 | n-Propyl | resin |
| 4.51 | Me | S | 0 | i-Propyl | |
| 4.52 | Me | S | 0 | Phenyl | |
| 4.53 | Me | S | 0 | 2-Pyridyl | |
| 4.54 | Me | S | 0 | 2-Pyrimidinyl | |
| 4.55 | Me | S | 0 | 5-Me-1,3,4-Thiadiazolyl | |
| 4.56 | Me | —OCH$_2$— | 0 | Phenyl | |
| 4.57 | Me | —OCH$_2$— | 0 | 3-CF$_3$-Phenyl | resin |
| 4.58 | Me | —OCH$_2$— | 0 | 2-CF$_3$-Phenyl | |
| 4.59 | Me | —OCH$_2$— | 0 | 4-CF$_3$-Phenyl | |
| 4.60 | Me | —OCH$_2$— | 0 | 2-F-Phenyl | |
| 4.61 | Me | —OCH$_2$— | 0 | 3-F-Phenyl | |
| 4.62 | Me | —OCH$_2$— | 0 | 4-F-Phenyl | |
| 4.63 | Me | —OCH$_2$— | 0 | 3-Me-Phenyl | |
| 4.64 | Me | OCH$_2$ | 0 | 3-Cl-Phenyl | |
| 4.65 | Me | OCH$_2$ | 0 | 3-Br-Phenyl | |
| 4.66 | Me | OCH$_2$ | 0 | 3-CH$_3$O-Phenyl | |
| 4.67 | Me | —OCH$_2$— | 0 | Trimethylsilyl | |
| 4.68 | Me | —OCH$_2$— | 0 | Cyclohexyl | |
| 4.69 | Me | —OCH$_2$— | 0 | CF$_3$ | |
| 4.70 | Me | O | 0 | 4-Me-phenyl | |
| 4.71 | Me | O | 0 | 3-Cl-phenyl | |
| 4.72 | Me | O | 0 | 3-Br-phenyl | resin |
| 4.73 | Me | — | 2 | 2,4-Di-fluoro | |
| 4.74 | Me | — | 1 | 4-Ethynyl | |
| 4.75 | Me | — | 1 | 4-(3-Methyl-isoxazol-5-yl) | |
| 4.76 | Me | — | 1 | 4-Phenyl | resin |
| 4.77 | Me | — | 1 | 4-(p-Chlorophenyl) | |
| 4.78 | Me | — | 1 | 2-Methoxy | resin |
| 4.79 | Me | — | 1 | 4-Trimethylsilyl | oil |
| 4.80 | Me | O | 0 | n-Butyl | resin |
| 4.81 | Me | O | 0 | s-Butyl | resin |
| 4.82 | Me | O | 0 | i-Butyl | |
| 4.83 | Me | O | 0 | t-Butyl | |
| 4.84 | Me | — | 2 | 2-F,4-Me | 155–158° C. |
| 4.85 | Me | O | 0 | 4-t-Butylphenyl | resin |
| 4.86 | Me | O | 0 | Cyclopentyl | |
| 4.87 | Me | O | 0 | 2,4-Difluorophenyl | |
| 4.88 | Me | O | 0 | 4-F,3-Cl-phenyl | |
| 4.89 | Me | — | 2 | 2-F,4-nPropyloxy | resin |
| 4.90 | Me | — | 2 | 2-F,4-Ethoxy | 113–115° C. |
| 4.91 | Me | — | 2 | 2-Me,4-nPropyloxy | |
| 4.92 | Me | — | 2 | 2-Me,4-Ethoxy | |
| 4.93 | Me | — | 2 | 2-F,4-iPropyloxy | resin |
| 4.94 | Me | — | 2 | 2,4-Dimethoxy | resin |
| 4.95 | Me | — | 2 | 2-F,4-Methoxy | resin |
| 4.96 | Me | — | 2 | 2-F,4-nButyloxy | resin |
| 4.97 | Me | — | 2 | 2-F,4-sButyloxy | |
| 4.98 | Me | — | 2 | 2-F,4-iButyloxy | |

TABLE 4-continued

| Example No. | R₁ | X* | n | B or D | Physical data (m.p.) |
|---|---|---|---|---|---|
| 4.99 | Me | — | 2 | 2-F,4-Cyclopentyloxy | |
| 4.100 | Me | — | 2 | 2-Me,4-Methoxy | |
| 4.101 | Me | — | 2 | 2-Me,4-iPropyloxy | |
| 4.102 | Me | — | 2 | 2-Me,4-nButyloxy | |
| 4.103 | Me | — | 2 | 2-Me,4-sButyloxy | |
| 4.104 | Me | — | 2 | 2-Me,4-iButyloxy | |
| 4.105 | Me | — | 2 | 2-Me,4-Cyclopentyloxy | |
| 4.106 | Me | — | 2 | 2-F,4-(2,2-Dichlorocyclopropylmethoxy) | |
| 4.107 | Me | — | 2 | 2-Me,4-(2,2-Diclorocyclopropylmethoxy) | |
| 4.108 | Me | — | 2 | 2-Methoxy,4-F | resin |
| 4.109 | Me | — | 2 | 2-Methoxy,4-Me | |

TABLE 5

| Example No. | R₁ | X* | n | B or D | Physical data |
|---|---|---|---|---|---|
| 5.1 | Me | — | 1 | 2-Me | m.p. 119° C. |
| 5.2 | Me | — | 1 | 3-Me | |
| 5.3 | Me | — | 1 | 4-Me | |
| 5.4 | Me | — | 1 | 2-CF₃ | |
| 5.5 | Me | — | 1 | 3-CF₃ | |
| 5.6 | Me | — | 1 | 4-CF₃ | m.p. 146° C. |
| 5.7 | Me | — | 1 | 2-Fluoro | |
| 5.8 | Me | — | 1 | 3-Fluoro | |
| 5.9 | Me | — | 1 | 4-Fluoro | |
| 5.10 | Me | — | 1 | 2-Chloro | |
| 5.11 | Me | — | 1 | 3-Chloro | |
| 5.12 | Me | — | 1 | 4-Chloro | |
| 5.13 | Me | — | 1 | 2-Bromo | |
| 5.14 | Me | — | 1 | 3-Bromo | |
| 5.15 | Me | — | 1 | 4-Bromo | |
| 5.16 | Me | — | 1 | 4-Et | |
| 5.17 | Me | — | 1 | 4-tert-Butyl | |
| 5.18 | Me | — | 2 | 2,3-Dimethyl | |
| 5.19 | Me | — | 2 | 2,4-Dimethyl | |
| 5.20 | Me | — | 2 | 2,5-Dimethyl | |
| 5.21 | Me | — | 2 | 2-Me,4-F | |
| 5.22 | Me | — | 2 | 2-Me,5-F | |
| 5.23 | Me | — | 2 | 2-F,5-Me | |
| 5.24 | Me | — | 2 | 3-CF₃,4-Cl | |
| 5.25 | Me | — | 2 | 3-CF₃-Phenoxy | |
| 5.26 | Me | — | 0 | — | |
| 5.27 | CN | — | 0 | — | |
| 5.28 | Me | — | 2 | 3,4-Methylenedioxy | |
| 5.29 | Me | O | 0 | Me | |
| 5.30 | Me | O | 0 | Et | oil |
| 5.31 | Me | O | 0 | n-Propyl | oil |
| 5.32 | Me | O | 0 | i-Propyl | |
| 5.33 | Me | O | 0 | Allyl | |
| 5.34 | Me | O | 0 | Propargyl | |
| 5.35 | Me | O | 0 | Phenyl | |
| 5.36 | Me | O | 0 | 3-CF₃-Phenyl | |
| 5.37 | Me | O | 0 | 2-Fluorophenyl | |
| 5.38 | Me | O | 0 | 3-Fluorophenyl | |
| 5.39 | Me | O | 0 | 4-Fluorophenyl | |
| 5.40 | Me | O | 0 | 4-Chlorophenyl | |
| 5.41 | Me | O | 0 | 4-Bromophenyl | |
| 5.42 | Me | O | 0 | CF₃ | |
| 5.43 | Me | O | 0 | CHF₂ | |
| 5.44 | Me | O | 0 | CF₂CHF₂ | |
| 5.45 | Me | S | 0 | Me | |
| 5.46 | Me | —SO₂— | 0 | Me | |
| 5.47 | Me | S | 0 | Et | |
| 5.48 | Me | —SO₂— | 0 | Et | |
| 5.49 | Me | S | 0 | n-Propyl | |
| 5.50 | Me | —SO₂— | 0 | n-Propyl | |
| 5.51 | Me | S | 0 | i-Propyl | |
| 5.52 | Me | S | 0 | Phenyl | |
| 5.53 | Me | S | 0 | 2-Pyridyl | |
| 5.54 | Me | S | 0 | 2-Pyrimidinyl | |
| 5.55 | Me | S | 0 | 5-Me-1,3,4-Thiadiazolyl | |
| 5.56 | Me | —OCH₂— | 0 | Phenyl | |
| 5.57 | Me | —OCH₂— | 0 | 3-CF₃-Phenyl | m.p. 129° C. |
| 5.58 | Me | —OCH₂— | 0 | 2-CF₃-Phenyl | |
| 5.59 | Me | —OCH₂— | 0 | 4-CF₃-Phenyl | |
| 5.60 | Me | —OCH₂— | 0 | 2-F-Phenyl | |
| 5.61 | Me | —OCH₂— | 0 | 3-F-Phenyl | |
| 5.62 | Me | —OCH₂— | 0 | 4-F-Phenyl | |
| 5.63 | Me | —OCH₂— | 0 | 3-Me-Phenyl | |
| 5.64 | Me | OCH₂ | 0 | 3-Cl-Phenyl | |
| 5.65 | Me | OCH₂ | 0 | 3-Br-Phenyl | |
| 5.66 | Me | OCH₂ | 0 | 3-CH₃O-Phenyl | |
| 5.67 | Me | —OCH₂— | 0 | Trimethylsilyl | |
| 5.68 | Me | —OCH₂— | 0 | Cyclohexyl | |
| 5.69 | Me | —OCH₂— | 0 | CF₃ | |
| 5.70 | Me | O | 0 | 4-Me-phenyl | |
| 5.71 | Me | O | 0 | 3-Cl-phenyl | |
| 5.72 | Me | O | 0 | 3-Br-phenyl | |
| 5.73 | Me | — | 2 | 2,4-Di-fluoro | m.p. 99° C. |
| 5.74 | Me | — | 1 | 4-Ethynyl | |
| 5.75 | Me | — | 1 | 4-(3-Methyl-isoxazol-5-yl) | |
| 5.76 | Me | — | 1 | 4-Phenyl | oil |
| 5.77 | Me | — | 1 | 4-(p-Chlorophenyl) | |
| 5.78 | Me | — | 2 | 2-Methoxy | oil |
| 5.79 | Me | — | 1 | 4-Trimethylsilyl | |
| 5.80 | Me | O | 0 | n-Butyl | |

TABLE 5-continued

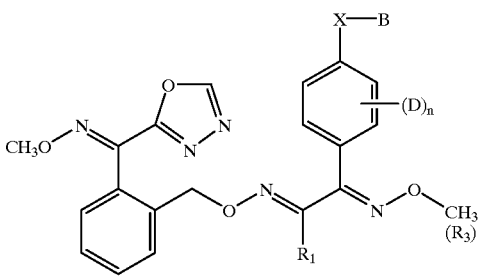

| Example No. | R₁ | X* | n | B or D | Physical data |
|---|---|---|---|---|---|
| 5.81 | Me | O | 0 | s-Butyl | |
| 5.82 | Me | O | 0 | i-Butyl | |
| 5.83 | Me | O | 0 | t-Butyl | |
| 5.84 | Me | — | 2 | 2-F,4-Me | |
| 5.85 | Me | O | 0 | 4-t-Butylphenyl | |
| 5.86 | Me | O | 0 | Cyclopentyl | |
| 5.87 | Me | O | 0 | 2,4-Difluorophenyl | |
| 5.88 | Me | O | 0 | 4-F,3-Cl-phenyl | |
| 5.89 | Me | — | 2 | 2-F,4-nPropyloxy | |
| 5.90 | Me | — | 2 | 2-F,4-Ethoxy | |
| 5.91 | Me | — | 2 | 2-Me,4-nPropyloxy | |
| 5.92 | Me | — | 2 | 2-Me,4-Ethoxy | |
| 5.93 | Me | — | 2 | 2-F,4-iPropyloxy | |
| 5.94 | Me | — | 2 | 2,4-Dimethoxy | |
| 5.95 | Me | — | 2 | 2-F,4-Methoxy | |
| 5.96 | Me | — | 2 | 2-F,4-nButyloxy | |
| 5.97 | Me | — | 2 | 2-F,4-sButyloxy | |
| 5.98 | Me | — | 2 | 2-F,4-iButyloxy | |
| 5.99 | Me | — | 2 | 2-F,4-Cyclopentyloxy | |
| 5.100 | Me | — | 2 | 2-Me,4-Methoxy | |
| 5.101 | Me | — | 2 | 2-Me,4-iPropyloxy | |
| 5.102 | Me | — | 2 | 2-Me,4-nButyloxy | |
| 5.103 | Me | — | 2 | 2-Me,4-sButyloxy | |
| 5.104 | Me | — | 2 | 2-Me,4-iButyloxy | |
| 5.105 | Me | — | 2 | 2-Me,4-Cyclopentyloxy | |
| 5.106 | Me | — | 2 | 2-F,4-(2,2-Dichlorocyclopropylmethoxy) | |
| 5.107 | Me | — | 2 | 2-Me,4-(2,2-Dichlorocyclopropylmethoxy) | |
| 5.108 | Me | — | 2 | 2-Methoxy,4-F | |
| 5.109 | Me | — | 2 | 2-Methoxy,4-Me | |

TABLE 6

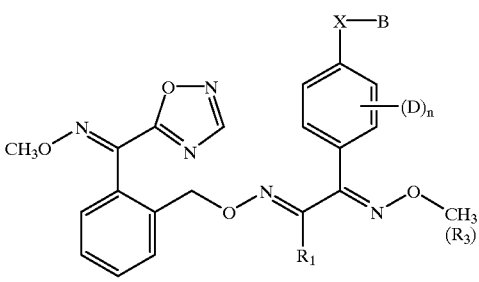

| Example No. | R₁ | X* | n | B or D | Physical data |
|---|---|---|---|---|---|
| 6.1 | Me | — | 1 | 2-Me | |
| 6.2 | Me | — | 1 | 3-Me | |
| 6.3 | Me | — | 1 | 4-Me | |
| 6.4 | Me | — | 1 | 2-CF₃ | |
| 6.5 | Me | — | 1 | 3-CF₃ | |

TABLE 6-continued

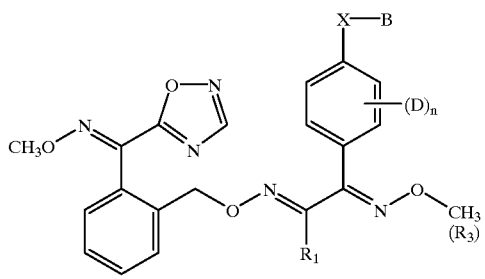

| Example No. | R₁ | X* | n | B or D | Physical data |
|---|---|---|---|---|---|
| 6.6 | Me | — | 1 | 4-CF₃ | |
| 6.7 | Me | — | 1 | 2-Fluoro | |
| 6.8 | Me | — | 1 | 3-Fluoro | |
| 6.9 | Me | — | 1 | 4-Fluoro | |
| 6.10 | Me | — | 1 | 2-Chloro | |
| 6.11 | Me | — | 1 | 3-Chloro | |
| 6.12 | Me | — | 1 | 4-Chloro | |
| 6.13 | Me | — | 1 | 2-Bromo | |
| 6.14 | Me | — | 1 | 3-Bromo | |
| 6.15 | Me | — | 1 | 4-Bromo | |
| 6.16 | Me | — | 1 | 4-Et | |
| 6.17 | Me | — | 1 | 4-tert-Butyl | |
| 6.18 | Me | — | 2 | 2,3-Dimethyl | |
| 6.19 | Me | — | 2 | 2,4-Dimethyl | |
| 6.20 | Me | — | 2 | 2,5-Dimethyl | |
| 6.21 | Me | — | 2 | 2-Me,4-F | |
| 6.22 | Me | — | 2 | 2-Me,5-F | |
| 6.23 | Me | — | 2 | 2-F,5-Me | |
| 6.24 | Me | — | 2 | 3-CF₃,4-Cl | |
| 6.25 | Me | — | 2 | 3-CF₃-Phenoxy | |
| 6.26 | Me | — | 0 | — | |
| 6.27 | CN | — | 0 | — | |
| 6.28 | Me | — | 2 | 3,4-Methylenedioxy | |
| 6.29 | Me | O | 0 | Me | |
| 6.30 | Me | O | 0 | Et | |
| 6.31 | Me | O | 0 | n-Propyl | |
| 6.32 | Me | O | 0 | i-Propyl | |
| 6.33 | Me | O | 0 | Allyl | |
| 6.34 | Me | O | 0 | Propargyl | |
| 6.35 | Me | O | 0 | Phenyl | |
| 6.36 | Me | O | 0 | 3-CF₃-Phenyl | |
| 6.37 | Me | O | 0 | 2-Fluorophenyl | |
| 6.38 | Me | O | 0 | 3-Fluorophenyl | |
| 6.39 | Me | O | 0 | 4-Fluorophenyl | |
| 6.40 | Me | O | 0 | 4-Chlorophenyl | |
| 6.41 | Me | O | 0 | 4-Bromophenyl | |
| 6.42 | Me | O | 0 | CF₃ | |
| 6.43 | Me | O | 0 | CHF₂ | |
| 6.44 | Me | O | 0 | CF₂CHF₂ | |
| 6.45 | Me | S | 0 | Me | |
| 6.46 | Me | —SO₂— | 0 | Me | |
| 6.47 | Me | S | 0 | Et | |
| 6.48 | Me | —SO₂— | 0 | Et | |
| 6.49 | Me | S | 0 | n-Propyl | |
| 6.50 | Me | —SO₂— | 0 | n-Propyl | |
| 6.51 | Me | S | 0 | i-Propyl | |
| 6.52 | Me | S | 0 | Phenyl | |
| 6.53 | Me | S | 0 | 2-Pyridyl | |
| 6.54 | Me | S | 0 | 2-Pyrimidinyl | |
| 6.55 | Me | S | 0 | 5-Me-1,3,4-Thiadiazolyl | |
| 6.56 | Me | —OCH₂— | 0 | Phenyl | |
| 6.57 | Me | —OCH₂— | 0 | 3-CF₃-Phenyl | |
| 6.58 | Me | —OCH₂— | 0 | 2-CF₃-Phenyl | |
| 6.59 | Me | —OCH₂— | 0 | 4-CF₃-Phenyl | |
| 6.60 | Me | —OCH₂— | 0 | 2-F-Phenyl | |
| 6.61 | Me | —OCH₂— | 0 | 3-F-Phenyl | |
| 6.62 | Me | —OCH₂— | 0 | 4-F-Phenyl | |
| 6.63 | Me | —OCH₂— | 0 | 3-Me-Phenyl | |
| 6.64 | Me | OCH₂ | 0 | 3-Cl-Phenyl | |
| 6.65 | Me | OCH₂ | 0 | 3-Br-Phenyl | |

TABLE 6-continued

| Example No. | R₁ | X* | n | B or D | Physical data |
|---|---|---|---|---|---|
| 6.66 | Me | OCH₂ | 0 | 3-CH₃O-Phenyl | |
| 6.67 | Me | —OCH₂— | 0 | Trimethylsilyl | |
| 6.68 | Me | —OCH₂— | 0 | Cyclohexyl | |
| 6.69 | Me | —OCH₂— | 0 | CF₃ | |
| 6.70 | Me | O | 0 | 4-Me-phenyl | |
| 6.71 | Me | O | 0 | 3-Cl-phenyl | |
| 6.72 | Me | O | 0 | 3-Br-phenyl | |
| 6.73 | Me | — | 2 | 2,4-Di-fluoro | resin |
| 6.74 | Me | — | 1 | 4-Ethynyl | |
| 6.75 | Me | — | 1 | 4-(3-Methyl-isoxazol-5-yl) | |
| 6.76 | Me | — | 1 | 4-Phenyl | |
| 6.77 | Me | — | 1 | 4-(p-Chlorophenyl) | |
| 6.78 | Me | — | 1 | 2-Methoxy | |
| 6.79 | Me | — | 1 | 4-Trimethylsilyl | |
| 6.80 | Me | O | 0 | n-Butyl | |
| 6.81 | Me | O | 0 | s-Butyl | |
| 6.82 | Me | O | 0 | i-Butyl | |
| 6.83 | Me | O | 0 | t-Butyl | |
| 6.84 | Me | — | 2 | 2-F,4-Me | |
| 6.85 | Me | O | 0 | 4-t-Butylphenyl | |
| 6.86 | Me | O | 0 | Cyclopentyl | |
| 6.87 | Me | O | 0 | 2,4-Difluorophenyl | |
| 6.88 | Me | O | 0 | 4-F,3-Cl-phenyl | |
| 6.89 | Me | — | 2 | 2-F,4-nPropyloxy | |
| 6.90 | Me | — | 2 | 2-F,4-Ethoxy | |
| 6.91 | Me | — | 2 | 2-Me,4-nPropyloxy | |
| 6.92 | Me | — | 2 | 2-Me,4-Ethoxy | |
| 6.93 | Me | — | 2 | 2-F,4-iPropyloxy | |
| 6.94 | Me | — | 2 | 2,4-Dimethoxy | |
| 6.95 | Me | — | 2 | 2-F,4-Methoxy | |
| 6.96 | Me | — | 2 | 2-F,4-nButyloxy | |
| 6.97 | Me | — | 2 | 2-F,4-sButyloxy | |
| 6.98 | Me | — | 2 | 2-F,4-iButyloxy | |
| 6.99 | Me | — | 2 | 2-F,4-Cyclopentyloxy | |
| 6.100 | Me | — | 2 | 2-Me,4-Methoxy | |
| 6.101 | Me | — | 2 | 2-Me,4-iPropyloxy | |
| 6.102 | Me | — | 2 | 2-Me,4-nButyloxy | |
| 6.103 | Me | — | 2 | 2-Me,4-sButyloxy | |
| 6.104 | Me | — | 2 | 2-Me,4-iButyloxy | |
| 6.105 | Me | — | 2 | 2-Me,4-Cyclopentyloxy | |
| 6.106 | Me | — | 2 | 2-F,4-(2,2-Dichlorocyclopropylmethoxy) | |
| 6.107 | Me | — | 2 | 2-Me,4-(2,2-Dichlorocyclopropylmethoxy) | |
| 6.108 | Me | — | 2 | 2-Methoxy,4-F | |
| 6.109 | Me | — | 2 | 2-Methoxy,4-Me | |

TABLE 7

| Example No. | R₁ | R₃ | R₅ | R₆ | R₇ | R₈ | R₉ | Physical data |
|---|---|---|---|---|---|---|---|---|
| 7.1 | Me | Me | H | H | H | H | H | |
| 7.2 | Me | Me | H | Cl | Cl | H | H | |
| 7.3 | Me | Me | H | Br | Br | H | H | |
| 7.4 | H | Me | H | Br | Br | H | H | |
| 7.5 | Me | Et | H | Br | Br | H | H | |
| 7.6 | Me | Me | Me | F | F | H | H | |
| 7.7 | Me | Me | Me | Cl | Cl | H | H | |
| 7.8 | Me | Me | Me | Br | Br | H | H | |
| 7.9 | Me | Me | H | Cl | Cl | Me | Me | |
| 7.10 | Me | Me | H | Br | Br | Me | Me | |
| 7.11 | Me | Me | H | F | F | H | H | |
| 7.12 | Me | Me | Me | Br | F | H | H | |

TABLE 8

| Example No. | R₁ | R₃ | R₅ | R₆ | R₇ | R₈ | R₉ | Physical data |
|---|---|---|---|---|---|---|---|---|
| 8.1 | Me | Me | H | H | H | H | H | |
| 8.2 | Me | Me | H | Cl | Cl | H | H | |
| 8.3 | Me | Me | H | Br | Br | H | H | |
| 8.4 | H | Me | H | Br | Br | H | H | |
| 8.5 | Me | Et | H | Br | Br | H | H | |
| 8.6 | Me | Me | Me | F | F | H | H | |
| 8.7 | Me | Me | Me | Cl | Cl | H | H | |
| 8.8 | Me | Me | Me | Br | Br | H | H | |
| 8.9 | Me | Me | H | Cl | Cl | Me | Me | |
| 8.10 | Me | Me | H | Br | Br | Me | Me | |
| 8.11 | Me | Me | H | F | F | H | H | |
| 8.12 | Me | Me | Me | Br | F | H | H | |

TABLE 9

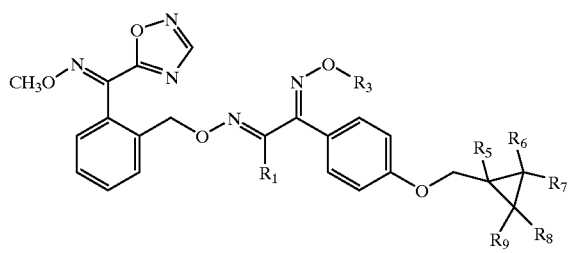

| Example No. | $R_1$ | $R_3$ | $R_5$ | $R_6$ | $R_7$ | $R_8$ | $R_9$ | Physical data |
|---|---|---|---|---|---|---|---|---|
| 9.1 | Me | Me | H | H | H | H | H | |
| 9.2 | Me | Me | H | Cl | Cl | H | H | |
| 9.3 | Me | Me | H | Br | Br | H | H | |
| 9.4 | H | Me | H | Br | Br | H | H | |
| 9.5 | Me | Et | H | Br | Br | H | H | |
| 9.6 | Me | Me | Me | F | F | H | H | |
| 9.7 | Me | Me | Me | Cl | Cl | H | H | |
| 9.8 | Me | Me | Me | Br | Br | H | H | |
| 9.9 | Me | Me | H | Cl | Cl | Me | Me | |
| 9.10 | Me | Me | H | Br | Br | Me | Me | |
| 9.11 | Me | Me | H | F | F | H | H | |
| 9.12 | Me | Me | Me | Br | F | H | H | |

TABLE 10

126 compounds No. 10.1 to 10.126 of the formula

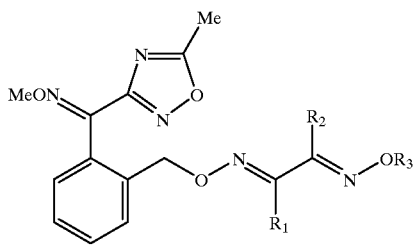

in which
$R_1$, $R_2$ and $R_3$ are as defined for the corresponding compound of Table 1.

TABLE 11

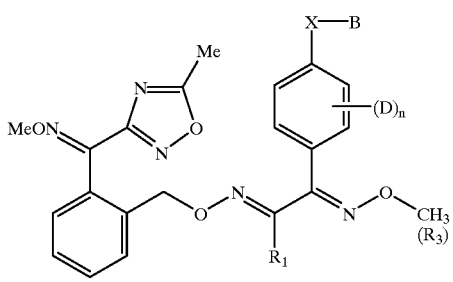

| Example No. | $R_1$ | X* | n | B or D | Physical data |
|---|---|---|---|---|---|
| 11.1 | Me | — | 1 | 2-Me | |
| 11.2 | Me | — | 1 | 3-Me | |
| 11.3 | Me | — | 1 | 4-Me | |
| 11.4 | Me | — | 1 | 2-CF$_3$ | |

TABLE 11-continued

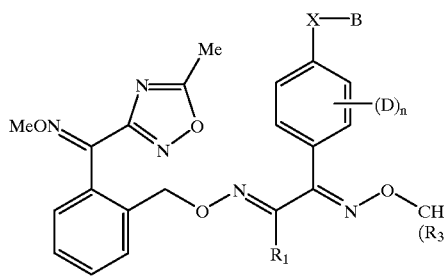

| Example No. | $R_1$ | X* | n | B or D | Physical data |
|---|---|---|---|---|---|
| 11.5 | Me | — | 1 | 3-CF$_3$ | |
| 11.6 | Me | — | 1 | 4-CF$_3$ | |
| 11.7 | Me | — | 1 | 2-Fluoro | |
| 11.8 | Me | — | 1 | 3-Fluoro | |
| 11.9 | Me | — | 1 | 4-Fluoro | |
| 11.10 | Me | — | 1 | 2-Chloro | |
| 11.11 | Me | — | 1 | 3-Chloro | |
| 11.12 | Me | — | 1 | 4-Chloro | |
| 11.13 | Me | — | 1 | 2-Bromo | |
| 11.14 | Me | — | 1 | 3-Bromo | |
| 11.15 | Me | — | 1 | 4-Bromo | |
| 11.16 | Me | — | 1 | 4-Et | |
| 11.17 | Me | — | 1 | 4-tert-Butyl | |
| 11.18 | Me | — | 2 | 2,3-Dimethyl | |
| 11.19 | Me | — | 2 | 2,4-Dimethyl | |
| 11.20 | Me | — | 2 | 2,5-Dimethyl | |
| 11.21 | Me | — | 2 | 2-Me,4-F | |
| 11.22 | Me | — | 2 | 2-Me,5-F | |
| 11.23 | Me | — | 2 | 2-F,5-Me | |
| 11.24 | Me | — | 2 | 3-CF$_3$,4-Cl | |
| 11.25 | Me | — | 2 | 3-CF$_3$-Phenoxy | |
| 11.26 | Me | — | 0 | — | |
| 11.27 | CN | — | 0 | — | |
| 11.28 | Me | — | 2 | 3,4-Methylenedioxy | |
| 11.29 | Me | O | 0 | Me | |
| 11.30 | Me | O | 0 | Et | |
| 11.31 | Me | O | 0 | n-Propyl | |
| 11.32 | Me | O | 0 | i-Propyl | |
| 11.33 | Me | O | 0 | Allyl | |
| 11.34 | Me | O | 0 | Propargyl | |
| 11.35 | Me | O | 0 | Phenyl | |
| 11.36 | Me | O | 0 | 3-CF$_3$-Phenyl | |
| 11.37 | Me | O | 0 | 2-Fluorophenyl | |
| 11.38 | Me | O | 0 | 3-Fluorophenyl | |
| 11.39 | Me | O | 0 | 4-Fluorophenyl | |
| 11.40 | Me | O | 0 | 4-Chlorophenyl | |
| 11.41 | Me | O | 0 | 4-Bromophenyl | |
| 11.42 | Me | O | 0 | CF$_3$ | |
| 11.43 | Me | O | 0 | CHF$_2$ | |
| 11.44 | Me | O | 0 | CF$_2$CHF$_2$ | |
| 11.45 | Me | S | 0 | Me | |
| 11.46 | Me | —SO$_2$— | 0 | Me | |
| 11.47 | Me | S | 0 | Et | |
| 11.48 | Me | —SO$_2$— | 0 | Et | |
| 11.49 | Me | S | 0 | n-Propyl | |
| 11.50 | Me | —SO$_2$— | 0 | n-Propyl | |
| 11.51 | Me | S | 0 | i-Propyl | |
| 11.52 | Me | S | 0 | Phenyl | |
| 11.53 | Me | S | 0 | 2-Pyridyl | |
| 11.54 | Me | S | 0 | 2-Pyrimidinyl | |
| 11.55 | Me | S | 0 | 5-Me-1,3,4-Thiadiazolyl | |
| 11.56 | Me | —OCH$_2$— | 0 | Phenyl | |
| 11.57 | Me | —OCH$_2$— | 0 | 3-CF$_3$-Phenyl | |
| 11.58 | Me | —OCH$_2$— | 0 | 2-CF$_3$-Phenyl | |
| 11.59 | Me | —OCH$_2$— | 0 | 4-CF$_3$-Phenyl | |
| 11.60 | Me | —OCH$_2$— | 0 | 2-F-Phenyl | |
| 11.61 | Me | —OCH$_2$— | 0 | 3-F-Phenyl | |
| 11.62 | Me | —OCH$_2$— | 0 | 4-F-Phenyl | |
| 11.63 | Me | —OCH$_2$— | 0 | 3-Me-Phenyl | |
| 11.64 | Me | OCH$_2$ | 0 | 3-Cl-Phenyl | |

TABLE 11-continued

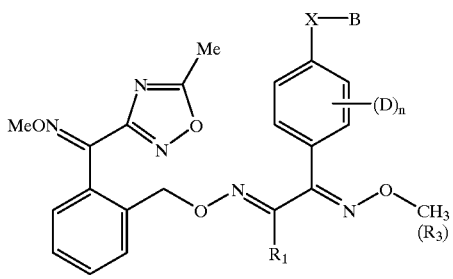

| Example No. | R₁ | X* | n | B or D | Physical data |
|---|---|---|---|---|---|
| 11.65 | Me | OCH₂ | 0 | 3-Br-Phenyl | |
| 11.66 | Me | OCH₂ | 0 | 3-CH₃O-Phenyl | |
| 11.67 | Me | —OCH₂— | 0 | Trimethylsilyl | |
| 11.68 | Me | —OCH₂— | 0 | Cyclohexyl | |
| 11.69 | Me | —OCH₂— | 0 | CF₃ | |
| 11.70 | Me | O | 0 | 4-Me-phenyl | |
| 11.71 | Me | O | 0 | 3-Cl-phenyl | |
| 11.72 | Me | O | 0 | 3-Br-phenyl | |
| 11.73 | Me | — | 2 | 2,4-Di-fluoro | oil |
| 11.74 | Me | — | 1 | 4-Ethinyl | |
| 11.75 | Me | — | 1 | 4-(3-Methyl-isoxazol-5-yl) | |
| 11.76 | Me | — | 1 | 4-Phenyl | |
| 11.77 | Me | — | 1 | 4-(p-Chlorophenyl) | |

TABLE 12

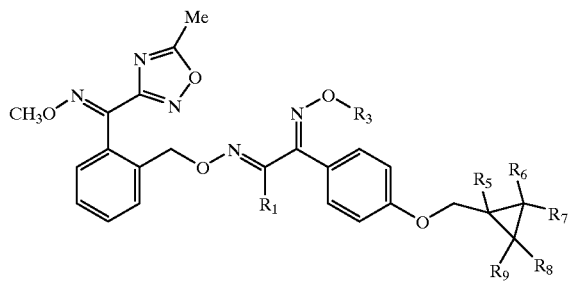

| Example No. | R₁ | R₃ | R₅ | R₆ | R₇ | R₈ | R₉ | Physical data |
|---|---|---|---|---|---|---|---|---|
| 12.1 | Me | Me | H | H | H | H | H | |
| 12.2 | Me | Me | H | Cl | Cl | H | H | |
| 12.3 | Me | Me | H | Br | Br | H | H | |
| 12.4 | H | Me | H | Br | Br | H | H | |
| 12.5 | Me | Et | H | Br | Br | H | H | |
| 12.6 | Me | Me | Me | F | F | H | H | |
| 12.7 | Me | Me | Me | Cl | Cl | H | H | |
| 12.8 | Me | Me | Me | Br | Br | H | H | |
| 12.9 | Me | Me | H | Cl | Cl | Me | Me | |
| 12.10 | Me | Me | H | Br | Br | Me | Me | |
| 12.11 | Me | Me | H | F | F | H | H | |
| 12.12 | Me | Me | Me | Br | F | H | H | |

TABLE 13

126 compounds No 13.1 to 13.126 of the formula

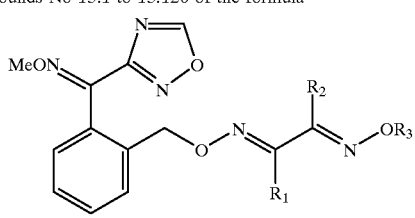

in which
R₁, R₂ and R₃ are as defined for the corresponding compound of Table 1.

TABLE 14

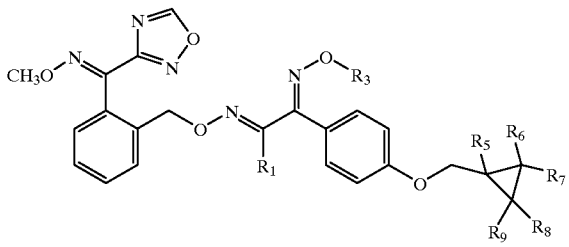

| Example No. | R₁ | R₃ | R₅ | R₆ | R₇ | R₈ | R₉ | Physical data |
|---|---|---|---|---|---|---|---|---|
| 14.1 | Me | Me | H | H | H | H | H | |
| 14.2 | Me | Me | H | Cl | Cl | H | H | |
| 14.3 | Me | Me | H | Br | Br | H | H | |
| 14.4 | H | Me | H | Br | Br | H | H | |
| 14.5 | Me | Et | H | Br | Br | H | H | |
| 14.6 | Me | Me | Me | F | F | H | H | |
| 14.7 | Me | Me | Me | Cl | Cl | H | H | |
| 14.8 | Me | Me | Me | Br | Br | H | H | |
| 14.9 | Me | Me | H | Cl | Cl | Me | Me | |
| 14.10 | Me | Me | H | Br | Br | Me | Me | |
| 14.11 | Me | Me | H | F | F | H | H | |
| 14.12 | Me | Me | Me | Br | F | H | H | |

TABLE 15

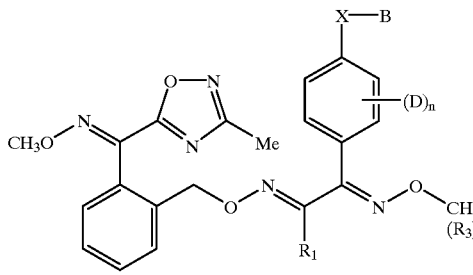

| Example No. | R₁ | X* | n | B or D | Physical data (m.p.) |
|---|---|---|---|---|---|
| 15.1 | Me | — | 1 | 2-Me | |
| 15.2 | Me | — | 1 | 3-Me | |
| 15.3 | Me | — | 1 | 4-Me | |
| 15.4 | Me | — | 1 | 2-CF₃ | |
| 15.5 | Me | — | 1 | 3-CF₃ | |
| 15.6 | Me | — | 1 | 4-CF₃ | |

TABLE 15-continued

| Example No. | R₁ | X* | n | B or D | Physical data (m.p.) |
|---|---|---|---|---|---|
| 15.7 | Me | — | 1 | 2-Fluoro | |
| 15.8 | Me | — | 1 | 3-Fluoro | |
| 15.9 | Me | — | 1 | 4-Fluoro | |
| 15.10 | Me | — | 1 | 2-Chloro | |
| 15.11 | Me | — | 1 | 3-Chloro | |
| 15.12 | Me | — | 1 | 4-Chloro | |
| 15.13 | Me | — | 1 | 2-Bromo | |
| 15.14 | Me | — | 1 | 3-Bromo | |
| 15.15 | Me | — | 1 | 4-Bromo | |
| 15.16 | Me | — | 1 | 4-Et | |
| 15.17 | Me | — | 1 | 4-tert-Butyl | |
| 15.18 | Me | — | 2 | 2,3-Dimethyl | |
| 15.19 | Me | — | 2 | 2,4-Dimethyl | |
| 15.20 | Me | — | 2 | 2,5-Dimethyl | |
| 15.21 | Me | — | 2 | 2-Me,4-F | |
| 15.22 | Me | — | 2 | 2-Me,5-F | |
| 15.23 | Me | — | 2 | 2-F,5-Me | |
| 15.24 | Me | — | 2 | 3-CF₃,4-Cl | |
| 15.25 | Me | — | 2 | 3-CF₃-Phenoxy | |
| 15.26 | Me | — | 0 | — | |
| 15.27 | CN | — | 0 | — | |
| 15.28 | Me | — | 2 | 3,4-Methylenedioxy | |
| 15.29 | Me | O | 0 | Me | |
| 15.30 | Me | O | 0 | Et | |
| 15.31 | Me | O | 0 | n-Propyl | |
| 15.32 | Me | O | 0 | i-Propyl | |
| 15.33 | Me | O | 0 | Allyl | |
| 15.34 | Me | O | 0 | Propargyl | |
| 15.35 | Me | O | 0 | Phenyl | |
| 15.36 | Me | O | 0 | 3-CF₃-Phenyl | |
| 15.37 | Me | O | 0 | 2-Fluorophenyl | |
| 15.38 | Me | O | 0 | 3-Fluorophenyl | |
| 15.39 | Me | O | 0 | 4-Fluorophenyl | |
| 15.40 | Me | O | 0 | 4-Chlorophenyl | |
| 15.41 | Me | O | 0 | 4-Bromophenyl | |
| 15.42 | Me | O | 0 | CF₃ | |
| 15.43 | Me | O | 0 | CHF₂ | |
| 15.44 | Me | O | 0 | CF₂CHF₂ | |
| 15.45 | Me | S | 0 | Me | |
| 15.46 | Me | —SO₂— | 0 | Me | |
| 15.47 | Me | S | 0 | Et | |
| 15.48 | Me | —SO₂— | 0 | Et | |
| 15.49 | Me | S | 0 | n-Propyl | |
| 15.50 | Me | —SO₂— | 0 | n-Propyl | |
| 15.51 | Me | S | 0 | i-Propyl | |
| 15.52 | Me | S | 0 | Phenyl | |
| 15.53 | Me | S | 0 | 2-Pyridyl | |
| 15.54 | Me | S | 0 | 2-Pyrimidinyl | |
| 15.55 | Me | S | 0 | 5-Me-1,3,4-Thiadiazolyl | |
| 15.56 | Me | —OCH₂— | 0 | Phenyl | |
| 15.57 | Me | —OCH₂— | 0 | 3-CF₃-Phenyl | |
| 15.58 | Me | —OCH₂— | 0 | 2-CF₃-Phenyl | |
| 15.59 | Me | —OCH₂— | 0 | 4-CF₃-Phenyl | |
| 15.60 | Me | —OCH₂— | 0 | 2-F-Phenyl | |
| 15.61 | Me | —OCH₂— | 0 | 3-F-Phenyl | |
| 15.62 | Me | —OCH₂— | 0 | 4-F-Phenyl | |
| 15.63 | Me | —OCH₂— | 0 | 3-Me-Phenyl | |
| 15.64 | Me | OCH₂ | 0 | 3-Cl-Phenyl | |
| 15.65 | Me | OCH₂ | 0 | 3-Br-Phenyl | |
| 15.66 | Me | OCH₂ | 0 | 3-CH₃O-Phenyl | |
| 15.67 | Me | —OCH₂— | 0 | Trimethylsilyl | |
| 15.68 | Me | —OCH₂— | 0 | Cyclohexyl | |
| 15.69 | Me | —OCH₂— | 0 | CF₃ | |
| 15.70 | Me | O | 0 | 4-Me-phenyl | |
| 15.71 | Me | O | 0 | 3-Cl-phenyl | |
| 15.72 | Me | O | 0 | 3-Br-phenyl | |
| 15.73 | Me | — | 2 | 2,4-Di-fluoro | 93–94° C. |
| 15.74 | Me | — | 1 | 4-Ethynyl | |
| 15.75 | Me | — | 1 | 4-(3-Methyl-isoxazol-5-yl) | |
| 15.76 | Me | — | 1 | 4-Phenyl | |
| 15.77 | Me | — | 1 | 4-(p-Chlorophenyl) | |
| 15.78 | Me | — | 1 | 2-Methoxy | |
| 15.79 | Me | — | 1 | 4-Trimethylsilyl | |
| 15.80 | Me | O | 0 | n-Butyl | |
| 15.81 | Me | O | 0 | s-Butyl | |
| 15.82 | Me | O | 0 | i-Butyl | |
| 15.83 | Me | O | 0 | t-Butyl | |
| 15.84 | Me | — | 2 | 2-F,4-Me | |
| 15.85 | Me | O | 0 | 4-t-Butylphenyl | |
| 15.86 | Me | O | 0 | Cyclopentyl | |
| 15.87 | Me | O | 0 | 2,4-Difluorophenyl | |
| 15.88 | Me | O | 0 | 4-F,3-Cl-phenyl | |
| 15.89 | Me | — | 2 | 2-F,4-nPropyloxy | |
| 15.90 | Me | — | 2 | 2-F,4-Ethoxy | |
| 15.91 | Me | — | 2 | 2-Me,4-nPropyloxy | |
| 15.92 | Me | — | 2 | 2-Me,4-Ethoxy | |
| 15.93 | Me | — | 2 | 2-F,4-iPropyloxy | |
| 15.94 | Me | — | 2 | 2,4-Dimethoxy | |
| 15.95 | Me | — | 2 | 2-F,4-Methoxy | |
| 15.96 | Me | — | 2 | 2-F,4-nButyloxy | |
| 15.97 | Me | — | 2 | 2-F,4-sButyloxy | |
| 15.98 | Me | — | 2 | 2-F,4-iButyloxy | |
| 15.99 | Me | — | 2 | 2-F,4-Cyclopentyloxy | |
| 15.100 | Me | — | 2 | 2-Me,4-Methoxy | |
| 15.101 | Me | — | 2 | 2-Me,4-iPropyloxy | |
| 15.102 | Me | — | 2 | 2-Me,4-nButyloxy | |
| 15.103 | Me | — | 2 | 2-Me,4-sButyloxy | |
| 15.104 | Me | — | 2 | 2-Me,4-iButyloxy | |
| 15.105 | Me | — | 2 | 2-Me,4-Cyclopentyloxy | |
| 15.106 | Me | — | 2 | 2-F,4-(2,2-Dichlorocyclopropylmethoxy) | |
| 15.107 | Me | — | 2 | 2-Me,4-(2,2-Dichlorocyclopropylmethoxy) | |
| 15.108 | Me | — | 2 | 2-Methoxy,4-F | |
| 15.109 | Me | — | 2 | 2-Methoxy,4-Me | |

TABLE 16

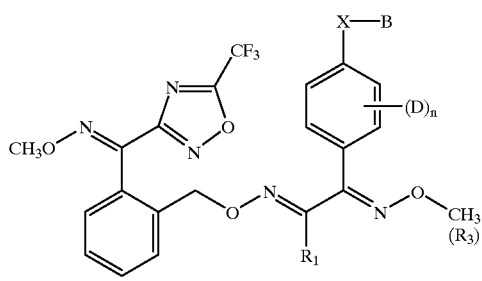

| Example No. | R₁ | X* | n | B or D | Physical data |
|---|---|---|---|---|---|
| 16.1 | Me | — | 1 | 2-Me | |
| 16.2 | Me | — | 1 | 3-Me | |
| 16.3 | Me | — | 1 | 4-Me | |
| 16.4 | Me | — | 1 | 2-CF₃ | |
| 16.5 | Me | — | 1 | 3-CF₃ | |
| 16.6 | Me | — | 1 | 4-CF₃ | |
| 16.7 | Me | — | 1 | 2-Fluoro | |
| 16.8 | Me | — | 1 | 3-Fluoro | |
| 16.9 | Me | — | 1 | 4-Fluoro | |
| 16.10 | Me | — | 1 | 2-Chloro | |
| 16.11 | Me | — | 1 | 3-Chloro | |
| 16.12 | Me | — | 1 | 4-Chloro | |
| 16.13 | Me | — | 1 | 2-Bromo | |
| 16.14 | Me | — | 1 | 3-Bromo | |
| 16.15 | Me | — | 1 | 4-Bromo | |
| 16.16 | Me | — | 1 | 4-Et | |
| 16.17 | Me | — | 1 | 4-tert-Butyl | |
| 16.18 | Me | — | 2 | 2,3-Dimethyl | |
| 16.19 | Me | — | 2 | 2,4-Dimethyl | |
| 16.20 | Me | — | 2 | 2,5-Dimethyl | |
| 16.21 | Me | — | 2 | 2-Me,4-F | |
| 16.22 | Me | — | 2 | 2-Me,5-F | |
| 16.23 | Me | — | 2 | 2-F,5-Me | |
| 16.24 | Me | — | 2 | 3-CF₃,4-Cl | |
| 16.25 | Me | — | 2 | 3-CF₃-Phenoxy | |
| 16.26 | Me | — | 0 | — | |
| 16.27 | CN | — | 0 | | |
| 16.28 | Me | — | 2 | 3,4-Methylenedioxy | |
| 16.29 | Me | O | 0 | Me | |
| 16.30 | Me | O | 0 | Et | |
| 16.31 | Me | O | 0 | n-Propyl | |
| 16.32 | Me | O | 0 | i-Propyl | |
| 16.33 | Me | O | 0 | Allyl | |
| 16.34 | Me | O | 0 | Propargyl | |
| 16.35 | Me | O | 0 | Phenyl | |
| 16.36 | Me | O | 0 | 3-CF₃-Phenyl | |
| 16.37 | Me | O | 0 | 2-Fluorophenyl | |
| 16.38 | Me | O | 0 | 3-Fluorophenyl | |
| 16.39 | Me | O | 0 | 4-Fluorophenyl | |
| 16.40 | Me | O | 0 | 4-Chlorophenyl | |
| 16.41 | Me | O | 0 | 4-Bromophenyl | |
| 16.42 | Me | O | 0 | CF₃ | |
| 16.43 | Me | O | 0 | CHF₂ | |
| 16.44 | Me | O | 0 | CF₂CHF₂ | |
| 16.45 | Me | S | 0 | Me | |
| 16.46 | Me | —SO₂— | 0 | Me | |
| 16.47 | Me | S | 0 | Et | |
| 16.48 | Me | —SO₂— | 0 | Et | |
| 16.49 | Me | S | 0 | n-Propyl | |
| 16.50 | Me | —SO₂— | 0 | n-Propyl | |
| 16.51 | Me | S | 0 | i-Propyl | |
| 16.52 | Me | S | 0 | Phenyl | |
| 16.53 | Me | S | 0 | 2-Pyridyl | |
| 16.54 | Me | S | 0 | 2-Pyrimidinyl | |
| 16.55 | Me | S | 0 | 5-Me-1,3,4-Thiadiazolyl | |
| 16.56 | Me | —OCH₂— | 0 | Phenyl | |
| 16.57 | Me | —OCH₂— | 0 | 3-CF₃-Phenyl | |
| 16.58 | Me | —OCH₂— | 0 | 2-CF₃-Phenyl | |
| 16.59 | Me | —OCH₂— | 0 | 4-CF₃-Phenyl | |
| 16.60 | Me | —OCH₂— | 0 | 2-F-Phenyl | |

TABLE 16-continued

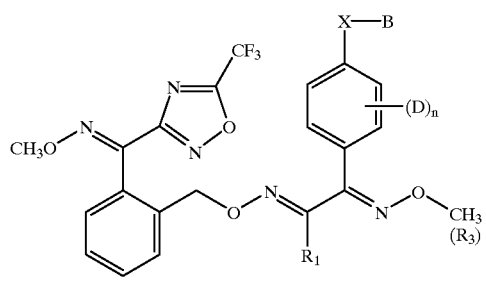

| Example No. | R₁ | X* | n | B or D | Physical data |
|---|---|---|---|---|---|
| 16.61 | Me | —OCH₂— | 0 | 3-F-Phenyl | |
| 16.62 | Me | —OCH₂— | 0 | 4-F-Phenyl | |
| 16.63 | Me | —OCH₂— | 0 | 3-Me-Phenyl | |
| 16.64 | Me | OCH₂ | 0 | 3-Cl-Phenyl | |
| 16.65 | Me | OCH₂ | 0 | 3-Br-Phenyl | |
| 16.66 | Me | OCH₂ | 0 | 3-CH₃O-Phenyl | |
| 16.67 | Me | —OCH₂— | 0 | Trimethylsilyl | |
| 16.68 | Me | —OCH₂— | 0 | Cyclohexyl | |
| 16.69 | Me | —OCH₂— | 0 | CF₃ | |
| 16.70 | Me | O | 0 | 4-Me-phenyl | |
| 16.71 | Me | O | 0 | 3-Cl-phenyl | |
| 16.72 | Me | O | 0 | 3-Br-phenyl | |
| 16.73 | Me | — | 2 | 2,4-Di-fluoro | oil |
| 16.74 | Me | — | 1 | 4-Ethynyl | |
| 16.75 | Me | — | 1 | 4-(3-Methyl-isoxazol-5-yl) | |
| 16.76 | Me | — | 1 | 4-Phenyl | |
| 16.77 | Me | — | 1 | 4-(p-Chlorophenyl) | |
| 16.78 | Me | — | 1 | 2-Methoxy | |
| 16.79 | Me | — | 1 | 3-Methoxy | |
| 16.80 | Me | — | 2 | 3,5-Dimethoxy | |
| 16.81 | Me | — | 2 | 2,4-Dimethoxy | |
| 16.82 | Me | — | 3 | 3,4,5-Trimethoxy | |

TABLE 17

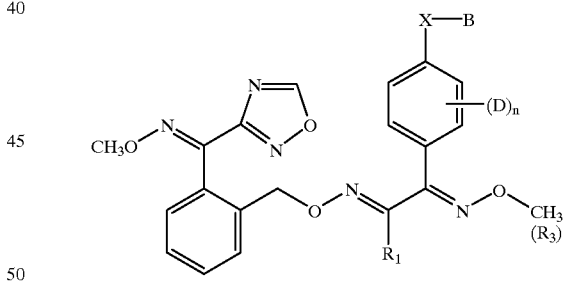

| Example No. | R₁ | X* | n | B or D | Physical data |
|---|---|---|---|---|---|
| 17.1 | Me | — | 1 | 2-Me | |
| 17.2 | Me | — | 1 | 3-Me | |
| 17.3 | Me | — | 1 | 4-Me | |
| 17.4 | Me | — | 1 | 2-CF₃ | |
| 17.5 | Me | — | 1 | 3-CF₃ | |
| 17.6 | Me | — | 1 | 4-CF₃ | |
| 17.7 | Me | — | 1 | 2-Fluoro | |
| 17.8 | Me | — | 1 | 3-Fluoro | |
| 17.9 | Me | — | 1 | 4-Fluoro | |
| 17.10 | Me | — | 1 | 2-Chloro | |
| 17.11 | Me | — | 1 | 3-Chloro | |
| 17.12 | Me | — | 1 | 4-Chloro | |
| 17.13 | Me | — | 1 | 2-Bromo | |
| 17.14 | Me | — | 1 | 3-Bromo | |
| 17.15 | Me | — | 1 | 4-Bromo | |

TABLE 17-continued

[Structure: CH3O-N= group attached to 1,2,4-oxadiazole, linked via benzyl-O-N=C(R1)-C(=N-OCH3)-phenyl(D)n-X-B]

| Example No. | R₁ | X* | n | B or D | Physical data |
|---|---|---|---|---|---|
| 17.16 | Me | — | 1 | 4-Et | |
| 17.17 | Me | — | 1 | 4-tert-Butyl | |
| 17.18 | Me | — | 2 | 2,3-Dimethyl | |
| 17.19 | Me | — | 2 | 2,4-Dimethyl | |
| 17.20 | Me | — | 2 | 2,5-Dimethyl | |
| 17.21 | Me | — | 2 | 2-Me,4-F | |
| 17.22 | Me | — | 2 | 2-Me,5-F | |
| 17.23 | Me | — | 2 | 2-F,5-Me | |
| 17.24 | Me | — | 2 | 3-CF₃,4-Cl | |
| 17.25 | Me | — | 2 | 3-CF₃-Phenoxy | |
| 17.26 | Me | — | 0 | — | |
| 17.27 | CN | — | 0 | — | |
| 17.28 | Me | — | 2 | 3,4-Methylenedioxy | |
| 17.29 | Me | O | 0 | Me | |
| 17.30 | Me | O | 0 | Et | |
| 17.31 | Me | O | 0 | n-Propyl | |
| 17.32 | Me | O | 0 | i-Propyl | |
| 17.33 | Me | O | 0 | Allyl | |
| 17.34 | Me | O | 0 | Propargyl | |
| 17.35 | Me | O | 0 | Phenyl | |
| 17.36 | Me | O | 0 | 3-CF₃-Phenyl | |
| 17.37 | Me | O | 0 | 2-Fluorophenyl | |
| 17.38 | Me | O | 0 | 3-Fluorophenyl | |
| 17.39 | Me | O | 0 | 4-Fluorophenyl | |
| 17.40 | Me | O | 0 | 4-Chlorophenyl | |
| 17.41 | Me | O | 0 | 4-Bromophenyl | |
| 17.42 | Me | O | 0 | CF₃ | |
| 17.43 | Me | O | 0 | CHF₂ | |
| 17.44 | Me | O | 0 | CF₂CHF₂ | |
| 17.45 | Me | S | 0 | Me | |
| 17.46 | Me | —SO₂— | 0 | Me | |
| 17.47 | Me | S | 0 | Et | |
| 17.48 | Me | —SO₂— | 0 | Et | |
| 17.49 | Me | S | 0 | n-Propyl | |
| 17.50 | Me | —SO₂— | 0 | n-Propyl | |
| 17.51 | Me | S | 0 | i-Propyl | |
| 17.52 | Me | S | 0 | Phenyl | |
| 17.53 | Me | S | 0 | 2-Pyridyl | |
| 17.54 | Me | S | 0 | 2-Pyrimidinyl | |
| 17.55 | Me | S | 0 | 5-Me-1,3,4-Thiadiazolyl | |
| 17.56 | Me | —OCH₂— | 0 | Phenyl | |
| 17.57 | Me | —OCH₂— | 0 | 3-CF₃-Phenyl | |
| 17.58 | Me | —OCH₂— | 0 | 2-CF₃-Phenyl | |
| 17.59 | Me | —OCH₂— | 0 | 4-CF₃-Phenyl | |
| 17.60 | Me | —OCH₂— | 0 | 2-F-Phenyl | |
| 17.61 | Me | —OCH₂— | 0 | 3-F-Phenyl | |
| 17.62 | Me | —OCH₂— | 0 | 4-F-Phenyl | |
| 17.63 | Me | —OCH₂— | 0 | 3-Me-Phenyl | |
| 17.64 | Me | OCH₂ | 0 | 3-Cl-Phenyl | |
| 17.65 | Me | OCH₂ | 0 | 3-Br-Phenyl | |
| 17.66 | Me | OCH₂ | 0 | 3-CH₃O-Phenyl | |
| 17.67 | Me | —OCH₂— | 0 | Trimethylsilyl | |
| 17.68 | Me | —OCH₂— | 0 | Cyclohexyl | |
| 17.69 | Me | —OCH₂— | 0 | CF₃ | |
| 17.70 | Me | O | 0 | 4-Me-phenyl | |
| 17.71 | Me | O | 0 | 3-Cl-phenyl | |
| 17.72 | Me | O | 0 | 3-Br-phenyl | |
| 17.73 | Me | — | 2 | 2,4-Di-fluoro | oil |
| 17.74 | Me | — | 1 | 4-Ethynyl | |
| 17.75 | Me | — | 1 | 4-(3-Methyl-isoxazol-5-yl) | |
| 17.76 | Me | — | 1 | 4-Phenyl | |
| 17.77 | Me | — | 1 | 4-(p-Chlorophenyl) | |
| 17.78 | Me | — | 1 | 2-Methoxy | |
| 17.79 | Me | — | 1 | 3-Methoxy | |
| 17.80 | Me | — | 2 | 3,5-Dimethoxy | |
| 17.81 | Me | — | 2 | 2,4-Dimethoxy | |
| 17.82 | Me | — | 3 | 3,4,5-Trimethoxy | |

TABLE 18

[Structure: CH3O-N= group attached to 1,3,4-oxadiazole, linked via benzyl-O-N=C(R1)-C(=N-OCH2CH3)-phenyl(D)n-X-B]

| Example No. | R₁ | X* | n | B or D | Physical data |
|---|---|---|---|---|---|
| 18.1 | Me | — | 1 | 2-Me | |
| 18.2 | Me | — | 1 | 3-Me | |
| 18.3 | Me | — | 1 | 4-Me | |
| 18.4 | Me | — | 1 | 2-CF₃ | |
| 18.5 | Me | — | 1 | 3-CF₃ | |
| 18.6 | Me | — | 1 | 4-CF₃ | |
| 18.7 | Me | — | 1 | 2-Fluoro | |
| 18.8 | Me | — | 1 | 3-Fluoro | |
| 18.9 | Me | — | 1 | 4-Fluoro | |
| 18.10 | Me | — | 1 | 2-Chloro | |
| 18.11 | Me | — | 1 | 3-Chloro | |
| 18.12 | Me | — | 1 | 4-Chloro | |
| 18.13 | Me | — | 1 | 2-Bromo | |
| 18.14 | Me | — | 1 | 3-Bromo | |
| 18.15 | Me | — | 1 | 4-Bromo | |
| 18.16 | Me | — | 1 | 4-Et | |
| 18.17 | Me | — | 1 | 4-tert-Butyl | |
| 18.18 | Me | — | 2 | 2,3-Dimethyl | |
| 18.19 | Me | — | 2 | 2,4-Dimethyl | |
| 18.20 | Me | — | 2 | 2,5-Dimethyl | |
| 18.21 | Me | — | 2 | 2-Me,4-F | |
| 18.22 | Me | — | 2 | 2-Me,5-F | |
| 18.23 | Me | — | 2 | 2-F,5-Me | |
| 18.24 | Me | — | 2 | 3-CF₃,4-Cl | |
| 18.25 | Me | — | 2 | 3-CF₃-Phenoxy | |
| 18.26 | Me | — | 0 | — | |
| 18.27 | CN | — | 0 | — | |
| 18.28 | Me | — | 2 | 3,4-Methylenedioxy | |
| 18.29 | Me | O | 0 | Me | |
| 18.30 | Me | O | 0 | Et | |

TABLE 18-continued

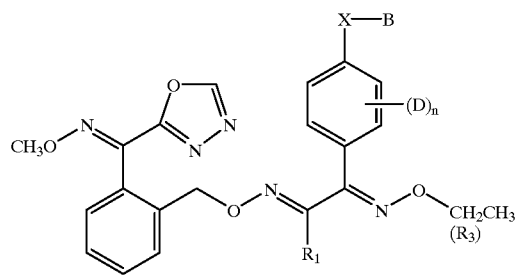

| Example No. | R₁ | X* | n | B or D | Physical data |
|---|---|---|---|---|---|
| 18.31 | Me | O | 0 | n-Propyl | |
| 18.32 | Me | O | 0 | i-Propyl | |
| 18.33 | Me | O | 0 | Allyl | |
| 18.34 | Me | O | 0 | Propargyl | |
| 18.35 | Me | O | 0 | Phenyl | |
| 18.36 | Me | O | 0 | 3-CF₃-Phenyl | |
| 18.37 | Me | O | 0 | 2-Fluorophenyl | |
| 18.38 | Me | O | 0 | 3-Fluorophenyl | |
| 18.39 | Me | O | 0 | 4-Fluorophenyl | |
| 18.40 | Me | O | 0 | 4-Chlorophenyl | |
| 18.41 | Me | O | 0 | 4-Bromophenyl | |
| 18.42 | Me | O | 0 | CF₃ | |
| 18.43 | Me | O | 0 | CHF₂ | |
| 18.44 | Me | O | 0 | CF₂CHF₂ | |
| 18.45 | Me | S | 0 | Me | |
| 18.46 | Me | —SO₂— | 0 | Me | |
| 18.47 | Me | S | 0 | Et | |
| 18.48 | Me | —SO₂— | 0 | Et | |
| 18.49 | Me | S | 0 | n-Propyl | |
| 18.50 | Me | —SO₂— | 0 | n-Propyl | |
| 18.51 | Me | S | 0 | i-Propyl | |
| 18.52 | Me | S | 0 | Phenyl | |
| 18.53 | Me | S | 0 | 2-Pyridyl | |
| 18.54 | Me | S | 0 | 2-Pyrimidinyl | |
| 18.55 | Me | S | 0 | 5-Me-1,3,4-Thiadiazolyl | |
| 18.56 | Me | —OCH₂— | 0 | Phenyl | |
| 18.57 | Me | —OCH₂— | 0 | 3-CF₃-Phenyl | |
| 18.58 | Me | —OCH₂— | 0 | 2-CF₃-Phenyl | |
| 18.59 | Me | —OCH₂— | 0 | 4-CF₃-Phenyl | |
| 18.60 | Me | —OCH₂— | 0 | 2-F-Phenyl | |
| 18.61 | Me | —OCH₂— | 0 | 3-F-Phenyl | |
| 18.62 | Me | —OCH₂— | 0 | 4-F-Phenyl | |
| 18.63 | Me | —OCH₂— | 0 | 3-Me-Phenyl | |
| 18.64 | Me | OCH₂ | 0 | 3-Cl-Phenyl | |
| 18.65 | Me | OCH₂ | 0 | 3-Br-Phenyl | |
| 18.66 | Me | OCH₂ | 0 | 3-CH₃O-Phenyl | |
| 18.67 | Me | —OCH₂— | 0 | Trimethylsilyl | |
| 18.68 | Me | —OCH₂— | 0 | Cyclohexyl | |
| 18.69 | Me | —OCH₂— | 0 | CF₃ | |
| 18.70 | Me | O | 0 | 4-Me-phenyl | |
| 18.71 | Me | O | 0 | 3-Cl-phenyl | |
| 18.72 | Me | O | 0 | 3-Br-phenyl | |
| 18.73 | Me | — | 2 | 2,4-Di-fluoro | |
| 18.74 | Me | — | 1 | 4-Ethynyl | |
| 18.75 | Me | — | 1 | 4-(3-Methyl-isoxazol-5-yl) | |
| 18.76 | Me | — | 1 | 4-Phenyl | |
| 18.77 | Me | — | 1 | 4-(p-Chlorophenyl) | |
| 18.78 | Me | — | 1 | 2-Methoxy | |
| 18.79 | Me | — | 1 | 4-Trimethylsilyl | |
| 18.80 | Me | O | 0 | n-Butyl | |
| 18.81 | Me | O | 0 | s-Butyl | |
| 18.82 | Me | O | 0 | i-Butyl | |
| 18.83 | Me | O | 0 | t-Butyl | |
| 18.84 | Me | — | 2 | 2-F,4-Me | |
| 18.85 | Me | O | 0 | 4-t-Butylphenyl | |
| 18.86 | Me | O | 0 | Cyclopentyl | |
| 18.87 | Me | O | 0 | 2,4-Difluorophenyl | |
| 18.88 | Me | O | 0 | 4-F,3-Cl-phenyl | |
| 18.89 | Me | — | 2 | 2-F,4-nPropyloxy | |
| 18.90 | Me | — | 2 | 2-F,4-Ethoxy | |

TABLE 18-continued

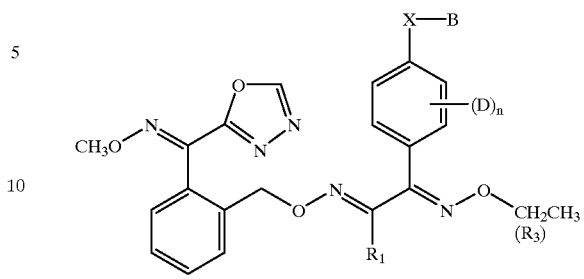

| Example No. | R₁ | X* | n | B or D | Physical data |
|---|---|---|---|---|---|
| 18.91 | Me | — | 2 | 2-Me,4-nPropyloxy | |
| 18.92 | Me | — | 2 | 2-Me,4-Ethoxy | |
| 18.93 | Me | — | 2 | 2-F,4-iPropyloxy | |
| 18.94 | Me | — | 2 | 2,4-Dimethoxy | |
| 18.95 | Me | — | 2 | 2-F,4-Methoxy | |
| 18.96 | Me | — | 2 | 2-F,4-nButyloxy | |
| 18.97 | Me | — | 2 | 2-F,4-sButyloxy | |
| 18.98 | Me | — | 2 | 2-F,4-iButyloxy | |
| 18.99 | Me | — | 2 | 2-F,4-Cyclopentyloxy | |
| 18.100 | Me | — | 2 | 2-Me,4-Methoxy | |
| 18.101 | Me | — | 2 | 2-Me,4-iPropyloxy | |
| 18.102 | Me | — | 2 | 2-Me,4-nButyloxy | |
| 18.103 | Me | — | 2 | 2-Me,4-sButyloxy | |
| 18.104 | Me | — | 2 | 2-Me,4-iButyloxy | |
| 18.105 | Me | — | 2 | 2-Me,4-Cyclopentyloxy | |
| 18.106 | Me | — | 2 | 2-F,4-(2,2-Dichlorocyclopropylmethoxy) | |
| 18.107 | Me | — | 2 | 2-Me,4-(2,2-Dichlorocyclopropylmethoxy) | |
| 18.108 | Me | — | 2 | 2-Methoxy,4-F | |
| 18.109 | Me | — | 2 | 2-Methoxy,4-Me | |

TABLE 19

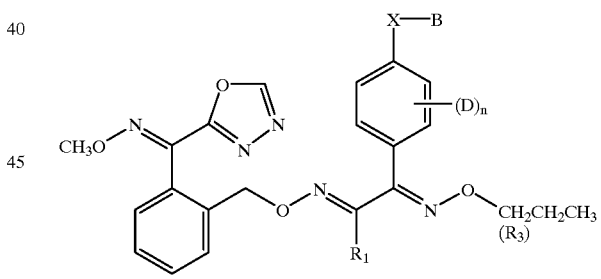

| Example No. | R₁ | X* | n | B or D | Physical data |
|---|---|---|---|---|---|
| 19.1 | Me | — | 1 | 2-Me | |
| 19.2 | Me | — | 1 | 3-Me | |
| 19.3 | Me | — | 1 | 4-Me | |
| 19.4 | Me | — | 1 | 2-CF₃ | |
| 19.5 | Me | — | 1 | 3-CF₃ | |
| 19.6 | Me | — | 1 | 4-CF₃ | |
| 19.7 | Me | — | 1 | 2-Fluoro | |
| 19.8 | Me | — | 1 | 3-Fluoro | |
| 19.9 | Me | — | 1 | 4-Fluoro | |
| 19.10 | Me | — | 1 | 2-Chloro | |
| 19.11 | Me | — | 1 | 3-Chloro | |
| 19.12 | Me | — | 1 | 4-Chloro | |
| 19.13 | Me | — | 1 | 2-Bromo | |
| 19.14 | Me | — | 1 | 3-Bromo | |
| 19.15 | Me | — | 1 | 4-Bromo | |
| 19.16 | Me | — | 1 | 4-Et | |

TABLE 19-continued

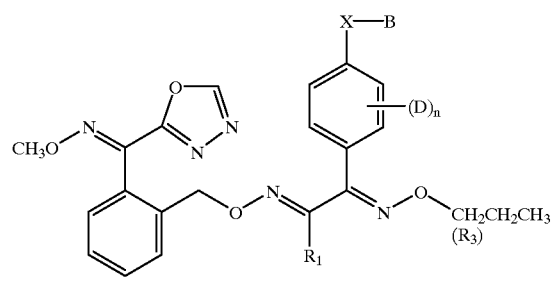

| Example No. | R₁ | X* | n | B or D | Physical data |
|---|---|---|---|---|---|
| 19.17 | Me | — | 1 | 4-tert-Butyl | |
| 19.18 | Me | — | 2 | 2,3-Dimethyl | |
| 19.19 | Me | — | 2 | 2,4-Dimethyl | |
| 19.20 | Me | — | 2 | 2,5-Dimethyl | |
| 19.21 | Me | — | 2 | 2-Me,4-F | |
| 19.22 | Me | — | 2 | 2-Me,5-F | |
| 19.23 | Me | — | 2 | 2-F,5-Me | |
| 19.24 | Me | — | 2 | 3-CF₃,4-Cl | |
| 19.25 | Me | — | 2 | 3-CF₃-Phenoxy | |
| 19.26 | Me | — | 0 | — | |
| 19.27 | CN | — | 0 | — | |
| 19.28 | Me | — | 2 | 3,4-Methylenedioxy | |
| 19.29 | Me | O | 0 | Me | |
| 19.30 | Me | O | 0 | Et | |
| 19.31 | Me | O | 0 | n-Propyl | |
| 19.32 | Me | O | 0 | i-Propyl | |
| 19.33 | Me | O | 0 | Allyl | |
| 19.34 | Me | O | 0 | Propargyl | |
| 19.35 | Me | O | 0 | Phenyl | |
| 19.36 | Me | O | 0 | 3-CF₃-Phenyl | |
| 19.37 | Me | O | 0 | 2-Fluorophenyl | |
| 19.38 | Me | O | 0 | 3-Fluorophenyl | |
| 19.39 | Me | O | 0 | 4-Fluorophenyl | |
| 19.40 | Me | O | 0 | 4-Chlorophenyl | |
| 19.41 | Me | O | 0 | 4-Bromophenyl | |
| 19.42 | Me | O | 0 | CF₃ | |
| 19.43 | Me | O | 0 | CHF₂ | |
| 19.44 | Me | O | 0 | CF₂CHF₂ | |
| 19.45 | Me | S | 0 | Me | |
| 19.46 | Me | —SO₂— | 0 | Me | |
| 19.47 | Me | S | 0 | Et | |
| 19.48 | Me | —SO₂— | 0 | Et | |
| 19.49 | Me | S | 0 | n-Propyl | |
| 19.50 | Me | —SO₂— | 0 | n-Propyl | |
| 19.51 | Me | S | 0 | i-Propyl | |
| 19.52 | Me | S | 0 | Phenyl | |
| 19.53 | Me | S | 0 | 2-Pyridyl | |
| 19.54 | Me | S | 0 | 2-Pyrimidinyl | |
| 19.55 | Me | S | 0 | 5-Me-1,3,4-Thiadiazolyl | |
| 19.56 | Me | —OCH₂— | 0 | Phenyl | |
| 19.57 | Me | —OCH₂— | 0 | 3-CF₃-Phenyl | |
| 19.58 | Me | —OCH₂— | 0 | 2-CF₃-Phenyl | |
| 19.59 | Me | —OCH₂— | 0 | 4-CF₃-Phenyl | |
| 19.60 | Me | —OCH₂— | 0 | 2-F-Phenyl | |
| 19.61 | Me | —OCH₂— | 0 | 3-F-Phenyl | |
| 19.62 | Me | —OCH₂— | 0 | 4-F-Phenyl | |
| 19.63 | Me | —OCH₂— | 0 | 3-Me-Phenyl | |
| 19.64 | Me | OCH₂ | 0 | 3-Cl-Phenyl | |
| 19.65 | Me | OCH₂ | 0 | 3-Br-Phenyl | |
| 19.66 | Me | OCH₂ | 0 | 3-CH₃O-Phenyl | |
| 19.67 | Me | —OCH₂— | 0 | Trimethylsilyl | |
| 19.68 | Me | —OCH₂— | 0 | Cyclohexyl | |
| 19.69 | Me | —OCH₂— | 0 | CF₃ | |
| 19.70 | Me | O | 0 | 4-Me-phenyl | |
| 19.71 | Me | O | 0 | 3-Cl-phenyl | |
| 19.72 | Me | O | 0 | 3-Br-phenyl | |
| 19.73 | Me | — | 2 | 2,4-Di-fluoro | |
| 19.74 | Me | — | 1 | 4-Ethynyl | |
| 19.75 | Me | — | 1 | 4-(3-Methyl-isoxazol-5-yl) | |
| 19.76 | Me | — | 1 | 4-Phenyl | |

TABLE 19-continued

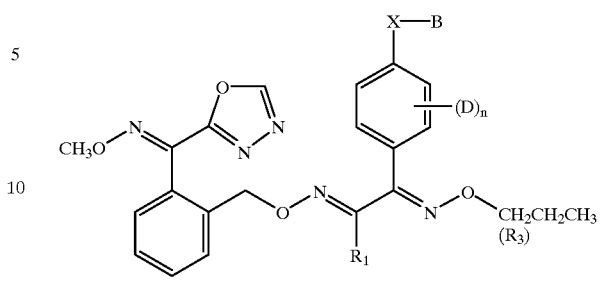

| Example No. | R₁ | X* | n | B or D | Physical data |
|---|---|---|---|---|---|
| 19.77 | Me | — | 1 | 4-(p-Chlorophenyl) | |
| 19.78 | Me | — | 1 | 2-Methoxy | |
| 19.79 | Me | — | 1 | 4-Trimethylsilyl | |
| 19.80 | Me | O | 0 | n-Butyl | |
| 19.81 | Me | O | 0 | s-Butyl | |
| 19.82 | Me | O | 0 | i-Butyl | |
| 19.83 | Me | O | 0 | t-Butyl | |
| 19.84 | Me | — | 2 | 2-F,4-Me | |
| 19.85 | Me | O | 0 | 4-t-Butylphenyl | |
| 19.86 | Me | O | 0 | Cyclopentyl | |
| 19.87 | Me | O | 0 | 2,4-Difluorophenyl | |
| 19.88 | Me | O | 0 | 4-F,3-Cl-phenyl | |
| 19.89 | Me | — | 2 | 2-F,4-nPropyloxy | |
| 19.90 | Me | — | 2 | 2-F,4-Ethoxy | |
| 19.91 | Me | — | 2 | 2-Me,4-nPropyloxy | |
| 19.92 | Me | — | 2 | 2-Me,4-Ethoxy | |
| 19.93 | Me | — | 2 | 2-F,4-iPropyloxy | |
| 19.94 | Me | — | 2 | 2,4-Dimethoxy | |
| 19.95 | Me | — | 2 | 2-F,4-Methoxy | |
| 19.96 | Me | — | 2 | 2-F,4-nButyloxy | |
| 19.97 | Me | — | 2 | 2-F,4-sButyloxy | |
| 19.98 | Me | — | 2 | 2-F,4-iButyloxy | |
| 19.99 | Me | — | 2 | 2-F,4-Cyclopentyloxy | |
| 19.100 | Me | — | 2 | 2-Me,4-Methoxy | |
| 19.101 | Me | — | 2 | 2-Me,4-iPropyloxy | |
| 19.102 | Me | — | 2 | 2-Me,4-nButyloxy | |
| 19.103 | Me | — | 2 | 2-Me,4-sButyloxy | |
| 19.104 | Me | — | 2 | 2-Me,4-iButyloxy | |
| 19.105 | Me | — | 2 | 2-Me,4-Cyclopentyloxy | |
| 19.106 | Me | — | 2 | 2-F,4-(2,2-Dichlorocyclopropylmethoxy) | |
| 19.107 | Me | — | 2 | 2-Me,4-(2,2-Dichlorocyclopropylmethoxy) | |
| 19.108 | Me | — | 2 | 2-Methoxy,4-F | |
| 19.109 | Me | — | 2 | 2-Methoxy,4-Me | |

TABLE 20

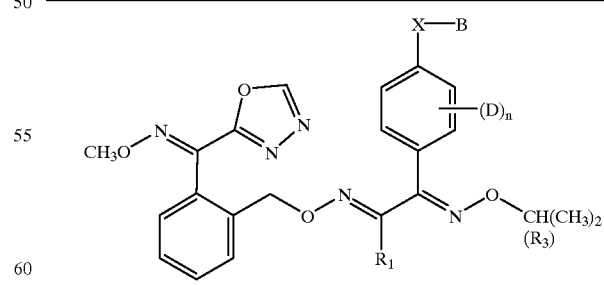

| Example No. | R₁ | X* | n | B or D | Physical data |
|---|---|---|---|---|---|
| 20.1 | Me | — | 1 | 2-Me | |
| 20.2 | Me | — | 1 | 3-Me | |
| 20.3 | Me | — | 1 | 4-Me | |

TABLE 20-continued

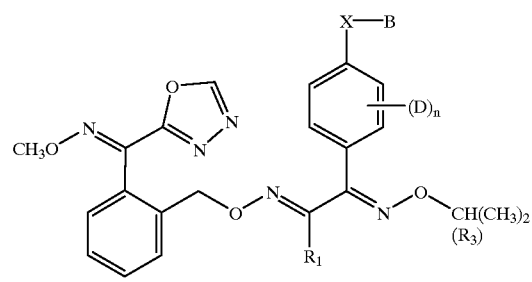

| Example No. | R₁ | X* | n | B or D | Physical data |
|---|---|---|---|---|---|
| 20.4 | Me | — | 1 | 2-CF₃ | |
| 20.5 | Me | — | 1 | 3-CF₃ | |
| 20.6 | Me | — | 1 | 4-CF₃ | |
| 20.7 | Me | — | 1 | 2-Fluoro | |
| 20.8 | Me | — | 1 | 3-Fluoro | |
| 20.9 | Me | — | 1 | 4-Fluoro | |
| 20.10 | Me | — | 1 | 2-Chloro | |
| 20.11 | Me | — | 1 | 3-Chloro | |
| 20.12 | Me | — | 1 | 4-Chloro | |
| 20.13 | Me | — | 1 | 2-Bromo | |
| 20.14 | Me | — | 1 | 3-Bromo | |
| 20.15 | Me | — | 1 | 4-Bromo | |
| 20.16 | Me | — | 1 | 4-Et | |
| 20.17 | Me | — | 1 | 4-ter.-Butyl | |
| 20.18 | Me | — | 2 | 2,3-Dimethyl | |
| 20.19 | Me | — | 2 | 2,4-Dimethyl | |
| 20.20 | Me | — | 2 | 2,5-Dimethyl | |
| 20.21 | Me | — | 2 | 2-Me,4-F | |
| 20.22 | Me | — | 2 | 2-Me,5-F | |
| 20.23 | Me | — | 2 | 2-F,5-Me | |
| 20.24 | Me | — | 2 | 3-CF₃,4-Cl | |
| 20.25 | Me | — | 2 | 3-CF₃-Phenoxy | |
| 20.26 | Me | — | 0 | — | |
| 20.27 | CN | — | 0 | — | |
| 20.28 | Me | — | 2 | 3,4-Methylenedioxy | |
| 20.29 | Me | O | 0 | Me | |
| 20.30 | Me | O | 0 | Et | |
| 20.31 | Me | O | 0 | n-Propyl | |
| 20.32 | Me | O | 0 | i-Propyl | |
| 20.33 | Me | O | 0 | Allyl | |
| 20.34 | Me | O | 0 | Propargyl | |
| 20.35 | Me | O | 0 | Phenyl | |
| 20.36 | Me | O | 0 | 3-CF₃-Phenyl | |
| 20.37 | Me | O | 0 | 2-Fluorophenyl | |
| 20.38 | Me | O | 0 | 3-Fluorophenyl | |
| 20.39 | Me | O | 0 | 4-Fluorophenyl | |
| 20.40 | Me | O | 0 | 4-Chlorophenyl | |
| 20.41 | Me | O | 0 | 4-Bromophenyl | |
| 20.42 | Me | O | 0 | CF₃ | |
| 20.43 | Me | O | 0 | CHF₂ | |
| 20.44 | Me | O | 0 | CF₂CHF₂ | |
| 20.45 | Me | S | 0 | Me | |
| 20.46 | Me | —SO₂— | 0 | Me | |
| 20.47 | Me | S | 0 | Et | |
| 20.48 | Me | —SO₂— | 0 | Et | |
| 20.49 | Me | S | 0 | n-Propyl | |
| 20.50 | Me | —SO₂— | 0 | n-Propyl | |
| 20.51 | Me | S | 0 | i-Propyl | |
| 20.52 | Me | S | 0 | Phenyl | |
| 20.53 | Me | S | 0 | 2-Pyridyl | |
| 20.54 | Me | S | 0 | 2-Pyrimidinyl | |
| 20.55 | Me | S | 0 | 5-Me-1,3,4-Thiadiazolyl | |
| 20.56 | Me | —OCH₂— | 0 | Phenyl | |
| 20.57 | Me | —OCH₂— | 0 | 3-CF₃-Phenyl | |
| 20.58 | Me | —OCH₂— | 0 | 2-CF₃-Phenyl | |
| 20.59 | Me | —OCH₂— | 0 | 4-CF₃-Phenyl | |
| 20.60 | Me | —OCH₂— | 0 | 2-F-Phenyl | |
| 20.61 | Me | —OCH₂— | 0 | 3-F-Phenyl | |
| 20.62 | Me | —OCH₂— | 0 | 4-F-Phenyl | |
| 20.63 | Me | —OCH₂— | 0 | 3-Me-Phenyl | |

TABLE 20-continued

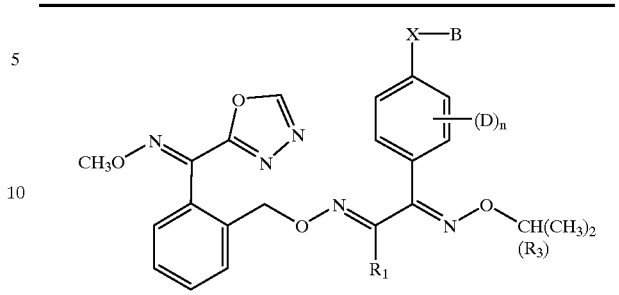

| Example No. | R₁ | X* | n | B or D | Physical data |
|---|---|---|---|---|---|
| 20.64 | Me | OCH₂ | 0 | 3-Cl-Phenyl | |
| 20.65 | Me | OCH₂ | 0 | 3-Br-Phenyl | |
| 20.66 | Me | OCH₂ | 0 | 3-CH₃O-Phenyl | |
| 20.67 | Me | —OCH₂— | 0 | Trimethylsilyl | |
| 20.68 | Me | —OCH₂— | 0 | Cyclohexyl | |
| 20.69 | Me | —OCH₂— | 0 | CF₃ | |
| 20.70 | Me | O | 0 | 4-Me-phenyl | |
| 20.71 | Me | O | 0 | 3-Cl-phenyl | |
| 20.72 | Me | O | 0 | 3-Br-phenyl | |
| 20.73 | Me | — | 2 | 2,4-Di-fluoro | |
| 20.74 | Me | — | 1 | 4-Ethynyl | |
| 20.75 | Me | — | 1 | 4-(3-Methyl-isoxazol-5-yl) | |
| 20.76 | Me | — | 1 | 4-Phenyl | |
| 20.77 | Me | — | 1 | 4-(p-Chlorophenyl) | |
| 20.78 | Me | — | 1 | 2-Methoxy | |
| 20.79 | Me | — | 1 | 4-Trimethylsilyl | |
| 20.80 | Me | O | 0 | n-Butyl | |
| 20.81 | Me | O | 0 | s-Butyl | |
| 20.82 | Me | O | 0 | i-Butyl | |
| 20.83 | Me | O | 0 | t-Butyl | |
| 20.84 | Me | — | 2 | 2-F,4-Me | |
| 20.85 | Me | O | 0 | 4-t-Butylphenyl | |
| 20.86 | Me | O | 0 | Cyclopentyl | |
| 20.87 | Me | O | 0 | 2,4-Difluorophenyl | |
| 20.88 | Me | O | 0 | 4-F,3-Cl-phenyl | |
| 20.89 | Me | — | 2 | 2-F,4-nPropyloxy | |
| 20.90 | Me | — | 2 | 2-F,4-Ethoxy | |
| 20.91 | Me | — | 2 | 2-Me,4-nPropyloxy | |
| 20.92 | Me | — | 2 | 2-Me,4-Ethoxy | |
| 20.93 | Me | — | 2 | 2-F,4-iPropyloxy | |
| 20.94 | Me | — | 2 | 2,4-Dimethoxy | |
| 20.95 | Me | — | 2 | 2-F,4-Methoxy | |
| 20.96 | Me | — | 2 | 2-F,4-nButyloxy | |
| 20.97 | Me | — | 2 | 2-F,4-sButyloxy | |
| 20.98 | Me | — | 2 | 2-F,4-iButyloxy | |
| 20.99 | Me | — | 2 | 2-F,4-Cyclopentyloxy | |
| 20.100 | Me | — | 2 | 2-Me,4-Methoxy | |
| 20.101 | Me | — | 2 | 2-Me,4-iPropyloxy | |
| 20.102 | Me | — | 2 | 2-Me,4-nButyloxy | |
| 20.103 | Me | — | 2 | 2-Me,4-sButyloxy | |
| 20.104 | Me | — | 2 | 2-Me,4-iButyloxy | |
| 20.105 | Me | — | 2 | 2-Me,4-Cyclopentyloxy | |
| 20.106 | Me | — | 2 | 2-F,4-(2,2-Dichlorocyclopropylmethoxy) | |
| 20.107 | Me | — | 2 | 2-Me,4-(2,2-Dichlorocyclopropylmethoxy) | |
| 20.108 | Me | — | 2 | 2-Methoxy,4-F | |
| 20.109 | Me | — | 2 | 2-Methoxy,4-Me | |

TABLE 21

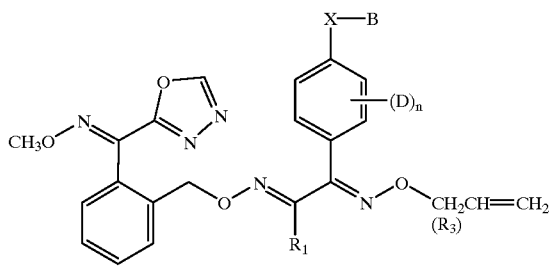

| Example No. | R₁ | X* | n | B or D | Physical data |
|---|---|---|---|---|---|
| 21.1 | Me | — | 1 | 2-Me | |
| 21.2 | Me | — | 1 | 3-Me | |
| 21.3 | Me | — | 1 | 4-Me | |
| 21.4 | Me | — | 1 | 2-CF₃ | |
| 21.5 | Me | — | 1 | 3-CF₃ | |
| 21.6 | Me | — | 1 | 4-CF₃ | |
| 21.7 | Me | — | 1 | 2-Fluoro | |
| 21.8 | Me | — | 1 | 3-Fluoro | |
| 21.9 | Me | — | 1 | 4-Fluoro | |
| 21.10 | Me | — | 1 | 2-Chloro | |
| 21.11 | Me | — | 1 | 3-Chloro | |
| 21.12 | Me | — | 1 | 4-Chloro | |
| 21.13 | Me | — | 1 | 2-Bromo | |
| 21.14 | Me | — | 1 | 3-Bromo | |
| 21.15 | Me | — | 1 | 4-Bromo | |
| 21.16 | Me | — | 1 | 4-Et | |
| 21.17 | Me | — | 1 | 4-tert-Butyl | |
| 21.18 | Me | — | 2 | 2,3-Dimethyl | |
| 21.19 | Me | — | 2 | 2,4-Dimethyl | |
| 21.20 | Me | — | 2 | 2,5-Dimethyl | |
| 21.21 | Me | — | 2 | 2-Me,4-F | |
| 21.22 | Me | — | 2 | 2-Me,5-F | |
| 21.23 | Me | — | 2 | 2-F,5-Me | |
| 21.24 | Me | — | 2 | 3-CF₃,4-Cl | |
| 21.25 | Me | — | 2 | 3-CF₃-Phenoxy | |
| 21.26 | Me | — | 0 | — | |
| 21.27 | CN | — | 0 | — | |
| 21.28 | Me | — | 2 | 3,4-Methylenedioxy | |
| 21.29 | Me | O | 0 | Me | |
| 21.30 | Me | O | 0 | Et | |
| 21.31 | Me | O | 0 | n-Propyl | |
| 21.32 | Me | O | 0 | i-Propyl | |
| 21.33 | Me | O | 0 | Allyl | |
| 21.34 | Me | O | 0 | Propargyl | |
| 21.35 | Me | O | 0 | Phenyl | |
| 21.36 | Me | O | 0 | 3-CF₃-Phenyl | |
| 21.37 | Me | O | 0 | 2-Fluorophenyl | |
| 21.38 | Me | O | 0 | 3-Fluorophenyl | |
| 21.39 | Me | O | 0 | 4-Fluorophenyl | |
| 21.40 | Me | O | 0 | 4-Chlorophenyl | |
| 21.41 | Me | O | 0 | 4-Bromophenyl | |
| 21.42 | Me | O | 0 | CF₃ | |
| 21.43 | Me | O | 0 | CHF₂ | |
| 21.44 | Me | O | 0 | CF₂CHF₂ | |
| 21.45 | Me | S | 0 | Me | |
| 21.46 | Me | —SO₂— | 0 | Me | |
| 21.47 | Me | S | 0 | Et | |
| 21.48 | Me | —SO₂— | 0 | Et | |
| 21.49 | Me | S | 0 | n-Propyl | |
| 21.50 | Me | —SO₂— | 0 | n-Propyl | |
| 21.51 | Me | S | 0 | i-Propyl | |
| 21.52 | Me | S | 0 | Phenyl | |
| 21.53 | Me | S | 0 | 2-Pyridyl | |
| 21.54 | Me | S | 0 | 2-Pyrimidinyl | |
| 21.55 | Me | S | 0 | 5-Me-1,3,4-Thiadiazolyl | |
| 21.56 | Me | —OCH₂— | 0 | Phenyl | |
| 21.57 | Me | —OCH₂— | 0 | 3-CF₃-Phenyl | |
| 21.58 | Me | —OCH₂— | 0 | 2-CF₃-Phenyl | |
| 21.59 | Me | —OCH₂— | 0 | 4-CF₃-Phenyl | |
| 21.60 | Me | —OCH₂— | 0 | 2-F-Phenyl | |
| 21.61 | Me | —OCH₂— | 0 | 3-F-Phenyl | |
| 21.62 | Me | —OCH₂— | 0 | 4-F-Phenyl | |
| 21.63 | Me | —OCH₂— | 0 | 3-Me-Phenyl | |
| 21.64 | Me | OCH₂ | 0 | 3-Cl-Phenyl | |
| 21.65 | Me | OCH₂ | 0 | 3-Br-Phenyl | |
| 21.66 | Me | OCH₂ | 0 | 3-CH₃O-Phenyl | |
| 21.67 | Me | —OCH₂— | 0 | Trimethylsilyl | |
| 21.68 | Me | —OCH₂— | 0 | Cyclohexyl | |
| 21.69 | Me | —OCH₂— | 0 | CF₃ | |
| 21.70 | Me | O | 0 | 4-Me-phenyl | |
| 21.71 | Me | O | 0 | 3-Cl-phenyl | |
| 21.72 | Me | O | 0 | 3-Br-phenyl | |
| 21.73 | Me | — | 2 | 2,4-Di-fluoro | |
| 21.74 | Me | — | 1 | 4-Ethynyl | |
| 21.75 | Me | — | 1 | 4-(3-Methyl-isoxazol-5-yl) | |
| 21.76 | Me | — | 1 | 4-Phenyl | |
| 21.77 | Me | — | 1 | 4-(p-Chlorophenyl) | |
| 21.78 | Me | — | 1 | 2-Methoxy | |
| 21.79 | Me | — | 1 | 4-Trimethylsilyl | |
| 21.80 | Me | O | 0 | n-Butyl | |
| 21.81 | Me | O | 0 | s-Butyl | |
| 21.82 | Me | O | 0 | i-Butyl | |
| 21.83 | Me | O | 0 | t-Butyl | |
| 21.84 | Me | — | 2 | 2-F,4-Me | |
| 21.85 | Me | O | 0 | 4-t-Butylphenyl | |
| 21.86 | Me | O | 0 | Cyclopentyl | |
| 21.87 | Me | O | 0 | 2,4-Difluorophenyl | |
| 21.88 | Me | O | 0 | 4-F,3-Cl-phenyl | |
| 21.89 | Me | — | 2 | 2-F,4-nPropyloxy | |
| 21.90 | Me | — | 2 | 2-F,4-Ethoxy | |
| 21.91 | Me | — | 2 | 2-Me,4-nPropyloxy | |
| 21.92 | Me | — | 2 | 2-Me,4-Ethoxy | |
| 21.93 | Me | — | 2 | 2-F,4-iPropyloxy | |
| 21.94 | Me | — | 2 | 2,4-Dimethoxy | |
| 21.95 | Me | — | 2 | 2-F,4-Methoxy | |
| 21.96 | Me | — | 2 | 2-F,4-nButyloxy | |
| 21.97 | Me | — | 2 | 2-F,4-sButyloxy | |
| 21.98 | Me | — | 2 | 2-F,4-iButyloxy | |
| 21.99 | Me | — | 2 | 2-F,4-Cyclopentyloxy | |
| 21.100 | Me | — | 2 | 2-Me,4-Methoxy | |
| 21.101 | Me | — | 2 | 2-Me,4-iPropyloxy | |
| 21.102 | Me | — | 2 | 2-Me,4-nButyloxy | |
| 21.103 | Me | — | 2 | 2-Me,4-sButyloxy | |
| 21.104 | Me | — | 2 | 2-Me,4-iButyloxy | |
| 21.105 | Me | — | 2 | 2-Me,4-Cyclopentyloxy | |
| 21.106 | Me | — | 2 | 2-F,4-(2,2-Dichlorocyclopropylmethoxy) | |
| 21.107 | Me | — | 2 | 2-Me,4-(2,2-Dichlorocyclopropylmethoxy) | |
| 21.108 | Me | — | 2 | 2-Methoxy,4-F | |
| 21.109 | Me | — | 2 | 2-Methoxy,4-Me | |

TABLE 22

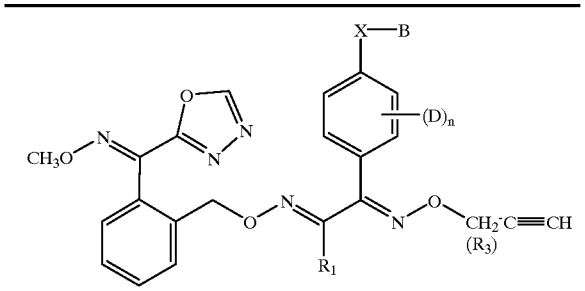

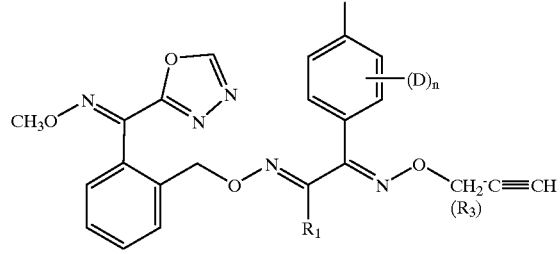

| Example No. | R₁ | X* | n | B or D | Physical data |
|---|---|---|---|---|---|
| 22.1 | Me | — | 1 | 2-Me | |
| 22.2 | Me | — | 1 | 3-Me | |
| 22.3 | Me | — | 1 | 4-Me | |
| 22.4 | Me | — | 1 | 2-CF₃ | |
| 22.5 | Me | — | 1 | 3-CF₃ | |
| 22.6 | Me | — | 1 | 4-CF₃ | |
| 22.7 | Me | — | 1 | 2-Fluoro | |
| 22.8 | Me | — | 1 | 3-Fluoro | |
| 22.9 | Me | — | 1 | 4-Fluoro | |
| 22.10 | Me | — | 1 | 2-Chloro | |
| 22.11 | Me | — | 1 | 3-Chloro | |
| 22.12 | Me | — | 1 | 4-Chloro | |
| 22.13 | Me | — | 1 | 2-Bromo | |
| 22.14 | Me | — | 1 | 3-Bromo | |
| 22.15 | Me | — | 1 | 4-Bromo | |
| 22.16 | Me | — | 1 | 4-Et | |
| 22.17 | Me | — | 1 | 4-tert-Butyl | |
| 22.18 | Me | — | 2 | 2,3-Dimethyl | |
| 22.19 | Me | — | 2 | 2,4-Dimethyl | |
| 22.20 | Me | — | 2 | 2,5-Dimethyl | |
| 22.21 | Me | — | 2 | 2-Me,4-F | |
| 22.22 | Me | — | 2 | 2-Me,5-F | |
| 22.23 | Me | — | 2 | 2-F,5-Me | |
| 22.24 | Me | — | 2 | 3-CF₃,4-Cl | |
| 22.25 | Me | — | 2 | 3-CF₃-Phenoxy | |
| 22.26 | Me | — | 0 | — | |
| 22.27 | CN | — | 0 | — | |
| 22.28 | Me | — | 2 | 3,4-Methylenedioxy | |
| 22.29 | Me | O | 0 | Me | |
| 22.30 | Me | O | 0 | Et | |
| 22.31 | Me | O | 0 | n-Propyl | |
| 22.32 | Me | O | 0 | i-Propyl | |
| 22.33 | Me | O | 0 | Allyl | |
| 22.34 | Me | O | 0 | Propargyl | |
| 22.35 | Me | O | 0 | Phenyl | |
| 22.36 | Me | O | 0 | 3-CF₃-Phenyl | |
| 22.37 | Me | O | 0 | 2-Fluorophenyl | |
| 22.38 | Me | O | 0 | 3-Fluorophenyl | |
| 22.39 | Me | O | 0 | 4-Fluorophenyl | |
| 22.40 | Me | O | 0 | 4-Chlorophenyl | |
| 22.41 | Me | O | 0 | 4-Bromophenyl | |
| 22.42 | Me | O | 0 | CF₃ | |
| 22.43 | Me | O | 0 | CHF₂ | |
| 22.44 | Me | O | 0 | CF₂CHF₂ | |
| 22.45 | Me | S | 0 | Me | |
| 22.46 | Me | —SO₂— | 0 | Me | |
| 22.47 | Me | S | 0 | Et | |
| 22.48 | Me | —SO₂— | 0 | Et | |
| 22.49 | Me | S | 0 | n-Propyl | |
| 22.50 | Me | —SO₂— | 0 | n-Propyl | |
| 22.51 | Me | S | 0 | i-Propyl | |
| 22.52 | Me | S | 0 | Phenyl | |
| 22.53 | Me | S | 0 | 2-Pyridyl | |
| 22.54 | Me | S | 0 | 2-Pyrimidinyl | |
| 22.55 | Me | S | 0 | 5-Me-1,3,4-Thiadiazolyl | |
| 22.56 | Me | —OCH₂— | 0 | Phenyl | |
| 22.57 | Me | —OCH₂— | 0 | 3-CF₃-Phenyl | |
| 22.58 | Me | —OCH₂— | 0 | 2-CF₃-Phenyl | |
| 22.59 | Me | —OCH₂— | 0 | 4-CF₃-Phenyl | |
| 22.60 | Me | —OCH₂— | 0 | 2-F-Phenyl | |
| 22.61 | Me | —OCH₂— | 0 | 3-F-Phenyl | |
| 22.62 | Me | —OCH₂— | 0 | 4-F-Phenyl | |
| 22.63 | Me | —OCH₂— | 0 | 3-Me-Phenyl | |
| 22.64 | Me | OCH₂ | 0 | 3-Cl-Phenyl | |
| 22.65 | Me | OCH₂ | 0 | 3-Br-Phenyl | |
| 22.66 | Me | OCH₂ | 0 | 3-CH₃O-Phenyl | |
| 22.67 | Me | —OCH₂— | 0 | Trimethylsilyl | |
| 22.68 | Me | —OCH₂— | 0 | Cyclohexyl | |
| 22.69 | Me | —OCH₂— | 0 | CF₃ | |
| 22.70 | Me | O | 0 | 4-Me-phenyl | |
| 22.71 | Me | O | 0 | 3-Cl-phenyl | |
| 22.72 | Me | O | 0 | 3-Br-phenyl | |
| 22.73 | Me | — | 2 | 2,4-Di-fluoro | |
| 22.74 | Me | — | 1 | 4-Ethynyl | |
| 22.75 | Me | — | 1 | 4-(3-Methyl-isoxazol-5-yl) | |
| 22.76 | Me | — | 1 | 4-Phenyl | |
| 22.77 | Me | — | 1 | 4-(p-Chlorophenyl) | |
| 22.78 | Me | — | 1 | 2-Methoxy | |
| 22.79 | Me | — | 1 | 4-Trimethylsilyl | |
| 22.80 | Me | O | 0 | n-Butyl | |
| 22.81 | Me | O | 0 | s-Butyl | |
| 22.82 | Me | O | 0 | i-Butyl | |
| 22.83 | Me | O | 0 | t-Butyl | |
| 22.84 | Me | — | 2 | 2-F,4-Me | |
| 22.85 | Me | O | 0 | 4-t-Butylphenyl | |
| 22.86 | Me | O | 0 | Cyclopentyl | |
| 22.87 | Me | O | 0 | 2,4-Difluorophenyl | |
| 22.88 | Me | O | 0 | 4-F,3-Cl-phenyl | |
| 22.89 | Me | — | 2 | 2-F,4-nPropyloxy | |
| 22.90 | Me | — | 2 | 2-F,4-Ethoxy | |
| 22.91 | Me | — | 2 | 2-Me,4-nPropyloxy | |
| 22.92 | Me | — | 2 | 2-Me,4-Ethoxy | |
| 22.93 | Me | — | 2 | 2-F,4-iPropyloxy | |
| 22.94 | Me | — | 2 | 2,4-Dimethoxy | |
| 22.95 | Me | — | 2 | 2-F,4-Methoxy | |
| 22.96 | Me | — | 2 | 2-F,4-nButyloxy | |
| 22.97 | Me | — | 2 | 2-F,4-sButyloxy | |
| 22.98 | Me | — | 2 | 2-F,4-iButyloxy | |
| 22.99 | Me | — | 2 | 2-F,4-Cyclopentyloxy | |
| 22.100 | Me | — | 2 | 2-Me,4-Methoxy | |
| 22.101 | Me | — | 2 | 2-Me,4-iPropyloxy | |
| 22.102 | Me | — | 2 | 2-Me,4-nButyloxy | |
| 22.103 | Me | — | 2 | 2-Me,4-sButyloxy | |
| 22.104 | Me | — | 2 | 2-Me,4-iButyloxy | |
| 22.105 | Me | — | 2 | 2-Me,4-Cyclopentyloxy | |
| 22.106 | Me | — | 2 | 2-F,4-(2,2-Dichlorocyclopropylmethoxy) | |
| 22.107 | Me | — | 2 | 2-Me,4-(2,2-Dichlorocyclopropylmethoxy) | |
| 22.108 | Me | — | 2 | 2-Methoxy,4-F | |
| 22.109 | Me | — | 2 | 2-Methoxy,4-Me | |

TABLE 23

| Example No. | R₁ | X* | n | B or D | Physical data |
|---|---|---|---|---|---|
| 23.1 | Me | — | 1 | 2-Me | |
| 23.2 | Me | — | 1 | 3-Me | |
| 23.3 | Me | — | 1 | 4-Me | |
| 23.4 | Me | — | 1 | 2-CF₃ | |
| 23.5 | Me | — | 1 | 3-CF₃ | |
| 23.6 | Me | — | 1 | 4-CF₃ | |
| 23.7 | Me | — | 1 | 2-Fluoro | |
| 23.8 | Me | — | 1 | 3-Fluoro | |
| 23.9 | Me | — | 1 | 4-Fluoro | |
| 23.10 | Me | — | 1 | 2-Chloro | |
| 23.11 | Me | — | 1 | 3-Chloro | |
| 23.12 | Me | — | 1 | 4-Chloro | |
| 23.13 | Me | — | 1 | 2-Bromo | |
| 23.14 | Me | — | 1 | 3-Bromo | |
| 23.15 | Me | — | 1 | 4-Bromo | |
| 23.16 | Me | — | 1 | 4-Et | |
| 23.17 | Me | — | 1 | 4-tert-Butyl | |
| 23.18 | Me | — | 2 | 2,3-Dimethyl | |
| 23.19 | Me | — | 2 | 2,4-Dimethyl | |
| 23.20 | Me | — | 2 | 2,5-Dimethyl | |
| 23.21 | Me | — | 2 | 2-Me,4-F | |
| 23.22 | Me | — | 2 | 2-Me,5-F | |
| 23.23 | Me | — | 2 | 2-F,5-Me | |
| 23.24 | Me | — | 2 | 3-CF₃,4-Cl | |
| 23.25 | Me | — | 2 | 3-CF₃-Phenoxy | |
| 23.26 | Me | — | 0 | — | |
| 23.27 | CN | — | 0 | — | |
| 23.28 | Me | — | 2 | 3,4-Methylenedioxy | |
| 23.29 | Me | O | 0 | Me | |
| 23.30 | Me | O | 0 | Et | |
| 23.31 | Me | O | 0 | n-Propyl | |
| 23.32 | Me | O | 0 | i-Propyl | |
| 23.33 | Me | O | 0 | Allyl | |
| 23.34 | Me | O | 0 | Propargyl | |
| 23.35 | Me | O | 0 | Phenyl | |
| 23.36 | Me | O | 0 | 3-CF₃-Phenyl | |
| 23.37 | Me | O | 0 | 2-Fluorophenyl | |
| 23.38 | Me | O | 0 | 3-Fluorophenyl | |
| 23.39 | Me | O | 0 | 4-Fluorophenyl | |
| 23.40 | Me | O | 0 | 4-Chlorophenyl | |
| 23.41 | Me | O | 0 | 4-Bromophenyl | |
| 23.42 | Me | O | 0 | CF₃ | |
| 23.43 | Me | O | 0 | CHF₂ | |
| 23.44 | Me | O | 0 | CF₂CHF₂ | |
| 23.45 | Me | S | 0 | Me | |
| 23.46 | Me | —SO₂— | 0 | Me | |
| 23.47 | Me | S | 0 | Et | |
| 23.48 | Me | —SO₂— | 0 | Et | |
| 23.49 | Me | S | 0 | n-Propyl | |
| 23.50 | Me | —SO₂— | 0 | n-Propyl | |
| 23.51 | Me | S | 0 | i-Propyl | |
| 23.52 | Me | S | 0 | Phenyl | |
| 23.53 | Me | S | 0 | 2-Pyridyl | |
| 23.54 | Me | S | 0 | 2-Pyrimidinyl | |
| 23.55 | Me | S | 0 | 5-Me-1,3,4-Thiadiazolyl | |
| 23.56 | Me | —OCH₂— | 0 | Phenyl | |
| 23.57 | Me | —OCH₂— | 0 | 3-CF₃-Phenyl | |
| 23.58 | Me | —OCH₂— | 0 | 2-CF₃-Phenyl | |
| 23.59 | Me | —OCH₂— | 0 | 4-CF₃-Phenyl | |
| 23.60 | Me | —OCH₂— | 0 | 2-F-Phenyl | |
| 23.61 | Me | —OCH₂— | 0 | 3-F-Phenyl | |
| 23.62 | Me | —OCH₂— | 0 | 4-F-Phenyl | |
| 23.63 | Me | —OCH₂— | 0 | 3-Me-Phenyl | |
| 23.64 | Me | OCH₂ | 0 | 3-Cl-Phenyl | |
| 23.65 | Me | OCH₂ | 0 | 3-Br-Phenyl | |
| 23.66 | Me | OCH₂ | 0 | 3-CH₃O-Phenyl | |
| 23.67 | Me | —OCH₂— | 0 | Trimethylsilyl | |
| 23.68 | Me | —OCH₂— | 0 | Cyclohexyl | |
| 23.69 | Me | —OCH₂— | 0 | CF₃ | |
| 23.70 | Me | O | 0 | 4-Me-phenyl | |
| 23.71 | Me | O | 0 | 3-Cl-phenyl | |
| 23.72 | Me | O | 0 | 3-Br-phenyl | |
| 23.73 | Me | — | 2 | 2,4-Di-fluoro | |
| 23.74 | Me | — | 1 | 4-Ethynyl | |
| 23.75 | Me | — | 1 | 4-(3-Methyl-isoxazol-5-yl) | |
| 23.76 | Me | — | 1 | 4-Phenyl | |
| 23.77 | Me | — | 1 | 4-(p-Chlorophenyl) | |
| 23.78 | Me | — | 1 | 2-Methoxy | |
| 23.79 | Me | — | 1 | 4-Trimethylsilyl | |
| 23.80 | Me | O | 0 | n-Butyl | |
| 23.81 | Me | O | 0 | s-Butyl | |
| 23.82 | Me | O | 0 | i-Butyl | |
| 23.83 | Me | O | 0 | t-Butyl | |
| 23.84 | Me | — | 2 | 2-F,4-Me | |
| 23.85 | Me | O | 0 | 4-t-Butylphenyl | |
| 23.86 | Me | O | 0 | Cyclopentyl | |
| 23.87 | Me | O | 0 | 2,4-Difluorophenyl | |
| 23.88 | Me | O | 0 | 4-F,3-Cl-phenyl | |
| 23.89 | Me | — | 2 | 2-F,4-nPropyloxy | |
| 23.90 | Me | — | 2 | 2-F,4-Ethoxy | |
| 23.91 | Me | — | 2 | 2-Me,4-nPropyloxy | |
| 23.92 | Me | — | 2 | 2-Me,4-Ethoxy | |
| 23.93 | Me | — | 2 | 2-F,4-iPropyloxy | |
| 23.94 | Me | — | 2 | 2,4-Dimethoxy | |
| 23.95 | Me | — | 2 | 2-F,4-Methoxy | |
| 23.96 | Me | — | 2 | 2-F,4-nButyloxy | |
| 23.97 | Me | — | 2 | 2-F,4-sButyloxy | |
| 23.98 | Me | — | 2 | 2-F,4-iButyloxy | |
| 23.99 | Me | — | 2 | 2-F,4-Cyclopentyloxy | |
| 23.100 | Me | — | 2 | 2-Me,4-Methoxy | |
| 23.101 | Me | — | 2 | 2-Me,4-iPropyloxy | |
| 23.102 | Me | — | 2 | 2-Me,4-nButyloxy | |
| 23.103 | Me | — | 2 | 2-Me,4-sButyloxy | |
| 23.104 | Me | — | 2 | 2-Me,4-iButyloxy | |
| 23.105 | Me | — | 2 | 2-Me,4-Cyclopentyloxy | |
| 23.106 | Me | — | 2 | 2-F,4-(2,2-Dichlorocyclopropylmethoxy) | |
| 23.107 | Me | — | 2 | 2-Me,4-(2,2-Dichlorocyclopropylmethoxy) | |
| 23.108 | Me | — | 2 | 2-Methoxy,4-F | |
| 23.109 | Me | — | 2 | 2-Methoxy,4-Me | |

TABLE 24

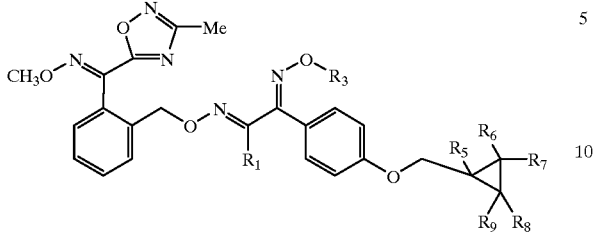

| Example No. | R₁ | R₃ | R₅ | R₆ | R₇ | R₈ | R₉ | Physical data |
|---|---|---|---|---|---|---|---|---|
| 24.1 | Me | Me | H | H | H | H | H | |
| 24.2 | Me | Me | H | Cl | Cl | H | H | |
| 24.3 | Me | Me | H | Br | Br | H | H | |
| 24.4 | H | Me | H | Br | Br | H | H | |
| 24.5 | Me | Et | H | Br | Br | H | H | |
| 24.6 | Me | Me | Me | F | F | H | H | |
| 24.7 | Me | Me | Me | Cl | Cl | H | H | |
| 24.8 | Me | Me | Me | Br | Br | H | H | |
| 24.9 | Me | Me | H | Cl | Cl | Me | Me | |
| 24.10 | Me | Me | H | Br | Br | Me | Me | |
| 24.11 | Me | Me | H | F | F | H | H | |
| 24.12 | Me | Me | Me | Br | P | H | H | |

TABLE 25

126 compounds No. 25.1 to 25.126 of the formula

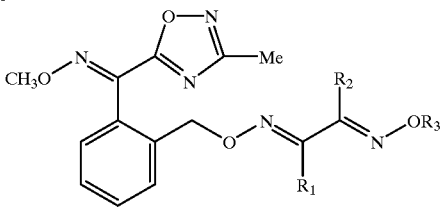

in which
R₁, R₂ and R₃ are as defined for the corresponding compound of Table 1.

TABLE 26

126 compounds No. 26.1 to 26.126 of the formula

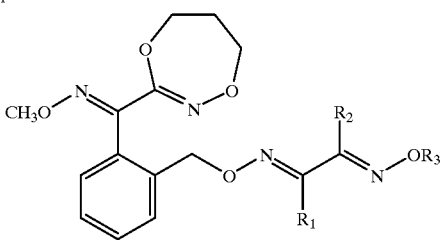

in which
R₁, R₂ and R₃ are as defined for the corresponding compound of Table 1.

TABLE 27

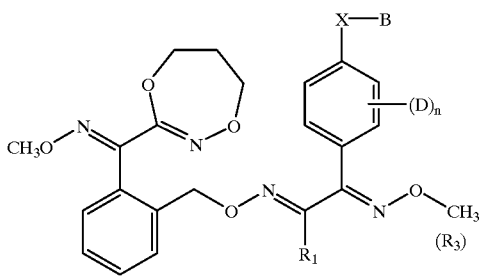

| Example No. | R₁ | X* | n | B or D | Physical data (m.p.) |
|---|---|---|---|---|---|
| 27.1 | Me | — | 1 | 2-Me | |
| 27.2 | Me | — | 1 | 3-Me | |
| 27.3 | Me | — | 1 | 4-Me | |
| 27.4 | Me | — | 1 | 2-CF₃ | |
| 27.5 | Me | — | 1 | 3-CF₃ | |
| 27.6 | Me | — | 1 | 4-CF₃ | |
| 27.7 | Me | — | 1 | 2-Fluoro | |
| 27.8 | Me | — | 1 | 3-Fluoro | |
| 27.9 | Me | — | 1 | 4-Fluoro | |
| 27.10 | Me | — | 1 | 2-Chloro | |
| 27.11 | Me | — | 1 | 3-Chloro | |
| 27.12 | Me | — | 1 | 4-Chloro | |
| 27.13 | Me | — | 1 | 2-Bromo | |
| 27.14 | Me | — | 1 | 3-Bromo | |
| 27.15 | Me | — | 1 | 4-Bromo | |
| 27.16 | Me | — | 1 | 4-Et | |
| 27.17 | Me | — | 1 | 4-tert-Butyl | |
| 27.18 | Me | — | 2 | 2,3-Dimethyl | |
| 27.19 | Me | — | 2 | 2,4-Dimethyl | |
| 27.20 | Me | — | 2 | 2,5-Dimethyl | |
| 27.21 | Me | — | 2 | 2-Me,4-F | |
| 27.22 | Me | — | 2 | 2-Me,5-F | |
| 27.23 | Me | — | 2 | 2-F,5-Me | |
| 27.24 | Me | — | 2 | 3-CF₃,4-Cl | |
| 27.25 | Me | — | 2 | 3-CF₃-Phenoxy | |
| 27.26 | Me | — | 0 | — | |
| 27.27 | CN | — | 0 | — | |
| 27.28 | Me | — | 2 | 3,4-Methylenedioxy | |
| 27.29 | Me | O | 0 | Me | |
| 27.30 | Me | O | 0 | Et | |
| 27.31 | Me | O | 0 | n-Propyl | |
| 27.32 | Me | O | 0 | i-Propyl | resin |
| 27.33 | Me | O | 0 | Allyl | |
| 27.34 | Me | O | 0 | Propargyl | |
| 27.35 | Me | O | 0 | Phenyl | |
| 27.36 | Me | O | 0 | 3-CF₃-Phenyl | |
| 27.37 | Me | O | 0 | 2-Fluorophenyl | |
| 27.38 | Me | O | 0 | 3-Fluorophenyl | |
| 27.39 | Me | O | 0 | 4-Fluorophenyl | |
| 27.40 | Me | O | 0 | 4-Chlorophenyl | |
| 27.41 | Me | O | 0 | 4-Bromophenyl | |
| 27.42 | Me | O | 0 | CF₃ | |
| 27.43 | Me | O | 0 | CHF₂ | |
| 27.44 | Me | O | 0 | CF₂CHF₂ | |
| 27.45 | Me | S | 0 | Me | |
| 27.46 | Me | —SO₂— | 0 | Me | |
| 27.47 | Me | S | 0 | Et | |
| 27.48 | Me | —SO₂— | 0 | Et | |
| 27.49 | Me | S | 0 | n-Propyl | |
| 27.50 | Me | —SO₂— | 0 | n-Propyl | |
| 27.51 | Me | S | 0 | i-Propyl | |
| 27.52 | Me | S | 0 | Phenyl | |
| 27.53 | Me | S | 0 | 2-Pyridyl | |
| 27.54 | Me | S | 0 | 2-Pyrimidinyl | |
| 27.55 | Me | S | 0 | 5-Me-1,3,4-Thiadiazolyl | |
| 27.56 | Me | —OCH₂— | 0 | Phenyl | |
| 27.57 | Me | —OCH₂— | 0 | 3-CF₃-Phenyl | |
| 27.58 | Me | —OCH₂— | 0 | 2-CF₃-Phenyl | |
| 27.59 | Me | —OCH₂— | 0 | 4-CF₃-Phenyl | |

TABLE 27-continued

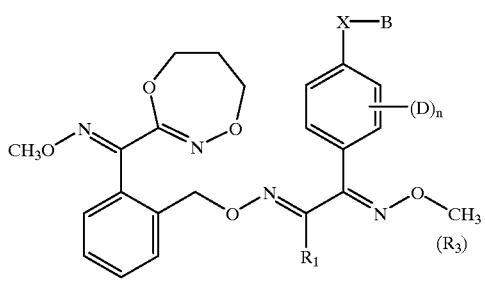

| Example No. | R₁ | X* | n | B or D | Physical data (m.p.) |
|---|---|---|---|---|---|
| 27.60 | Me | —OCH₂— | 0 | 2-F-Phenyl | |
| 27.61 | Me | —OCH₂— | 0 | 3-F-Phenyl | |
| 27.62 | Me | —OCH₂— | 0 | 4-F-Phenyl | |
| 27.63 | Me | —OCH₂— | 0 | 3-Me-Phenyl | |
| 27.64 | Me | OCH₂ | 0 | 3-Cl-Phenyl | |
| 27.65 | Me | OCH₂ | 0 | 3-Br-Phenyl | |
| 27.66 | Me | OCH₂ | 0 | 3-CH₃O-Phenyl | |
| 27.67 | Me | —OCH₂— | 0 | Trimethylsilyl | |
| 4.68 | Me | —OCH₂— | 0 | Cyclohexyl | |
| 4.69 | Me | —OCH₂— | 0 | CF₃ | |
| 27.70 | Me | O | 0 | 4-Me-phenyl | |
| 27.71 | Me | O | 0 | 3-Cl-phenyl | |
| 27.72 | Me | O | 0 | 3-Br-phenyl | |
| 27.73 | Me | — | 2 | 2,4-Di-fluoro | |
| 27.74 | Me | — | 1 | 4-Ethynyl | |
| 27.75 | Me | — | 1 | 4-(3-Methyl-isoxazol-5-yl) | |
| 27.76 | Me | — | 1 | 4-Phenyl | |
| 27.77 | Me | — | 1 | 4-(p-Chlorophenyl) | |
| 27.78 | Me | — | 1 | 2-Methoxy | |
| 27.79 | Me | — | 1 | 4-Trimethyl-silyl | |
| 27.80 | Me | O | 0 | n-Butyl | |
| 27.81 | Me | O | 0 | s-Butyl | |
| 27.82 | Me | O | 0 | i-Butyl | |
| 27.83 | Me | O | 0 | t-Butyl | |
| 27.84 | Me | — | 2 | 2-F,4-Me | |
| 27.85 | Me | O | 0 | 4-t-Butylphenyl | |
| 27.86 | Me | O | 0 | Cyclopentyl | |
| 27.87 | Me | O | 0 | 2,4-Difluorophenyl | |
| 27.88 | Me | O | 0 | 4-F,3-Cl-phenyl | |
| 27.89 | Me | — | 2 | 2-F,4-nPropyloxy | |
| 27.90 | Me | — | 2 | 2-F,4-Ethoxy | |
| 27.91 | Me | — | 2 | 2-Me,4-nPropyloxy | |
| 27.92 | Me | — | 2 | 2-Me,4-Ethoxy | |
| 27.93 | Me | — | 2 | 2-F,4-iPropyloxy | |
| 27.94 | Me | — | 2 | 2,4-Dimethoxy | |
| 27.95 | Me | — | 2 | 2-F,4-Methoxy | |
| 27.96 | Me | — | 2 | 2-F,4-nButyloxy | |
| 27.97 | Me | — | 2 | 2-F,4-sButyloxy | |
| 27.98 | Me | — | 2 | 2-F,4-iButyloxy | |
| 27.99 | Me | — | 2 | 2-F,4-Cyclopentyloxy | |
| 27.100 | Me | — | 2 | 2-Me,4-Methoxy | |
| 27.101 | Me | — | 2 | 2-Me,4-iPropyloxy | |
| 27.102 | Me | — | 2 | 2-Me,4-nButyloxy | |
| 27.103 | Me | — | 2 | 2-Me,4-sButyloxy | |
| 27.104 | Me | — | 2 | 2-Me,4-iButyloxy | |
| 27.105 | Me | — | 2 | 2-Me,4-Cyclopentyloxy | |
| 27.106 | Me | — | 2 | 2-F,4-(2,2-Dichlorocyclo-propylmethoxy) | |
| 27.107 | Me | — | 2 | 2-Me,4-(2,2-Dichlorocyclo-propylmethoxy) | |
| 27.108 | Me | — | 2 | 2-Methoxy,4-F | |
| 27.109 | Me | — | 2 | 2-Methoxy,4-Me | |

TABLE 28

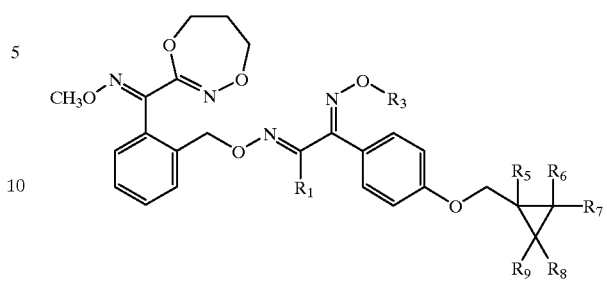

| Example No. | R₁ | R₃ | R₅ | R₆ | R₇ | R₈ | R₉ | Physical data |
|---|---|---|---|---|---|---|---|---|
| 28.1 | Me | Me | H | H | H | H | H | |
| 28.2 | Me | Me | H | Cl | Cl | H | H | |
| 28.3 | Me | Me | H | Br | Br | H | H | |
| 28.4 | H | Me | H | Br | Br | H | H | |
| 28.5 | Me | Et | H | Br | Br | H | H | |
| 28.6 | Me | Me | Me | F | F | H | H | |
| 28.7 | Me | Me | Me | Cl | Cl | H | H | |
| 28.8 | Me | Me | Me | Br | Br | H | H | |
| 28.9 | Me | Me | H | Cl | Cl | Me | Me | |
| 28.10 | Me | Me | H | Br | Br | Me | Me | |
| 28.11 | Me | Me | H | F | F | H | H | |
| 28.12 | Me | Me | Me | Br | F | H | H | |

TABLE 29

109 compounds No. 29.1 to 29.109 of the formula

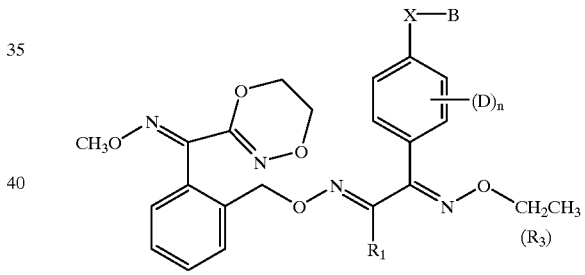

in which
R₁, X, n, B and D are as defined for the corresponding compounds in Table 4.

TABLE 30

109 compounds No. 30.1 to 30.109 of the formula

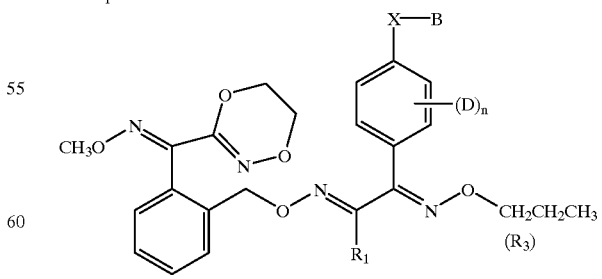

in which
R₁, X, n, B and D are as defined for the corresponding compound in Table 4.

TABLE 31

109 compounds No. 31.1 to 31.109 of the formula

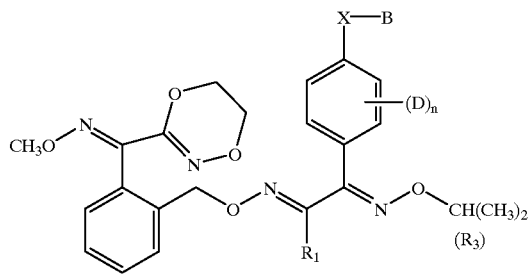

in which
$R_1$, X, n, B and D are as defined for the corresponding compound in Table 4.

TABLE 32

109 compounds No. 32.1 to 32.109 of the formula

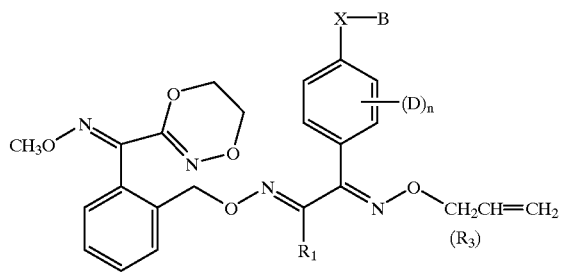

in which
$R_1$, X, n, B and D are as defined for the corresponding compound in Table 4.

TABLE 33

109 compounds No. 33.1 to 33.109 of the formula

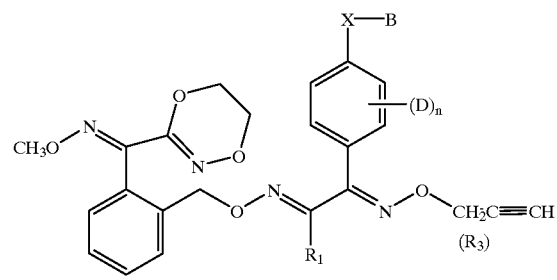

in which
$R_1$, X, n, B and D are as defined for the corresponding compound in Table 4.

TABLE 34

109 compounds No. 34.1 to 34.109 of the formula

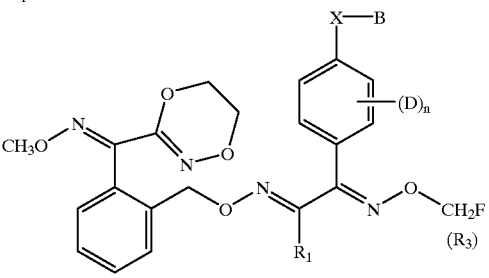

in which
$R_1$, X, n, B and D are as defined for the corresponding compound in Table 4.

Formulation Examples for Active Compounds of the Formula I

Examples F-1.1 to F-1.3

Emulsion concentrates

| Constituents | F-1.1 | F-1.2 | F-1.3 |
|---|---|---|---|
| Active compound from Table 1-34 | 25% | 40% | 50% |
| Calcium dodecylbenzenesulfonate | 5% | 8% | 6% |
| Castor oil polyethylene glycol ether (36 mol of ethylenoxy units) | 5% | — | — |
| Tributylphenol polyethylene glycol ether (30 mol of ethylenoxy units) | — | 12% | 4% |
| Cyclohexanone | — | 15% | 20% |
| Xylene mixture | 65% | 25% | 20% |

Emulsions of any desired dilution can be prepared from these emulsion concentrates with water.

Example F-2

Emulsion concentrate

| Constituents | F-2 |
|---|---|
| Active compound from Table 1-34 | 10% |
| Octylphenol polyethylene glycol ether (4 to 5 mol of ethylenoxy units) | 3% |
| Calcium dodecylbenzenesulfonate | 3% |
| Castor oil polyglycol ether (36 mol of ethylenoxy units) | 4% |
| Cyclohexanone | 30% |
| Xylene mixture | 50% |

Emulsions of any desired dilution can be prepared from this emulsion concentrate with water.

Examples F-3.1 to F-3.4

Solutions

| Constituents | F-3.1 | F-3.2 | F-3.3 | F-3.4 |
|---|---|---|---|---|
| Active compound from Table 1-34 | 80% | 10% | 5% | 95% |
| Propylene glycol monomethyl ether | 20% | — | — | — |
| Polyethylene glycol | — | 70% | — | — |

-continued

| Constituents | F-3.1 | F-3.2 | F-3.3 | F-3.4 |
|---|---|---|---|---|
| (relative molecular weight: 400 atomic mass units) | | | | |
| N-Methylpyrrolid-2-one | — | 20% | — | — |
| Epoxidized coconut oil | — | — | 1% | 5% |
| Benzine (boiling limits: 160–190°) | — | — | 94% | — |

The solutions are suitable for use in the form of tiny drops.

Examples F-4.1 to F-4.4
Granules

| Constituents | F-4.1 | F-4.2 | F-4.3 | F-4.4 |
|---|---|---|---|---|
| Active compound from Table 1-34 | 5% | 10% | 8% | 21% |
| Kaolin | 94% | — | 79% | 54% |
| Highly disperse silicic acid | 1% | — | 13% | 7% |
| Attapulgite | — | 90% | — | 18% |

The active compound according to the invention is dissolved in methylene chloride, the solution is sprayed onto the carrier and the solvent is then evaporated off in vacuo.

Examples F-5.1 and F-5.2
Dusts

| Constituents | F-5.1 | F-5.2 |
|---|---|---|
| Active compound from Table 1-34 | 2% | 5% |
| Highly disperse silicic acid | 1% | 5% |
| Talc | 97% | — |
| Kaolin | — | 90% |

Ready-to-use dusts are obtained by intimate mixing of all the constituents.

Examples F-6.1 to F-6.3
Wettable powders

| Constituents | F-6.1 | F-6.2 | F-6.3 |
|---|---|---|---|
| Active compound from Table 1-34 | 25% | 50% | 75% |
| Sodium ligninsulfonate | 5% | 5% | — |
| Sodium lauryl sulfate | 3% | — | 5% |
| Sodium diisobutylnaphthalenesulfonate | — | 6% | 10% |
| Octylphenol polyethylene glycol ether (7 to 8 mol of ethyleneoxy units) | — | 2% | — |
| Highly disperse silicic acid | 5% | 10% | 10% |
| Kaolin | 62% | 27% | — |

Example F-7
Wettable powder
Active compound from Table 1-34 25%
Sodium ligninsulfonates 5%
Kieselguhr 25%
Sodium carbonate 5%
Disodium 1-benzyl-2-heptadecylbenzimidazole-5%
X,X'-disulfonic acid (including 15–30% of $Na_2SO_4$)
Champagne chalk 35%

All the constituents are mixed and the mixture is ground thoroughly in a suitable mill. Wettable powders which can be diluted with water to give suspensions of any desired concentration are obtained.

Biological Examples
A. Microbicidal actions
A-1: Action against *Puccinia graminis* on wheat
a) Residual protective action 6 days after sowing, wheat plants are sprayed dripping wet with an aqueous spray liquor (0.02% of active substance) prepared from a wettable powder of the active compound, and 24 hours later are infected with a uredospore suspension of the fungus. After an incubation time of 48 hours (conditions: 95 to 100% relative atmospheric humidity at 20° C.), the plants are placed in a greenhouse at 22° C. The fungal infestation is evaluated 12 days after the infection.

b) Systemic action 5 days after sowing, an aqueous spray liquor (0.006% of active substance, based on the volume of soil) prepared from a wettable powder of the active compound is poured onto wheat plants. It is ensured here that the spray liquor does not come into contact with the above-ground parts of the plants. 48 hours later, the plants are infected with a uredospore suspension of the fungus. After an incubation time of 48 hours (conditions: 95 to 100% relative atmospheric humidity at 20° C.), the plants are placed in a greenhouse at 22° C. The fungal infestation is evaluated 12 days after the infection.

Compounds from the tables show t good action. The infestation is as a rule suppressed to 10% or less.

Example A-2
Action against Phytophthora infestans on tomatoes
a) Residual protective action After growing for three weeks, tomato plants are sprayed dripping wet with an aqueous spray liquor (0.02% of active substance) prepared from a wettable powder of the active compound, and 24 hours later are infected with a sporangia suspension of the fungus. The fungal infestation is evaluated 5 days after the infection, during which 90 to 100% relative atmospheric humidity and a temperature of 20° C. are maintained.

b) Systemic action

After growing for 3 weeks, an aqueous spray liquor (0.006% of active substance, based on the volume of soil) prepared from a wettable powder of the active compound is poured onto tomato plants. It is ensured here that the spray liquor does not come into contact with the above-ground parts of the plants. After 48 hours, the plants are infected with a sporangia suspension of the fungus. The fungal infestation is evaluated 5 days after the infection, during which 90 to 100% relative atmospheric humidity and a temperature of 20° C. are maintained.

Compounds from the tables show a good action.

Example A-3
Residual protective action against *Cercospora arachidicola* on groundnuts Groundnut plants 10 to 15 cm high are sprayed dripping wet with an aqueous spray liquor (0.02% of active substance) prepared from a wettable powder of the active compound, and 48 hours later are infected with a conidia suspension of the fungus. The plants are incubated at 21° C. and a high atmospheric humidity for 72 hours and then placed in a greenhouse until the typical leaf spots occur. The action of the active substance is evaluated 12 days after infection on the basis of the number and size of the leaf spots.

Compounds from the tables show a good action.

Example A-4
Action against *Plasmopara viticola* on beet

Beet seedlings in the 4 to 5 leaf stage are sprayed dripping wet with an aqueous spray liquor (0.02% of active substance) prepared from a wettable powder of the active compound, and 24 hours later are infected with a sporangia suspension of the fungus. The fungal infestation is evaluated 6 days after infection, during which 95 to 100% relative atmospheric humidity and a temperature of 20° C. are maintained.

Compounds from the tables show a good action.

Example A-5
Action against *Colletotrichum lagenarium* on cucumbers

After growing for 2 weeks, cucumber plants are sprayed with a spray liquor (concentration 0.002%) prepared from a wettable powder of the active compound. After 2 days, the plants are infected with a spore suspension ($1.5 \times 10^5$ spores/ml) of the fungus and are incubated for 36 hours at 23° C. at a high atmospheric humidity. The incubation is then continued under normal atmospheric humidity at about 22° C. The fungal infestation which has occurred is evaluated 8 days after the infection.

Compounds from the tables show a good action.

Example A-6
Residual protective action against *Venturia inaegualis* on apples Apple seedlings with fresh shoots 10 to 20 cm long are sprayed dripping wet with an aqueous spray liquor (0.02% of active substance) prepared from a wettable powder of the active compound, and 24 hours later are infected with a conidia suspension of the fungus. The plants are incubated for 5 days at 90 to 100% relative atmospheric humidity and placed in a greenhouse at 20 to 24° C. for a further 10 days. The fungal infestation is evaluated 12 days after the infection.

Compounds from the tables show a good action.

Example A-7
Action against *Erysiphe graminis* on barley a) Residual protective action Barley plants approximately 8 cm high are sprayed dripping wet with an aqueous spray liquor (0.02% of active substance) prepared from a wettable powder of the active compound, and 3 to 4 hours later are dusted with conidia of the fungus. The infected plants are placed in a greenhouse at 22° C. The fungal infestation is evaluated 12 days after the infection.

Compounds from the tables show a good action.

b) Systemic action

An aqueous spray liquor (0.002% of active substance, based on the volume of soil) prepared from a wettable powder of the active compound is poured onto barley plants approximately 8 cm high. It is ensured here that the spray liquor does not come into contact with the above-ground parts of the plants. 48 hours later, the plants are dusted with conidia of the fungus. The infected plants are placed in a greenhouse at 22° C. The fungal infestation is evaluated 12 days after the infection.

Compounds from the tables show t very good action. The infestation is suppressed to 10 to 0%.

Example A-8
Action against *Podosphaera leucotricha* on apple shoots

Apple seedlings with fresh shoots about 15 cm long are sprayed with a spray liquor (0.06% of active substance). After 24 hours, the treated plants are infected with a conidia suspension of the fungus and placed in a climatically controlled chamber at 70% relative atmospheric humidity at 20° C. The fungal infestation is evaluated 12 days after the infection.

Compounds from the tables show a good action.

Example A-9
Action against *Pythium debaryanum* on sugar beet (Beta vulgaris)

a) Action after soil application

The fungus is cultured on sterile oat grains and admixed to an earth/sand mixture. Flowerpots are filled with the earth infected in this way and the earth is sown with sugar beet seeds. Immediately after sowing, the test preparations, formulated as wettable powders, are poured over the earth as an aqueous suspension (20 ppm of active compound, based on the volume of earth). The pots are then placed in a greenhouse at 20–24° C. for 2–3 weeks. The earth is constantly kept uniformly moist by spraying lightly with water. For the evaluation of the test, the emergence of the sugar beet plants and the proportion of healthy and sick plants are determined.

b) Action after dressing application

The fungus is cultured on sterile oat grains and admixed to an earth/sand mixture. Flowerpots are filled with the earth infected in this way and the earth is sown with sugar beet seeds which have been dressed with the test preparations, formulated as a dressing powder (1000 ppm of active compounds, based on the weight of seed). The sown pots are placed in a greenhouse at 20–24° C. for 2–3 weeks. The earth is constantly kept uniformly moist by spraying lightly with water. In the evaluation of the test, the emergence of the sugar beet plants and the proportion of healthy and sick plants are determined. After the treatment with active compounds of the formula I, more than 80% of the plants emerge and have a healthy appearance. In the control pots, only isolated emerged plants with a sickly appearance are observed.

Example A-10
Action against *Pyricularia oryzae* on rice a) Residual protective action After growing for two weeks, rice plants are sprayed dripping wet with an aqueous spray liquor (0.02% of active substance), and 48 hours later are infected with a conidia suspension of the fungus. The fungal infestation is evaluated 5 days after infection, during which 95 to 100% relative atmospheric humidity and a temperature of 22° C. are maintained.

b) Systemic action

An aqueous spray liquor (0.006% of active substance, based on the volume of soil) is poured onto rice plants 2 weeks old. It is ensured here that the spray liquor does not come into contact with above-ground parts of the plants. The pots are then filled with water to the extent that the lowest parts of the stems of the rice plants are standing in the water. After 96 hours, the plants are infected with a conidia suspension of the fungus and kept at 95 to 100% relative atmospheric humidity and a temperature of 24° C. for 5 days.

Compounds of the formula I mostly prevent the outbreak of the disease on the infected plants.

Example A-11
Action against *Botrytis cinerea* on apple fruits. Residual protective action Artificially damaged apples are treated by dripping a spray liquor (0.02% of active substance) on the damaged areas. The treated fruits are then inoculated with a spore suspension of the fungus and incubated for one week at a high atmospheric humidity and about 20° C. The fungicidal action of the test substance is deduced from the number of rotting damaged areas.

Active compounds of the formula I from the tables are capable of preventing the spread of the rot, in some cases completely.

Example A-12
Action against *Helminthosporium gramineum*

Wheat grains are contaminated with a spore suspension of the fungus and allowed to dry. The contaminated grains are dressed with a suspension of the test substance (600 ppm of active compound, based on the weight of the seed). After two days, the grains are laid out on suitable agar dishes, and after a further 4 days the development of the fungal colonies around the grains is evaluated. The number and size of the fungal colonies are used to evaluate the test substance.

Compounds of the formula I in some cases show a good action, i.e. inhibition of the fungal colonies.

Example A-13
Action against *Fusarium nivale* on rye

Rye of the variety Tetrahell naturally infected with *Fusarium nivale* is dressed on a mixing roll with the fungicide to be tested, the following concentrations being used: 20 or 6 ppm of AS (based on the weight of the seed). The infected and treated rye is sown in October in the open with a sowing machine on plots of 3 m length and 6 seed rows. Three repeats per concentration. Until evaluation of the infestation, the test crop is cultivated under normal field conditions (preferably in a region with a continuous covering of snow during the winter months).

To evaluate the phytotoxicity, the emergence of the seeds in autumn and the crop density/stand density in spring are rated.

To determine the activity of the active compound, the percentage proportion of plants infested by Fusarium is counted in the spring immediately after the snow has melted. The number of plants infested was less than 5% in the present case. The plants which had emerged had a healthy appearance.

Example A-14
Action against *Septoria nodorum* on wheat

Wheat plants are sprayed in the 3-leaf stage with a spray liquor (60 ppm of AS prepared from a wettable powder of the active substances. After 24 hours, the treated plants are infected with a conidia suspension of the fungus. The plants are then incubated for 2 days at 90–100% relative atmospheric humidity and placed in a greenhouse at 20–24° C. for a further 10 days. The fungal infestation is evaluated 13 days after the infection. Less than 1% of the wheat plants show infestation.

Example A-15
Action against *Rhizoctonia solani* on rice
Protective local soil application A suspension (spray liquor) prepared from the formulated test substance is poured onto rice plants 10 days old, without contaminating above-ground parts of the plant. Infection is carried out three days later by placing one straw of barley infected with Rhizoctonia solani per pot between rice plants. After incubation for 6 days in a climatically controlled room at a daytime temperature of 29° C. and a night-time temperature of 26° C. and 95% relative atmospheric humidity, the fungal infestation is evaluated. Less than 5% of the rice plants showed any infestation. The plants had a healthy appearance.

Protective local leaf application

Rice plants 12 days old are sprayed with a suspension prepared from formulated test substances. Infection is carried out one day later by placing one straw of barley infected with *Rhizoctonia solani* per pot between the rice plants. After incubation for 6 days in a climatically controlled room at a daytime temperature of 29° C. and a night-time temperature of 26° C. and 95% relative atmospheric humidity, the plants are rated. Untreated but infected control plants show a fungal infestation of 100%. Compounds of the formula I in some cases cause complete inhibition of the disease infestation.

Example A-16
Action against Phytophthora on potato plants

Residual protective action: After growing for 3 weeks, potato plants (variety Bintje) 2 to 3 weeks old are sprayed with a spray liquor (0.02% of active substance) prepared from a wettable powder of the active compound. After 24 hours, the treated plants are infected with a spore suspension of the fungus. The fungal infestation is evaluated after incubation of the infected plants for 5 days at 90–100%, relative atmospheric humidity and 20° C. Compounds of the formula I from the tables show a lasting action (less than 20% fungal infestation). Untreated but infected control plants show a Phytophthora infestation of 100%.

Biological Examples

B. Insecticidal actions

Example B-17
Action against *Aphis craccivora*

Pea seedlings are infected with *Aphis craccivora*, subsequently sprayed with a spray liquor comprising 400 ppm of active compound, and then incubated at 20°. 3 and 6 days later, the percentage reduction in the population (% action) is determined by comparison of the number of dead aphids on the treated and on the untreated plants.

Compounds of the tables show a good action in this test, i.e. a destruction rate of more than 80%.

Example B-18
Action against *Diabrotica balteata*

Maize seedlings are sprayed with an aqueous emulsion spray liquor comprising 400 pm of active compound and, after the spray coating has dried on, are populated with 10 larvae of the second stage of *Diabrotica balteata* and then placed in plastic containers. 6 days later, the percentage reduction in the population (% action) is determined by comparison of the number of dead larvae between the treated and untreated plants.

Compounds of the tables show a good action in this test.

Example B-19
Action against *Heliothis virescens*

Young soya plants are sprayed with an aqueous emulsion spray liquor comprising 400 ppm of active compound and, after the spray coating has dried on, are populated with 10 caterpillars of the first stage of *Heliothis virescens* and then placed in a plastic container. 6 days later, the percentage reduction in the population and the feeding damage (% action) are determined by comparison of the number of dead caterpillars and of the feeding damage between the treated and untreated plants.

71

Compounds of the tables show a good action in this test.

Example B-20
Action against *Spodoptera littoralis*

Young soya plants are sprayed with an aqueous emulsion spray liquor comprising 400 ppm of active compound and, after the spray coating has dried on, are populated with 10 caterpillars of the third stage of *Spodoptera littoralis* and then placed in a plastic container. 3 days later, the percentage reduction in the population and the percentage reduction in the feeding damage (% action) are determined by comparison of the number of dead caterpillars and of the feeding damage between the treated and untreated plants.

Compounds of the tables show a good action in this test.

B-21
Action against *Nilaparvata lugens*

Rice plants are treated with an aqueous emulsion spray liquor which comprises 400 ppm of the active compound. After the spray coating has dried on, the rice plants are populated with cicada larvae of the 2nd and 3rd stage. The evaluation is carried out 21 days later. The percentage reduction in the population (% action) is determined by comparison of the number of surviving cicadas on the treated plants to those on the untreated plants.

The compounds of the tables show an action of more than 90%.

B-22
Action against *Plutella xylostella* caterpillars

Young cabbage plants are sprayed with an aqueous emulsion spray liquor comprising 400 ppm of the active compound. After the spray coating has dried on, the cabbage plants are populated with 10 caterpillars of the 3rd stage of *Plutella xylostella* and placed in a plastic container. The evaluation is carried out 3 days later. The percentage reduction in the population and the percentage reduction in the feeding damage (% action) are determined by comparison of the number of dead caterpillars and of the feeding damage on the treated plants to those on the untreated plants.

Compounds from the tables show a good action.

Example B-23
Action against *Musca domestica*

A sugar cube is treated with a solution of the test substance such that the concentration of test substance, after drying overnight, in the sugar is 250 ppm. This treated cube is placed on an aluminium dish with a wet cotton-wool swab and 10 adult *Musca domestica* of an OP resistant strain, covered with a glass beaker and incubated at 25° C. After 24 hours, the mortality rate is determined.

Compounds from the tables show a good action.

Biological Examples
C. Acaricidal actions

C-24: Action against *Tetranychus urticae*

Young bean plants are populated with a mixed population of *Tetranychus urticae*, and one day later are sprayed with an aqueous emulsion spray liquor comprising 400 ppm of the active compound. The plants are then incubated for 6 days at 25° C. and thereafter evaluated. The percentage reduction in the population (% action) is determined by comparison of the number of dead eggs, larvae and adults on the treated plants to those on the untreated plants.

Compounds from the tables show a good action.

C-25: Action on mixed populations of *Tetranychus cinnabarinus*

Dilution series

Dwarf beans in the 2-leaf stage are populated with a mixed population (eggs, larvae/nymphs, adults) of an OP-tolerant *Tetranychus cinnabarinus* strain. 24 hours after the infection, the products are applied to the plants with dosages of 200, 100 and 50 mg of AS/l in the automatic spray booth. The substances are formulated and are diluted with water to the corresponding dosages. The test is evaluated 2 and 7 days after the application for percentage mortality with respect to eggs, larvae/nymphs and adults. Compounds of the tables show a mortality of more than 70% in dilutions up to 50 mg of AS/litre.

C-26: Action against *Boophilus microplus*

Fully satiated adult female ticks are glued to a PVC plate and covered with a cotton-wool swab, and 10 ml of aqueous test solution comprising 125 ppm of active compound are poured over. The cotton-wool swab is removed and the ticks are incubated for 4 weeks until oviposition. The action manifests itself either as mortality or sterility among the females or as an ovicidal action in the eggs.

What is claimed is:

1. A compound of the formula I

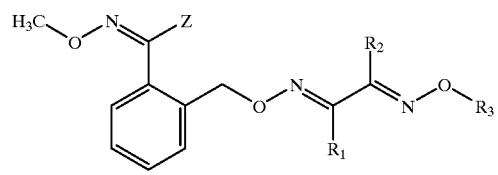

or isomer or isomer mixture thereof, in which a)

Z is a group 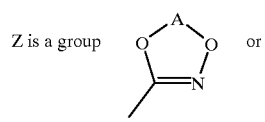 or b)

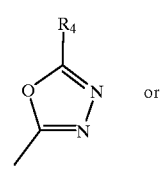 or c)

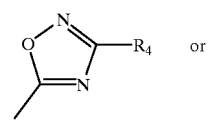 or d)

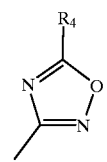

and

A is alkanediyl which is unsubstituted or substituted by methyl and has 1 to 3 carbon atoms;

$R_4$ is hydrogen, $C_1$–$C_3$alkyl, cyclopropyl or $CF_3$;

$R_1$ is hydrogen, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or cyano;

$R_2$ Ls hydrogen, $C_1$–$C_6$alkyl, $C_3$–$C_6$cycloalkyl, cyano, substituted or unsubstituted $C_1$–$C_6$alkoxycarbonyl, substituted or unsubstituted di-($C_1$–$C_6$alkyl)aminocarbonyl, substituted or unsubstituted heteroaryl, substituted or unsubstituted heterocyclyl, naphthyl;

a group 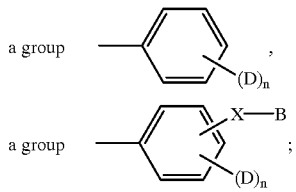

D is identical or different halogen, $C_1$–$C_4$alkyl, $C_1$–$C_6$alkoxy, $C_1$–$C_2$haloalkyl, $C_1$–$C_2$haloalkoxy, $C_3$–$C_6$alkenyloxy, $C_3$–$C_6$alkynyloxy, $C_1$–$C_4$alkylenedioxy, $C_3$–$C_6$-cycloalkyl, $C_1$–$C_4$-alkoximino-$C_1$–$C_2$alkyl, $C_1$–$C_8$-alkiminoxy, cyanomethoxy, cyano-$C_1$–$C_2$alkoxy, cyano, nitro, thioamido, thiocyanatomethyl, $C_1$–$C_4$alkoxy-$C_1$–$C_2$alkoxy, halo-$C_1$–$C_6$alkylsulfonyl, di-$C_1$–$C_4$alkylamino-$C_1$–$C_4$alkoxy, $C_2$–$C_4$alkynyl, substituted or unsubstituted phenyl, substituted or unsubstituted heteroaryl, tri($C_1$–$C_4$alkyl)silyl or di($C_1$–$C_4$alkyl)phenylsilyl;

n is 0, 1, 2, 3 or 4;

X is —O—, —O—($C_1$–$C_4$alkyl)—, —($C_1$–$C_4$alkyl)—O—, —S(O)$_m$—, —($C_1$–$C_4$alkyl)—S(O)$_m$— or —S(O)$_m$ —($C_1$–$C_4$-alkyl)—;

m is 0, 1 or 2;

B is $C_1$–$C_6$alkyl, halo-$C_1$–$C_6$alkyl, $C_3$–$C_6$cycloalkyl, $C_2$–$C_6$alkenyl which is unsubstituted or substituted by 1 to 3 halogen atoms or $C_3$–$C_6$alkynyl, or aryl, heteroaryl or heterocyclyl, all three of which independently of one another are unsubstituted or substituted one to five times by $C_1$–$C_6$alkyl, halo-$C_1$–$C_6$alkyl, halogen, $C_1$–$C_6$alkoxy or halo-$C_1$–$C_6$alkoxy, tri($C_1$–$C_4$alkyl)silyl, di($C_1$–$C_4$alkyl)phenylsilyl or a group

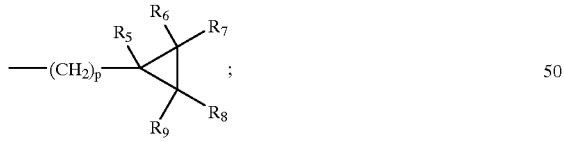

$R_5$, $R_6$, $R_7$, $R_8$ and $R_9$ independently of one another are hydrogen, $C_1$–$C_4$alkyl or halogen, p is 0, 1, 2 or 3; and $R_3$ is hydrogen, $C_1$–$C_6$alkyl, $C_1$–$C_7$haloalkyl having 1 to 5 halogen atoms, $C_1$–$C_4$alkoxy-$C_1$–$C_2$alkyl, $C_2$–$C_6$alkenyl which is unsubstituted or substituted by 1 to 3 halogen atoms, $C_2$–$C_6$alkynyl, $C_3$–$C_6$cycloalkyl which is unsubstituted or substituted by 1 to 4 halogen atoms, $C_3$–$C_6$cycloalkyl-$C_1$–$C_4$alkyl which is unsubstituted or substituted by 1 to 4 halogen atoms, cyano-$C_1$–$C_4$alkyl, $C_1$–$C_4$alkoxycarboriyl-$C_1$–$C_2$alkyl, phenyl-$C_1$–$C_3$alkyl which is unsubstituted or substituted by halogen, $C_1$–$C_3$alkyl, $C_1$–$C_4$alkoxy, $C_1$–$C_4$haloalkyl, cyano, nitro or $C_1$–$C_4$alkylenedioxy, where the phenyl group can be substituted one to three times in an identical or different manner; phenyl which is unsubstituted or substituted once or twice, independently of one another, by $C_1$–$C_4$alkyl, $C_1$–$C_4$alkoxy, halogen, $C_1$–$C_2$haloalkyl having 1 to 3 halogen atoms, nitro or cyano; or pyridyl which is unsubstituted or substituted once or twice, independently of one another by $C_1$–$C_4$alkyl, $C_1$–$C_4$alkoxy, halogen, $C_1$–$C_2$haloalkyl having 1 to 3 halogen atoms, nitro or cyano.

2. The compound of the formula I according to claim 1 in which

A is alkanediyl which is unsubstituted or substituted by methyl and has 1 to 3 carbon atoms;

$R_4$ is hydrogen, $C_1$–$C_3$alkyl, cyclopropyl or $CF_3$;

$R_1$ is hydrogen, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or cyano;

$R_2$ i hydrogen, $C_1$–$C_6$alkyl, $C_3$–$C_6$cycloalkyl, cyano, substituted or unsubstituted $C_1$–$C_6$alkoxycarbonyl, substituted or unsubstituted di-($C_1$–$C_6$alkyl)aminocarbonyl, substituted or unsubstituted heteroaryl, substituted or unsubstituted heterocyclyl or naphthyl;

a group or a group

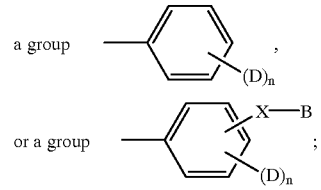

D is identical or different halogen, $C_1$–$C_4$alkyl, $C_1$–$C_6$alkoxy, $C_1$–$C_2$haloalkyl, $C_1$–$C_2$haloalkoxy, $C_3$–$C_6$alkenyloxy, $C_3$–$C_6$alkynyloxy, $C_1$–$C_4$alkylenedioxy, cyano or nitro, $C_2$–$C_4$alkynyl, substituted or unsubstituted phenyl or substituted or unsubstituted heteroaryl;

n is 0, 1, 2, 3 or 4;

X is —O—, —O—($C_1$–$C_4$alkyl)—, —($C_1$–$C_4$alkyl)—O—, —S(O)$_m$—, —($C_1$–$C_4$alkyl)—S(O)$_m$— or —S(O)$_m$ —($C_1$–$C_4$-alkyl)—;

m is 0, 1 or 2;

B is $C_1$–$C_6$alkyl, halo-$C_1$–$C_6$alkyl, $C_3$–$C_6$cycloalkyl, $C_2$–$C_6$alkenyl which is unsubstituted or substituted by 1 to 3 halogen atoms or $C_3$–$C_6$alkynyl, or aryl, heteroaryl or heterocyclyl, all three of which independently of one another are unsubstituted or substituted one to five times by $C_1$–$C_6$alkyl, halo-$C_1$–$C_6$alkyl, halogen, $C_1$–$C_6$alkoxy or halo-$C_1$–$C_6$alkoxy, tri($C_1$–$C_4$alkyl)silyl, di($C_1$–$C_4$alkyl)phenylsilyl or a group

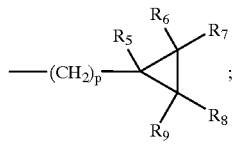

$R_5$, $R_6$, $R_7$, $R_8$ and $R_9$ independently of one another are hydrogen, $C_1$–$C_4$alkyl or halogen, p is 0, 1, 2 or 3; and $R_3$ is hydrogen, $C_1$–$C_6$alkyl, $C_1$–$C_7$haloalkyl having 1 to 5 halogen atoms, $C_1$–$C_4$alkoxy-$C_1$–$C_2$alkyl, $C_2$–$C_6$alkenyl which is unsubstituted or substituted by 1 to 3 halogen atoms, $C_2-C_6$alkynyl, $C_3-C_6$cycloalkyl which is unsubstituted or substituted by 1 to 4 halogen atoms, $C_3-C_6$cycloalkyl-$C_1-C_4$alkyl which is unsubstituted or substituted by 1 to 4 halogen atoms, cyano-$C_1-C_4$alkyl, $C_1-C_4$alkoxycarbonyl-$C_1-C_2$alkyl, phenyl-$C_1-C_3$alkyl which is unsubstituted or substituted by halogen, $C_1-C_3$alkyl, $C_1-C_4$alkoxy, $C_1-C_4$haloalkyl, cyano, nitro or $C_1-C_4$alkylenedioxy, where the phenyl group can be substituted one to three times in an identical or different manner; phenyl which is unsubstituted or substituted once or twice, independently of one another, by $C_1-C_4$alkyl, $C_1-C_4$alkoxy, halogen, $C_1-C_2$haloalkyl having 1 to 3 halogen atoms, nitro or cyano; or pyridyl which is unsubstituted or substituted once or twice, independently of one another by $C_1-C_4$alkyl, $C_1-C_4$alkoxy, halogen, $C_1-C_2$haloalkyl having 1 to 3 halogen atoms, nitro or cyano.

3. The compound according to claim 2, in which Z is a group a).

4. The compound according to claim 3 in which A is ethane-1,2-diyl and $R_1$ is $C_1-C_4$alkyl or cyclopropyl;

$R_2$ is $C_1-C_4$alkyl, $C_1-C_4$alkoxycarbonyl, heteroaryl or a group

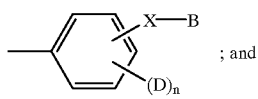 ; and and $R_3$ is $C_1-C_4$alkyl, $C_2-C_4$alkenyl which is unsubstituted or substituted by 1 to 3 halogen atoms, $C_1-C_4$haloalkyl or $C_3-C_4$alkynyl.

5. The compound according to claim 4, in which A is ethane-1,2-diyl and $R_1$ is $C_1-C_4$alkyl or cyclopropyl;

$R_2$ is $C_1-C_4$alkyl, $C_1-C_4$alkoxycarbonyl, heteroaryl or a group

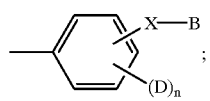 ;

and $R_3$ is $C_1-C_4$alkyl, $C_2-C_4$alkenyl which is unsubstituted or substituted by 1 to 3 halogen atoms.

6. The compound according to claim 5, in which $R_2$ is heteroaryl.

7. The compound according to claim 6, in which $R_2$ is 2-pyridine.

8. The compound according to claim 5, in which $R_2$ is a group

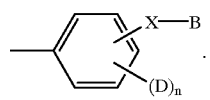.

9. The compound according to claim 8, in which D is identical or different and is fluorine, chlorine or bromine, n is 0, 1 or 2, and X is —O—, —O—($C_1-C_4$alkyl)— or —($C_1-C_4$alkyl)—O—.

10. The compound according to claim 2, in which Z is a group b) and $R_1$ is hydrogen, $C_1-C_4$alkyl or cyclopropyl.

11. The compound of the formula I according to claim 10, in which $R_4$ is hydrogen or methyl; and $R_2$ is hydrogen, $C_1-C_4$alkyl, cyclopropyl, heteroaryl, a group

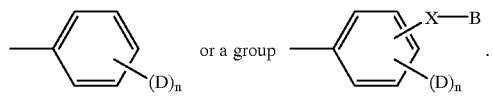.

12. The compound according to claim 11, in which $R_4$ is hydrogen or methyl;

$R_2$ is hydrogen, $C_1-C_4$alkyl, cyclopropyl, heteroaryl, a group

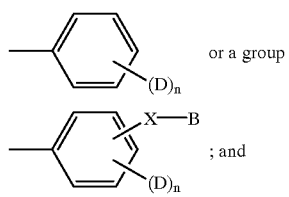 ; and $R_3$ is $C_1-C_4$alkyl, $C_2-C_4$alkenyl which is unsubstituted or substituted by 1 to 3 halogen atoms, $C_1-C_4$haloalkyl or $C_3-C_4$alkynyl.

13. The compound according to claim 11, in which $R_4$ is hydrogen.

14. The compound according to claim 13, in which $R_2$ is heteroaryl.

15. The compound according to claim 11, in which $R_2$ is a group

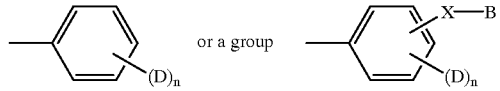

and

D is identical or different and is fluorine, chlorine or bromine, $C_1-C_4$alkyl or $C_1-C_3$alkoxy, n is 0, 1 or 2, and X is —O—, —O—($C_1-C_4$alkyl)— or —($C_1-C_4$alkyl)—O—.

16. The compound of the formula I according to claim 2, in which Z is a group c) and $R_1$ is $C_1-C_4$alkyl or cyclopropyl.

17. The compound according to claim 16, in which $R_4$ is hydrogen; and $R_2$ is hydrogen, $C_1-C_4$alkyl, cyclopropyl, heteroaryl, a group

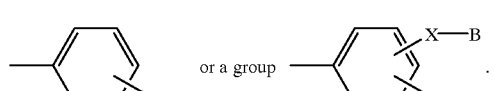.

18. The compound according to claim 17, in which $R_2$ is heteroaryl.

19. The compound of the formula I according to claim 17, in which $R_2$ is a group and D is identical or different and is fluorine, chlorine or bromine, $C_1$–$C_4$alkyl or $C_1$–$C_3$alkoxy, n is 0, 1 or 2, and X is —O—, —O—($C_1$–$C_4$alkyl)— or —($C_1$–$C_4$alkyl)—O—.

20. The compound according to claim 1 in which the $CH_3ON=C$ double bond has the E form.

21. A composition for controlling pests comprising a fungicidally effective amount of the compound according to claim 1, together with a suitable pesticidal carrier material.

22. The use of a compound of the formula I according to claim 1 for controlling pests.

23. The method of controlling or preventing the infestation of pests, which comprises applying a pesticidally effective amount of the compound according to claim 1 to the pests or their environment.

24. The method according to claim 23, wherein the pests are phytopathogenic fungi.

25. The method according to claim 23, wherein the pests are insects or Acarina.

26. A method according to claim 23, wherein applying the composition to the environment comprises application to a seed.

27. Seed which has been treated according to clsim 26.

28. A compound of the formula XV in which $R_1$, $R_2$ and $R_3$ are as defined in claim 1.

29. A compound of the formula XVII in which $R_1$, $R_2$ and $R_3$ are as defined in claim 1.

30. A compound of the formula XIII in which

Z, $R_1$ and $R_2$ are as defined in claim 1.

31. A compound of the formula XVIII in which $R_1$, $R_2$, $R_3$ and R, are as defined in claim 1.

32. A compound of the formula XX in which $R_1$, $R_2$, $R_3$ and $R_4$ are as defined in claim 1.

* * * * *